(12) United States Patent
Jeong

(10) Patent No.: US 9,543,527 B2
(45) Date of Patent: Jan. 10, 2017

(54) RED PHOSPHORESCENT COMPOUND AND ORGANIC LIGHT EMITTING DIODE DEVICE USING THE SAME

(71) Applicant: LG DISPLAY CO., LTD., Seoul (KR)

(72) Inventor: Hyun-Cheol Jeong, Seoul (KR)

(73) Assignee: LG DISPLAY CO., LTD., Seoul (KR)

( * ) Notice: Subject to any disclaimer, the term of this patent is extended or adjusted under 35 U.S.C. 154(b) by 474 days.

(21) Appl. No.: 14/087,277

(22) Filed: Nov. 22, 2013

(65) Prior Publication Data

US 2014/0175402 A1   Jun. 26, 2014

(30) Foreign Application Priority Data

Dec. 26, 2012 (KR) .................. 10-2012-0153125

(51) Int. Cl.
| | | |
|---|---|---|
| H01L 51/50 | (2006.01) | |
| H01L 51/00 | (2006.01) | |
| C07D 401/14 | (2006.01) | |
| C07D 471/04 | (2006.01) | |
| C07D 519/00 | (2006.01) | |

(52) U.S. Cl.
CPC ......... *H01L 51/0067* (2013.01); *C07D 401/14* (2013.01); *C07D 471/04* (2013.01); *C07D 519/00* (2013.01); *H01L 51/0072* (2013.01); *H01L 51/5028* (2013.01); *H01L 51/0081* (2013.01); *H01L 51/0085* (2013.01); *H01L 51/5016* (2013.01)

(58) Field of Classification Search
None
See application file for complete search history.

(56) References Cited

FOREIGN PATENT DOCUMENTS

| WO | WO 2010/114264 | * 10/2010 | ............. C09K 11/06 |
|---|---|---|---|
| WO | WO 2010/114264 A2 | 10/2010 | |

OTHER PUBLICATIONS

Office Action issued in Chinese Patent Application No. 201310627623.7, mailed Apr. 23, 2015, 10 pages.

* cited by examiner

*Primary Examiner* — Gregory Clark
(74) *Attorney, Agent, or Firm* — Brinks Gilson & Lione

(57) ABSTRACT

The present invention provides a phosphorescent compound of one of following formulas:

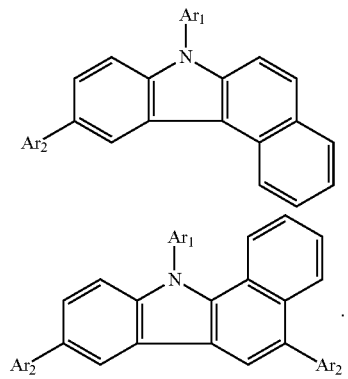

16 Claims, 2 Drawing Sheets

RED PHOSPHORESCENT COMPOUND AND ORGANIC LIGHT EMITTING DIODE DEVICE USING THE SAME

The present application claims the benefit of priority to Korean Patent Application No. 10-2012-0153125 filed in Korea on Dec. 26, 2012, which is hereby incorporated by reference in its entirety.

BACKGROUND

Field of the Disclosure

The present disclosure relates to a red phosphorescent compound and an organic light emitting diode (OLED) device and more particularly to a soluble red phosphorescent compound having excellent color purity and high brightness and emitting efficiency and an OLED device using the same.

Discussion of the Related Art

Recently, the requirements for flat panel display devices, such as a liquid crystal display device and a plasma display panel, have increased. However, these flat panel display devices have relatively slow response time and narrow viewing angle in comparison to the cathode ray tube (CRT).

An organic light emitting diode (OLED) device is one of next-generation flat panel display devices being capable of resolving the above problems while occupying a small area.

Elements of the OLED device can be formed on a flexible substrate such as a plastic substrate. In addition, the OLED device has advantages in the viewing angle, the driving voltage, the power consumption and the color purity. Moreover, the OLED device is adequate to produce full-color images.

Generally, the emitting diode of the OLED device includes the anode, the hole injecting layer (HIL), the hole transporting layer (HTL), the emitting material layer (EML), the electron transporting layer (ETL), the electron injecting layer (EIL) and the cathode.

The OLED device emits light by injecting electrons from a cathode as an electron injection electrode and holes from an anode as a hole injection electrode into an emission compound layer, combining the electrons with the holes, generating an exciton, and transiting the exciton from an excited state to a ground state.

The emitting principle may be classified into fluorescent emission and phosphorescent emission. In the fluorescent emission, the organic molecule in the singlet exited state is transited to the ground state such that light is emitted. On the other hand, in the phosphorescent emission, the organic molecule in the triplet exited state is transited to the ground state such that light is emitted.

When the emitting material layer emits light corresponding to an energy band gap, the singlet exciton having 0 spin and the triplet exciton having 1 spin are generated with a ratio of 1:3. The ground state of the organic material is the singlet state such that the singlet exciton can be transited to the ground state with emitting light. However, since the triplet exciton can not be transited with emitting light, the internal quantum efficiency of the OLED device using the fluorescent material is limited within 25%.

On the other hand, if the spin-orbital coupling momentum is high, the singlet state and the triplet state are mixed such that an inter-system crossing is generated between the singlet state and the triplet state and the triplet exciton also can be transited to the ground state with emitting light. The phosphorescent material can use the triplet exciton as well as the singlet exciton such that the OLED device using the phosphorescent material may have 100% internal quantum efficiency.

Recently, iridium complex, e.g., bis(2-phenylquinoline)(acetylacetonate)iridium(III)(Ir(2-phq)2(acac)), bis(2-benzo[b]thiophene-2-yl-pyridine)(acetylacetonate)iridium(III)(Ir(btp)2(acac)) and tris(2-phenylquinoline)iridium(III)(Ir(2-phq)3), as a dopant has been introduced.

To obtain high current emitting efficiency (Cd/A) with the phosphorescent material, excellent internal quantum efficiency, high color purity and long life-time are required. Particularly, referring to FIG. 1, as the color purity becomes higher, i.e., higher CIE(X), the color sensitivity becomes bad. As a result, with the high internal quantum efficiency, it is very difficult to obtain emitting efficiency. Accordingly, new red phosphorescent compound having excellent color purity (CIE(X)≥0.65) and high emitting efficiency is required.

On the other hand, in addition to the above iridium complex, another complex, for example 4,4-N,N-dicarbazole-biphenyl (CBP), is used as the red phosphorescent compound. However, these compounds do not have desirable solubility in solvent such that it is impossible to form an emitting layer by a solution process. Since the emitting layer should be formed by a deposition process, a fabricating process is very complex and a process efficiency is very low. In addition, wasted material is very much in the deposition process such that production costs are increased.

SUMMARY

A red phosphorescent compound has the following formula:

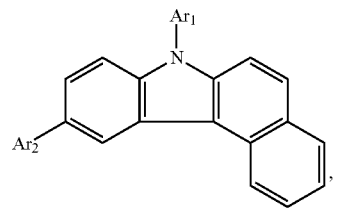

wherein each of Ar1 and Ar2 is independently selected from hydrogen, a substituted or non-substituted heteroaromatic group, a substituted or non-substituted alicyclic group and a substituted or non-substituted aliphatic group, and at least one of Ar1 and Ar2 is not hydrogen.

In another aspect of the present invention, a red phosphorescent compound has the following formula:

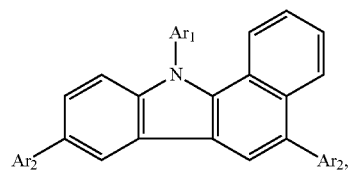

wherein each of Ar1 and Ar2 is independently selected from hydrogen, a substituted or non-substituted heteroaromatic group, a substituted or non-substituted alicyclic group and a substituted or non-substituted aliphatic group, and at least one of Ar1 and Ar2 is not hydrogen.

In another aspect of the present invention, an organic light emitting diode device includes a first electrode; a second electrode facing the first electrode; and an emitting material layer between the first and second electrodes and including a red phosphorescent compound of following formula:

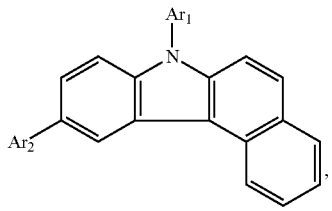

wherein each of Ar1 and Ar2 is independently selected from hydrogen, a substituted or non-substituted heteroaromatic group, a substituted or non-substituted alicyclic group and a substituted or non-substituted aliphatic group, and at least one of Ar1 and Ar2 is not hydrogen.

In another aspect of the present invention, an organic light emitting diode device includes a first electrode; a second electrode facing the first electrode; and an emitting material layer between the first and second electrodes and including a red phosphorescent compound of following formula:

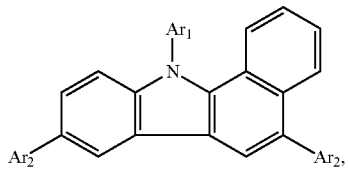

wherein each of Ar1 and Ar2 is independently selected from hydrogen, a substituted or non-substituted heteroaromatic group, a substituted or non-substituted alicyclic group and a substituted or non-substituted aliphatic group, and at least one of Ar1 and Ar2 is not hydrogen.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EXEMPLARY EMBODIMENTS

Figure 1:
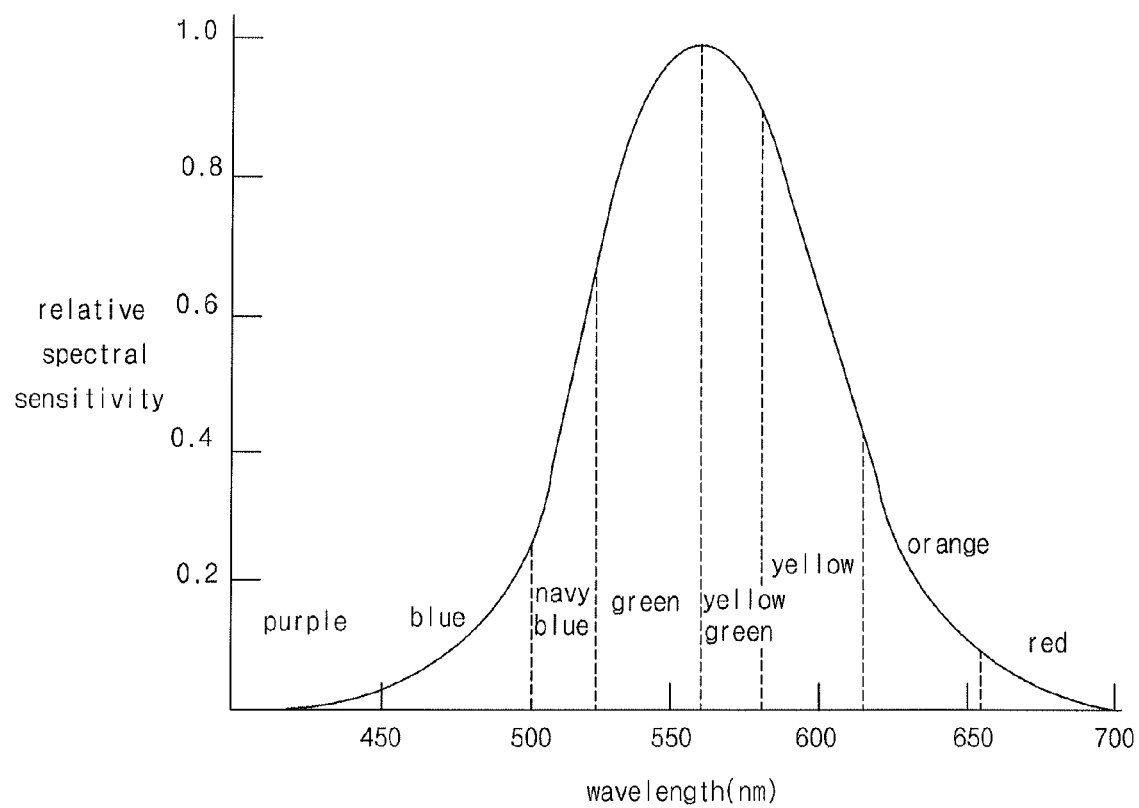
FIG. 1 is a graph showing a relation of a color purity and a visible sensitivity.

Reference will now be made in detail to the preferred embodiments, examples of which are illustrated in the accompanying drawings.

The present invention provides a red phosphorescent compound having excellent color purity and improved emitting efficiency with high internal quantum efficiency and an OLED device using the red phosphorescent compound.

Red Phosphorescent Compound

—First Embodiment—

The red phosphorescent compound of a first embodiment of the present invention includes benzo[3,4]carbazole core. The benzo[3,4]carbazole core is substituted by a heteroaromatic group, an alicyclic group and an aliphatic group. The red phosphorescent compound is represented by following Formula 1.

[Formula 1]

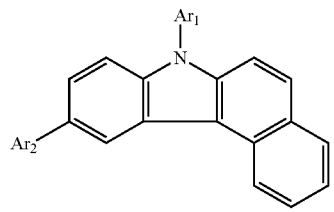

In the above Formula 1, each of Ar1 and Ar2 is independently selected from hydrogen, a substituted or non-substituted heteroaromatic group, a substituted or non-substituted alicyclic group and a substituted or non-substituted aliphatic group. At least one of Ar1 and Ar2 is not hydrogen. Namely, at least one of Ar1 and Ar2 is selected from the substituted or non-substituted heteroaromatic group, the substituted or non-substituted alicyclic group and the substituted or non-substituted aliphatic group.

For example, the heteroaromatic group for Ar1 and Ar2 may include pyridinyl, bipyridinyl, quinolinyl, isoquinolinyl, terpyridinyl and phenanthrolinyl. The alicyclic group may include five to seven carbons. For example, the alicyclic group may include pyrrolidine, imidazolidine, pyrazolidine, piperidine, piperazine, morpholine, triazine and azepane. The aliphatic compound may include C1~C20 alkyl, beneficially C1~C10 alkyl.

Each of Ar2 and Ar2 is independently substituted by C5~C20 aryl, C1~C10 alkyl, C1~C10 alkoxy, halogen, e.g., fluorine and chloride, cyano and silyl.

The C5~C20 aryl substituent may include pyridinyl, bipyridinyl, quinolinyl, isoquinolinyl, terpyridinyl and phenanthrolinyl, and the C1~C10 alkyl substituent may include methyl, ethyl, propyl, iso-propyl and butyl. The C1~C10 alkoxy may include methoxy, ethoxy, buthoxy, and the silyl substituent may be substituted by C1~C5 alkyl, e.g., trimethylsilyl.

Each of Ar1 and Ar2 in the above Formula 1 may be one of followings in Formula 2.

[Formula 2]

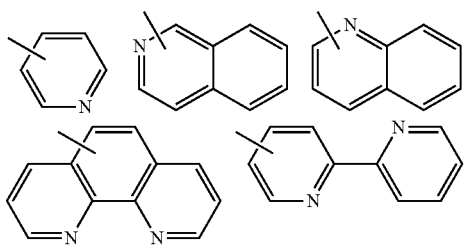

-continued
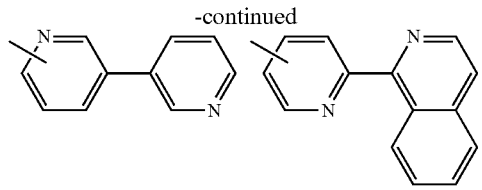
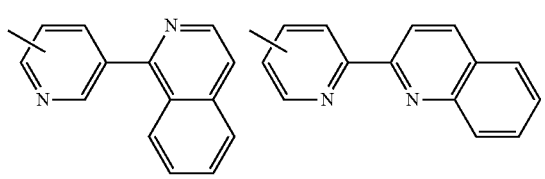
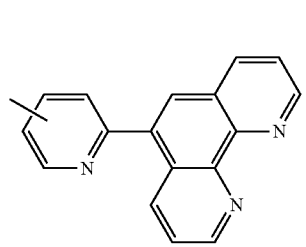
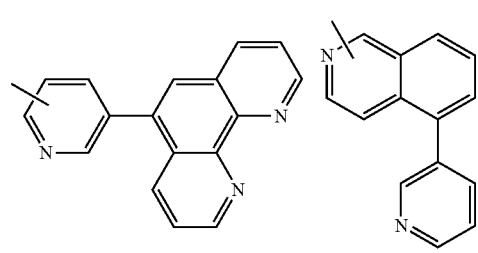
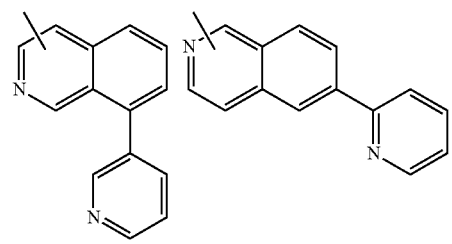
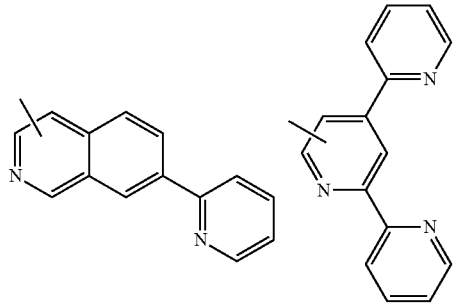
With Ar1 and Ar2, the red phosphorescent compound in the above Formula 1 may be one of followings in Formula 3.
[Formula 3]
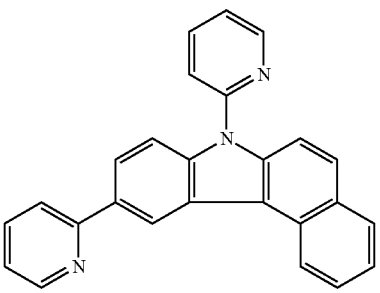
RH-01
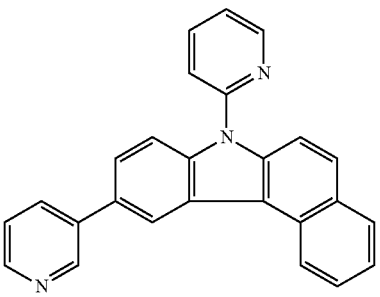
RH-02
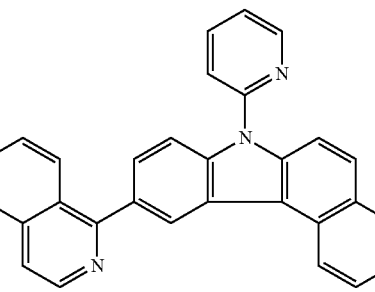
RH-03
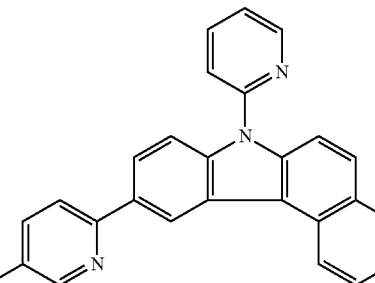
RH-04
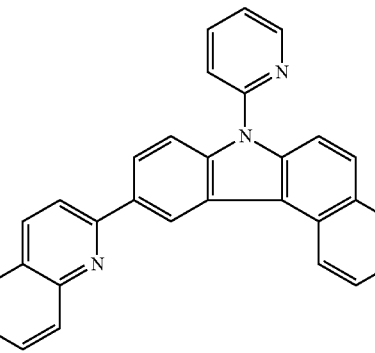

RH-05
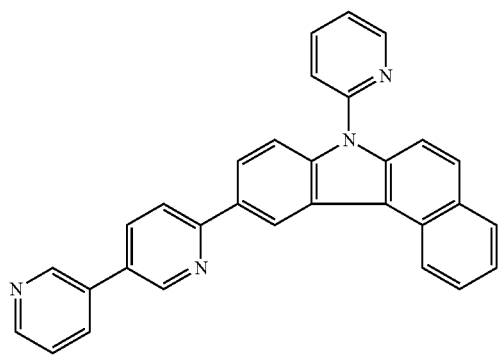
RH-06
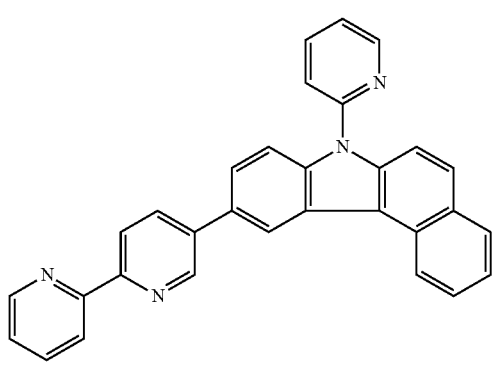
RH-07
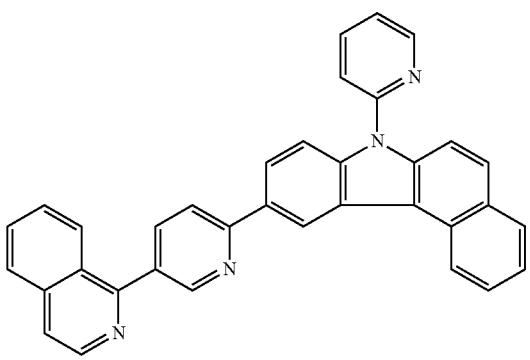
RH-08
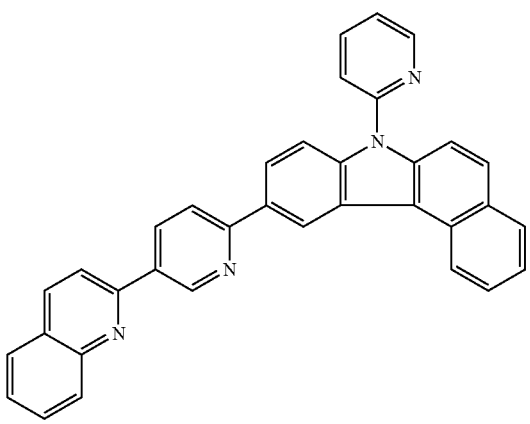
RH-09
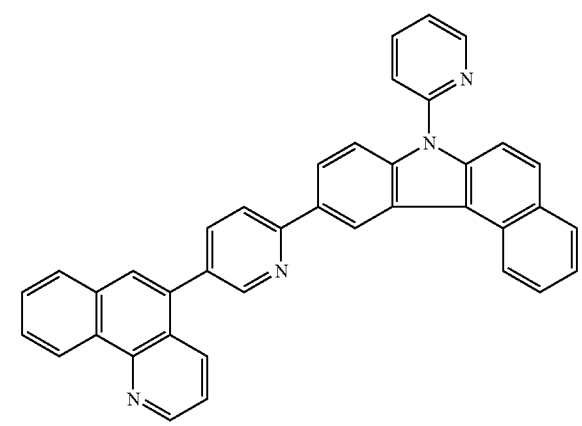
RH-13
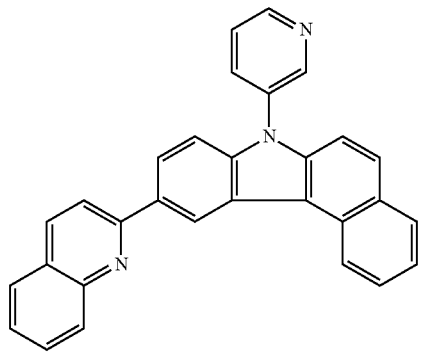
RH-14
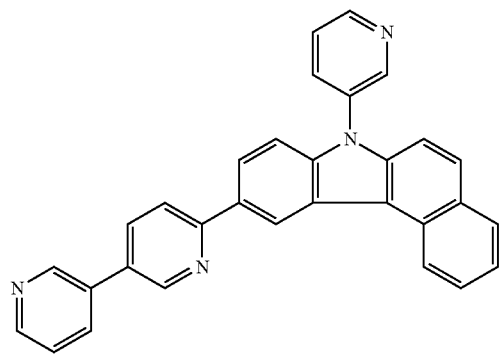
RH-15
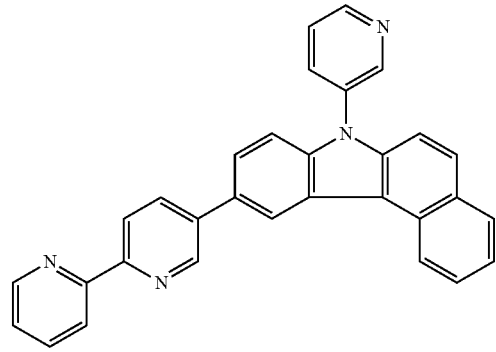

-continued

RH-16
RH-17
RH-18
RH-19
RH-20
RH-21
RH-22
RH-23

-continued
RH-24
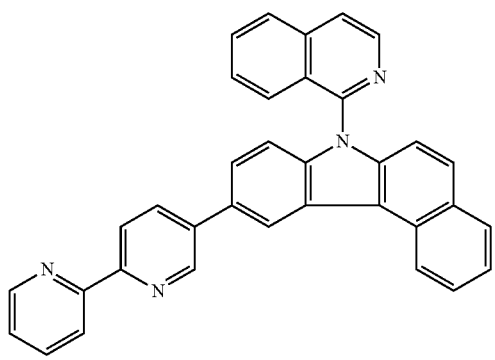
RH-25
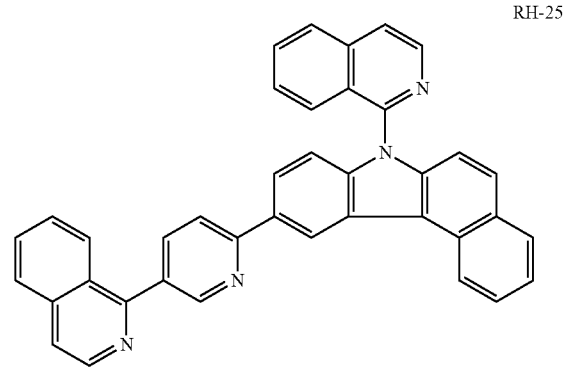
RH-26
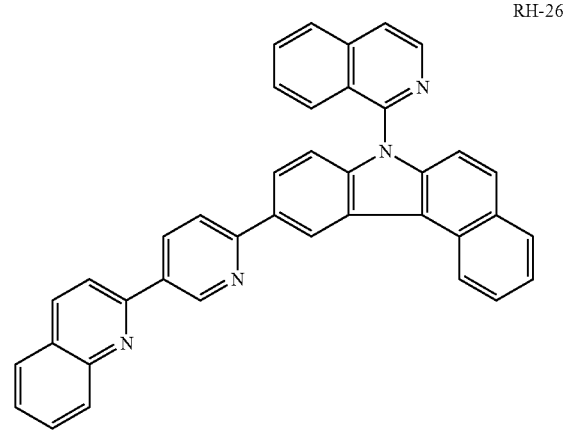
RH-27
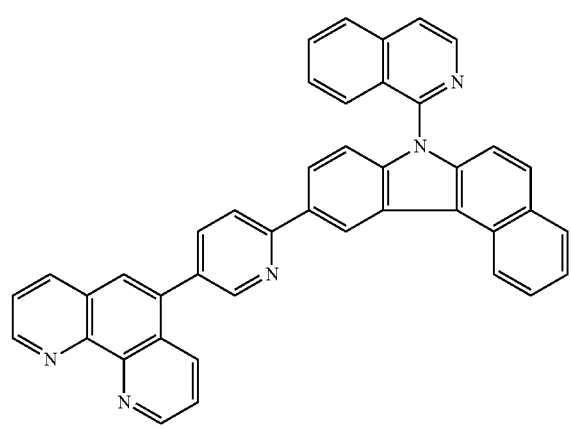
-continued
RH-28
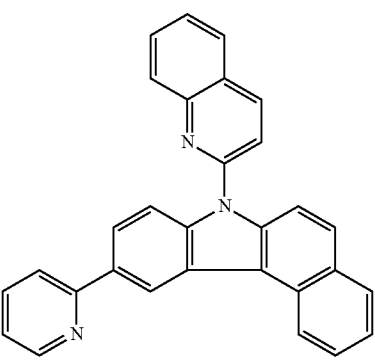
RH-29
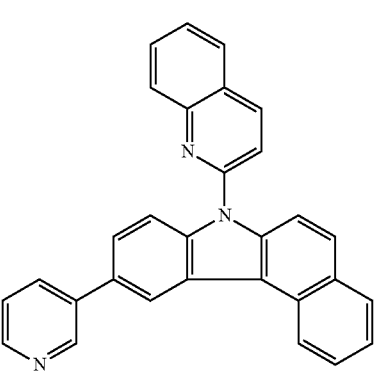
RH-30
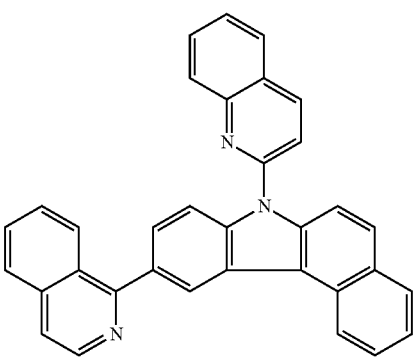
RH-31
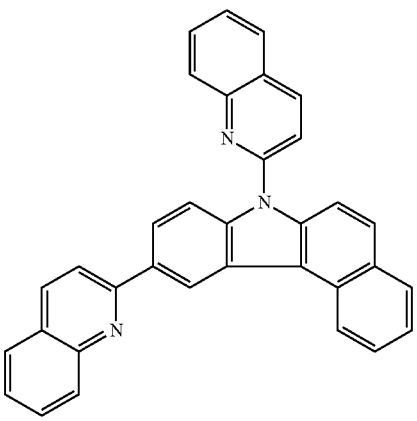

RH-32
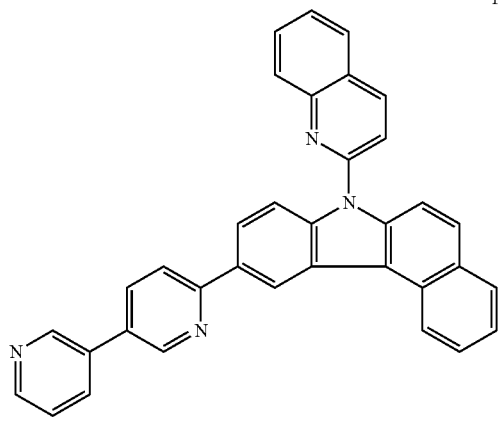
RH-33
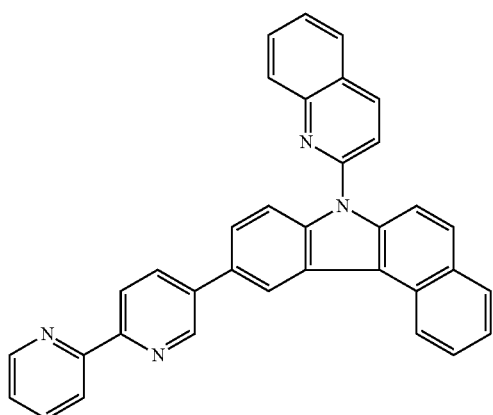
RH-34
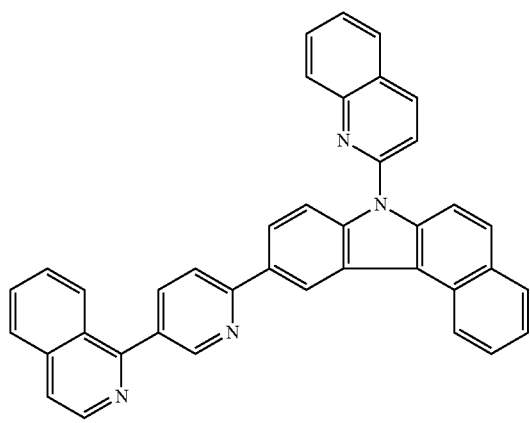
RH-35
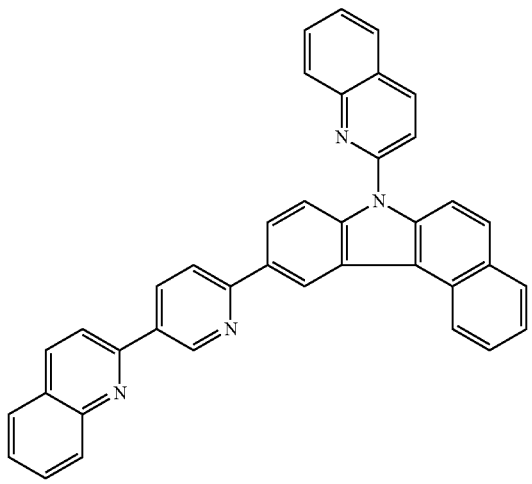
RH-36
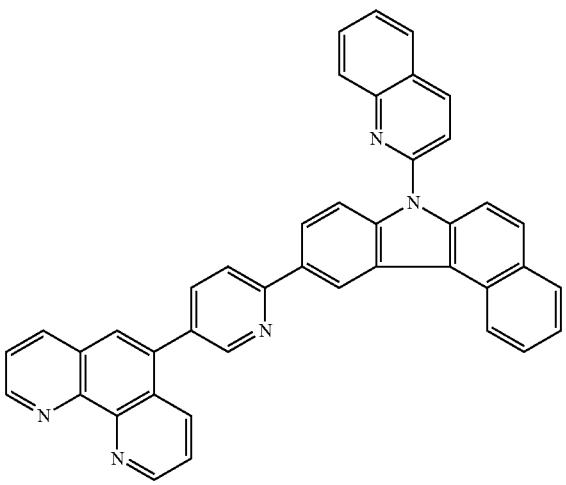
RH-37
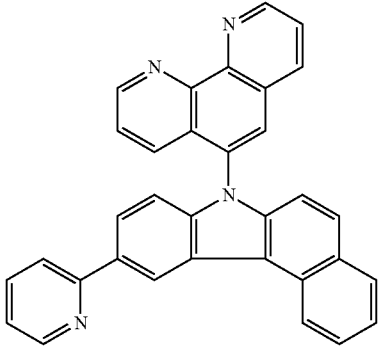

RH-38
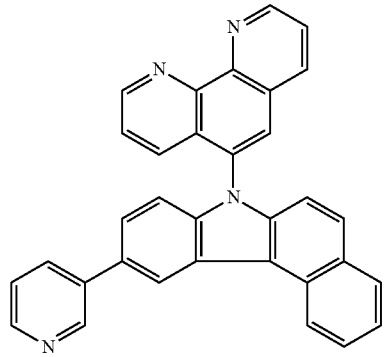
RH-39
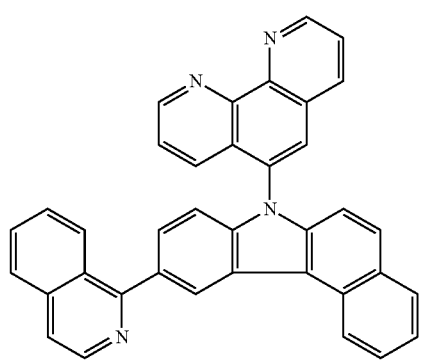
RH-40
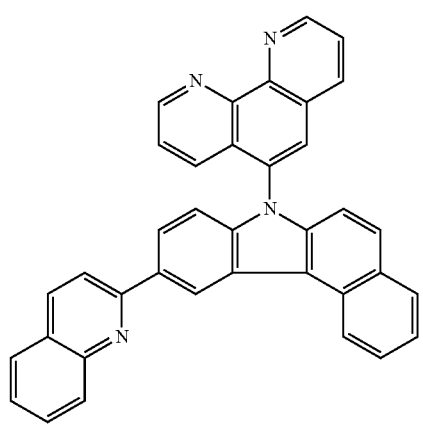
RH-41
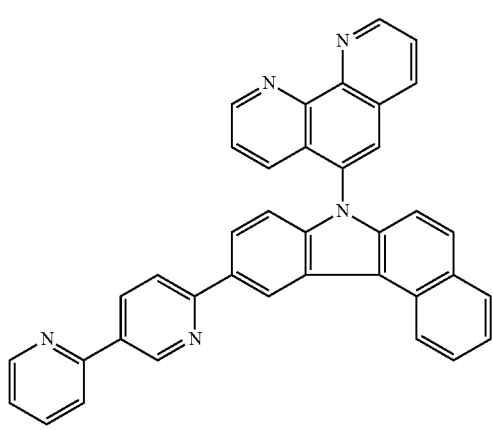
RH-42
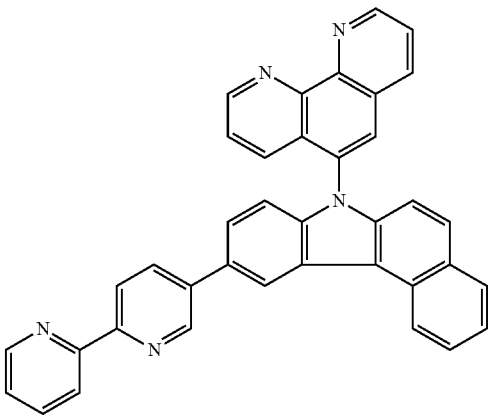
RH-43
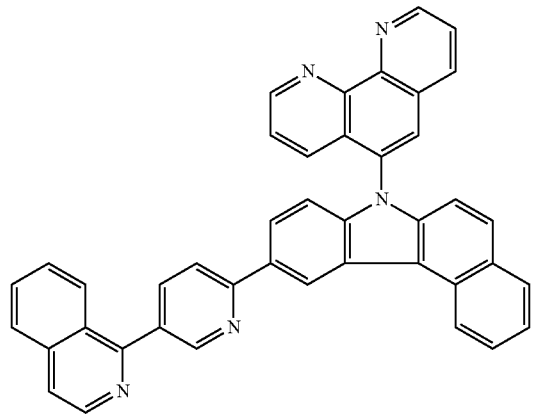
RH-44
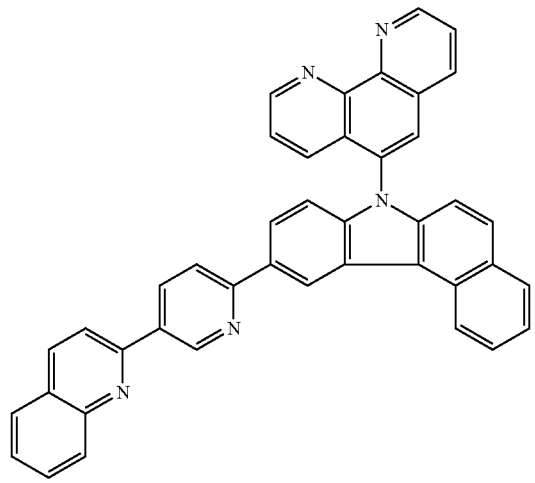

RH-45
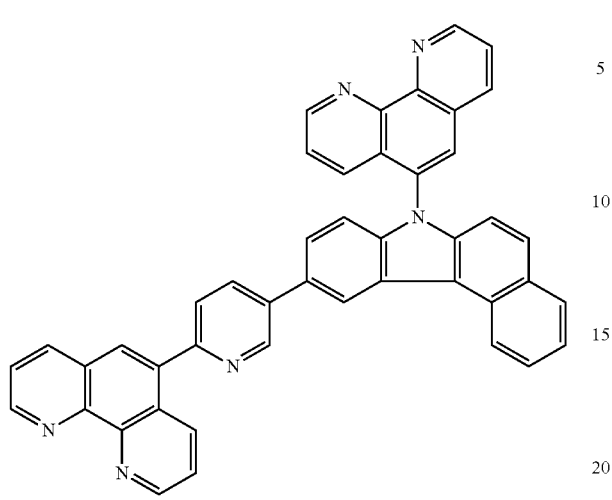
RH-48
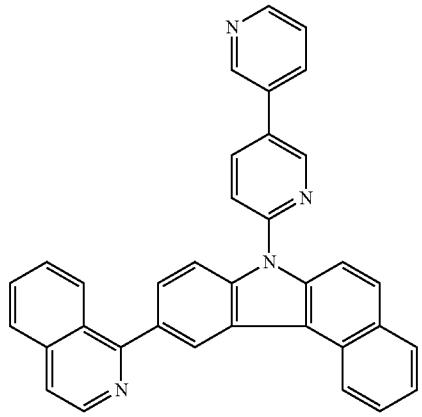
RH-46
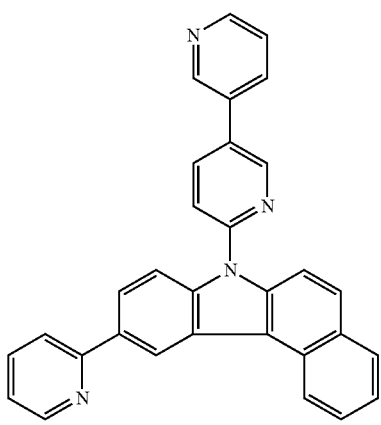
RH-49
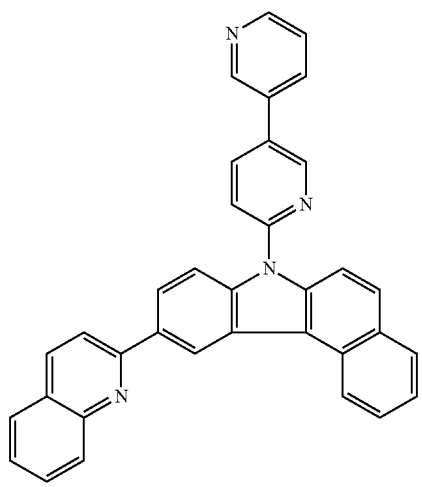
RH-47
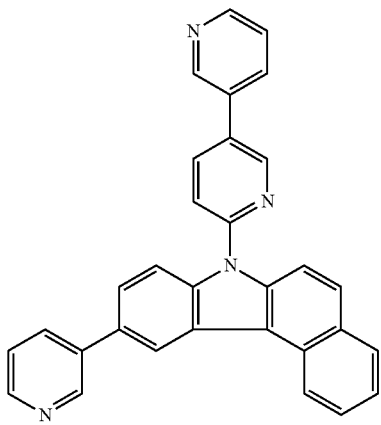
RH-50
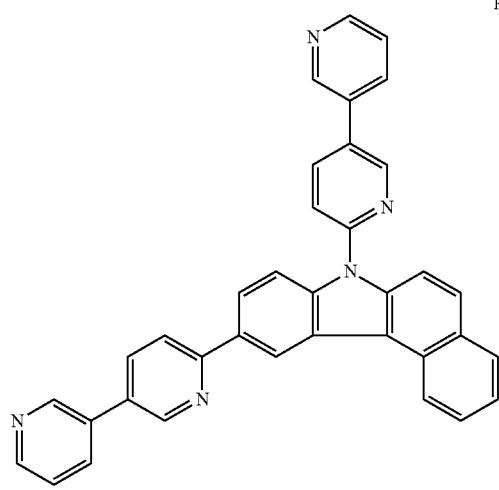

-continued
RH-51
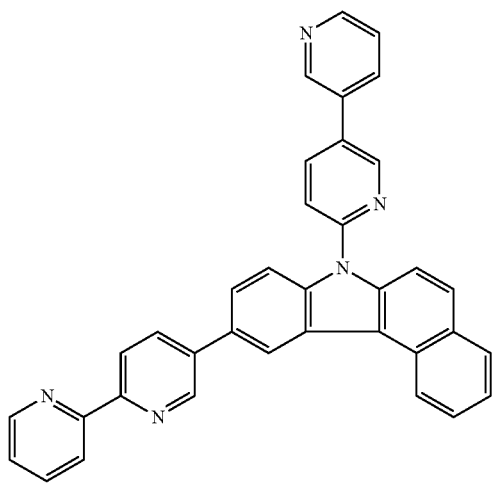
RH-52
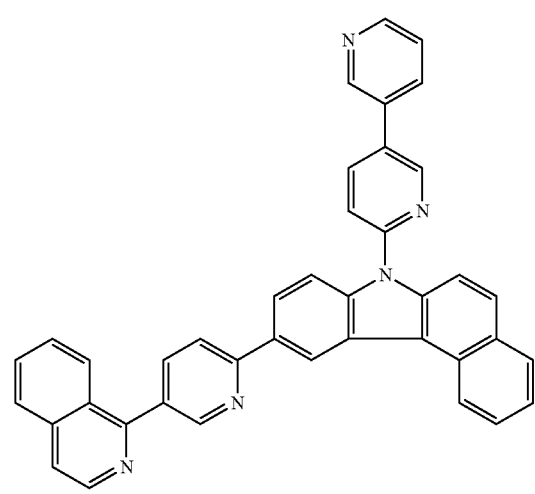
RH-53
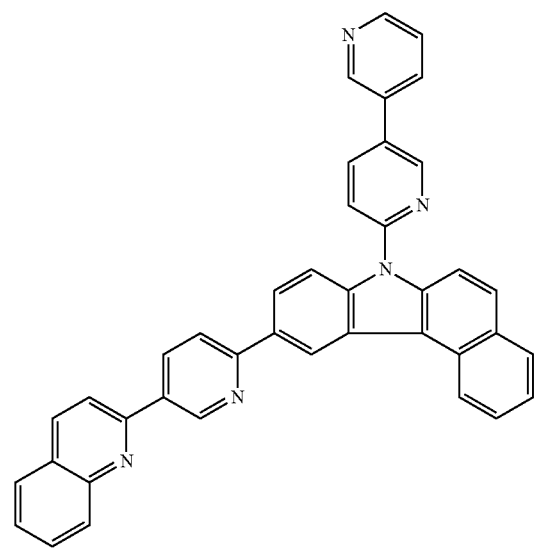
-continued
RH-54
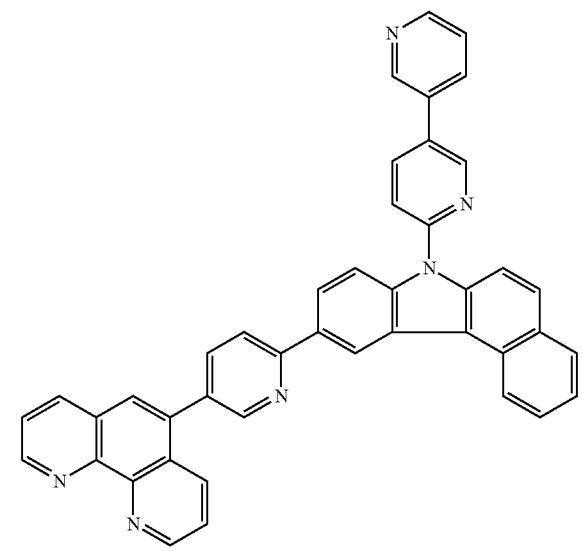
RH-55
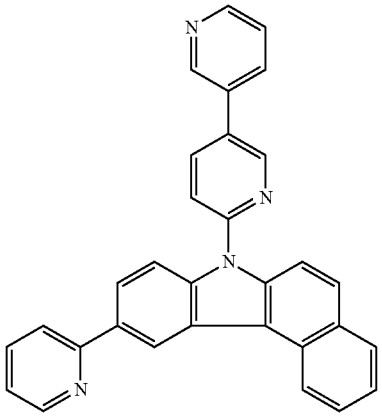
RH-56
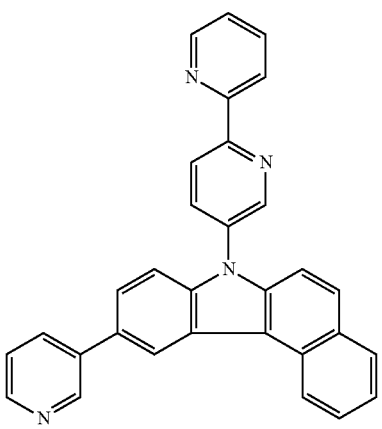

RH-57
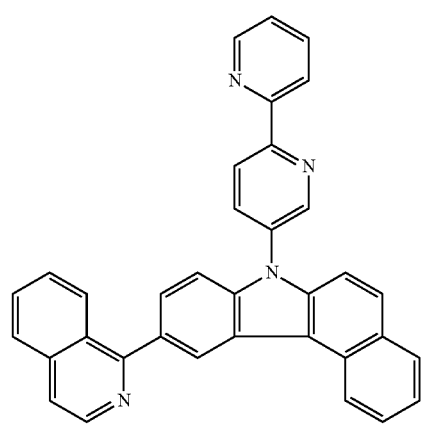
RH-58
RH-59
RH-60
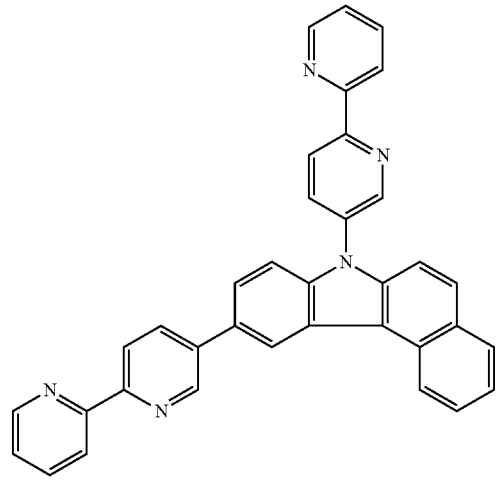
RH-61
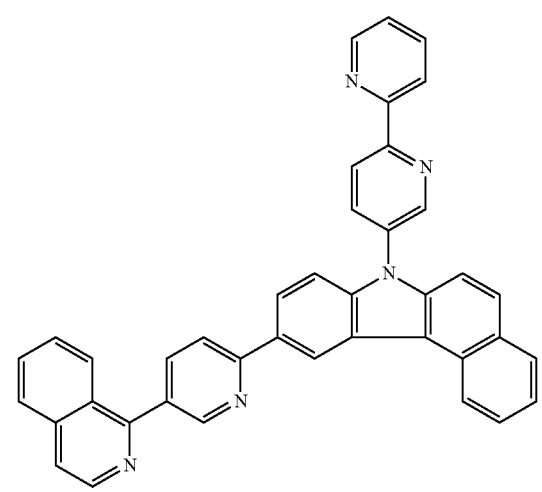
RH-62
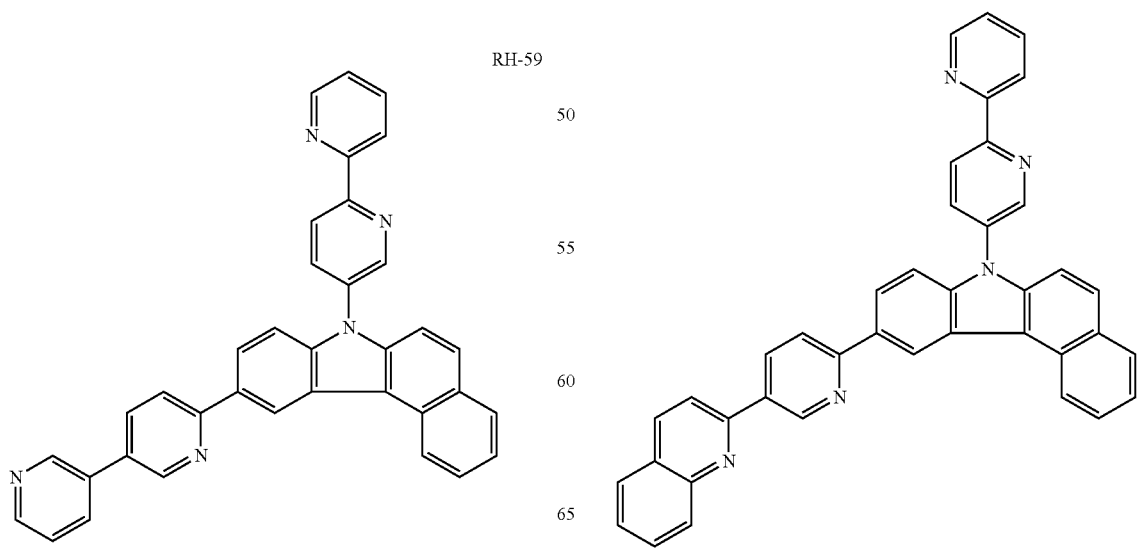

RH-63
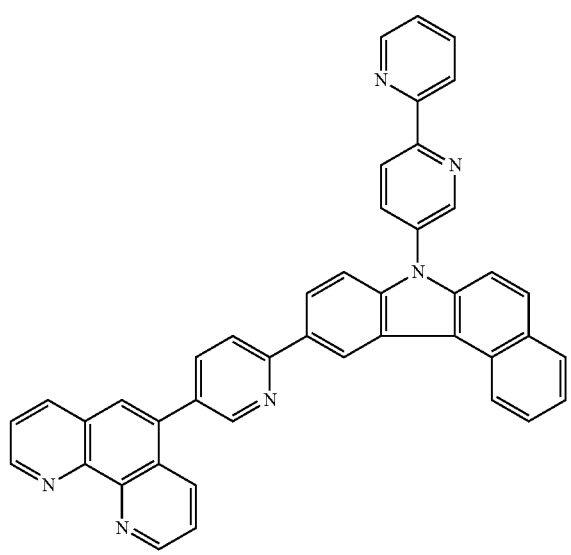
RH-64
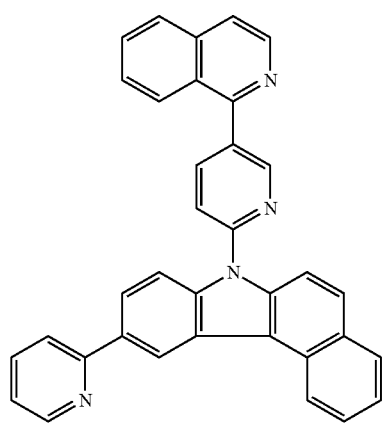
RH-65
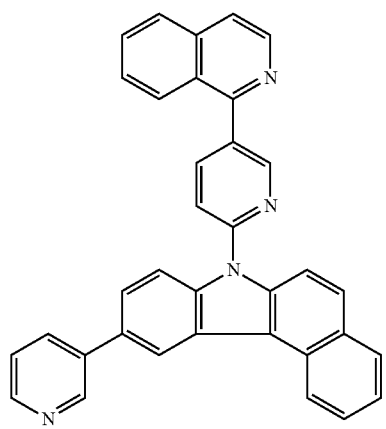
RH-66
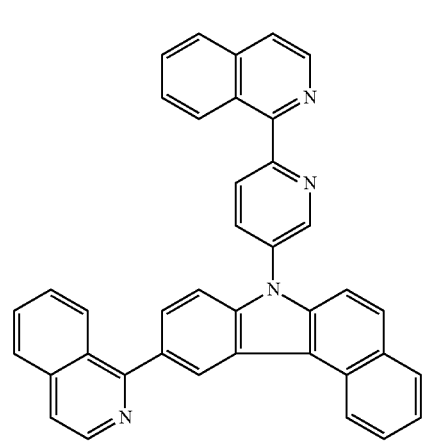
RH-67
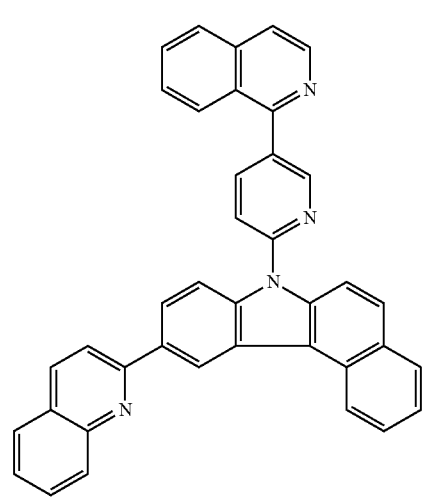
RH-68
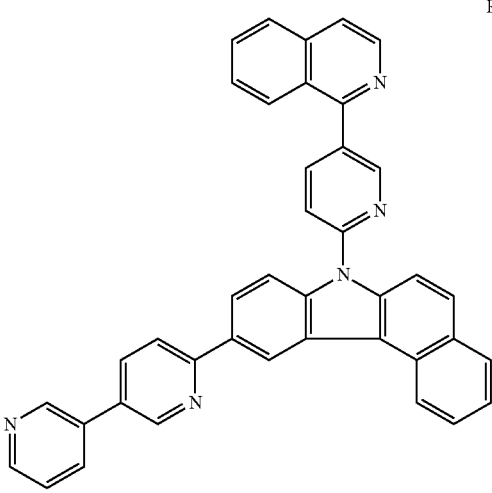

-continued
RH-69
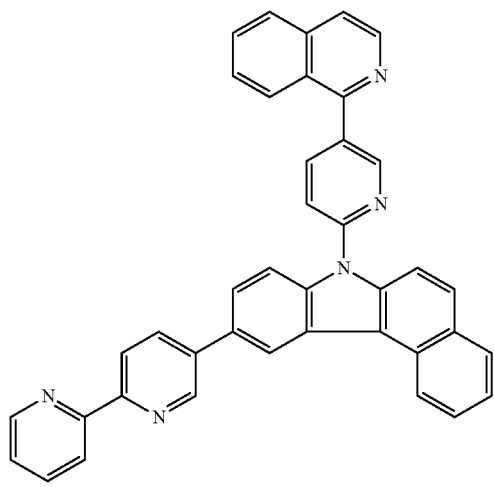
RH-70
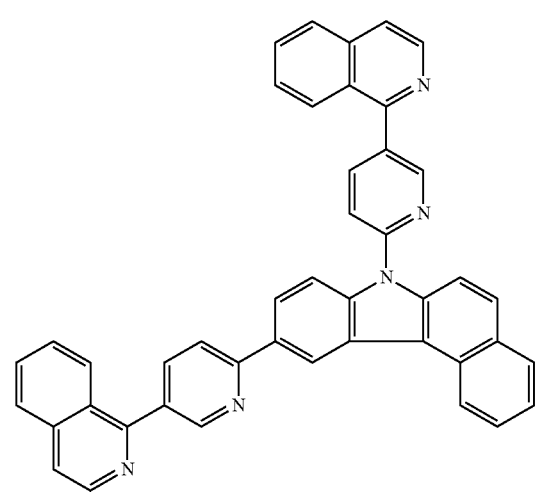
RH-71
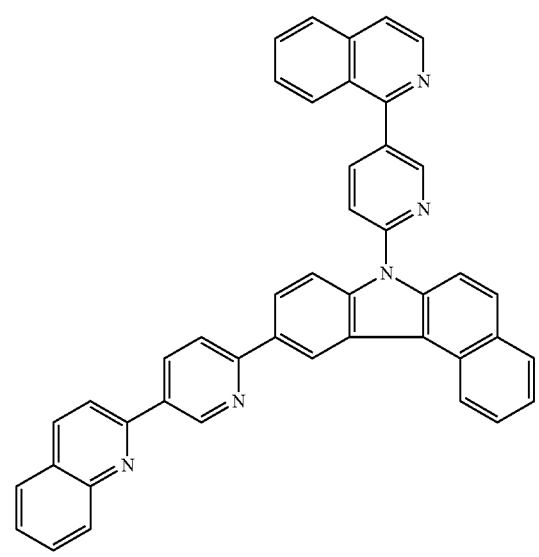
-continued
RH-72
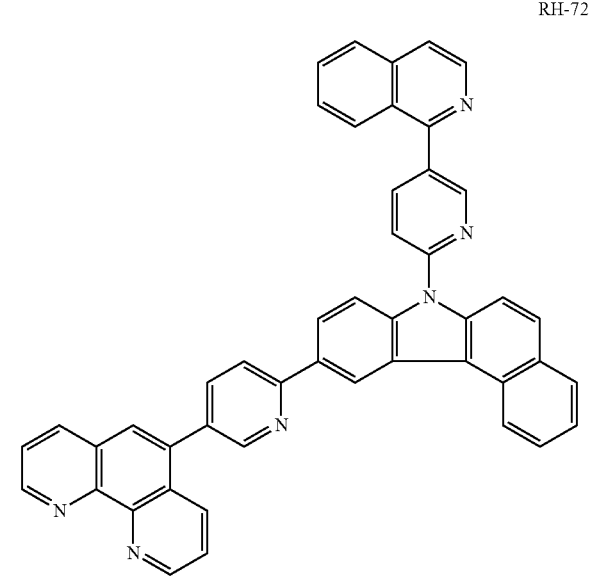
RH-73
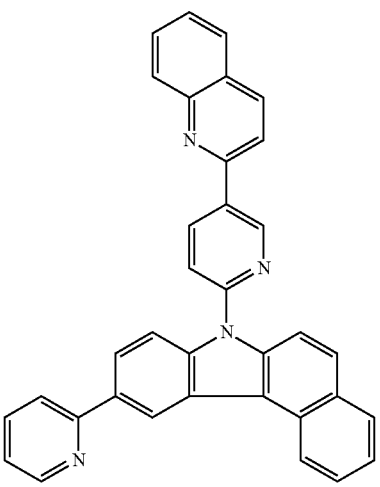
RH-74
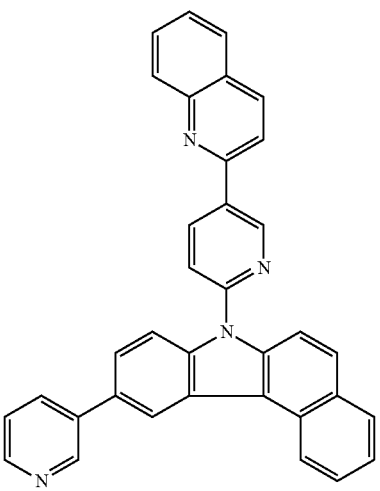

RH-75
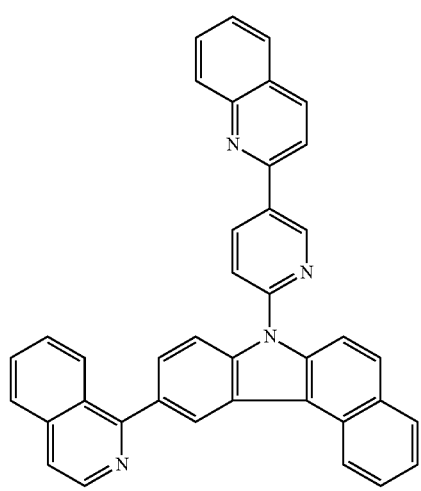
RH-76
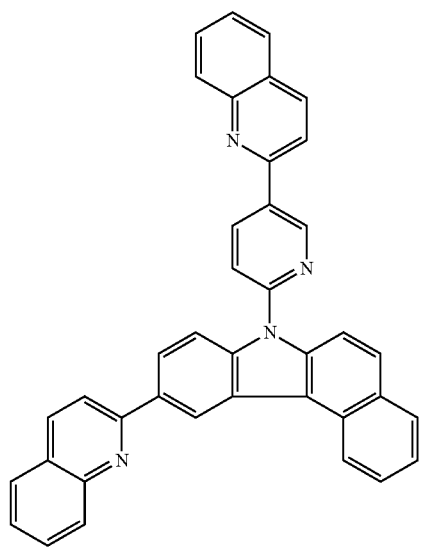
RH-77
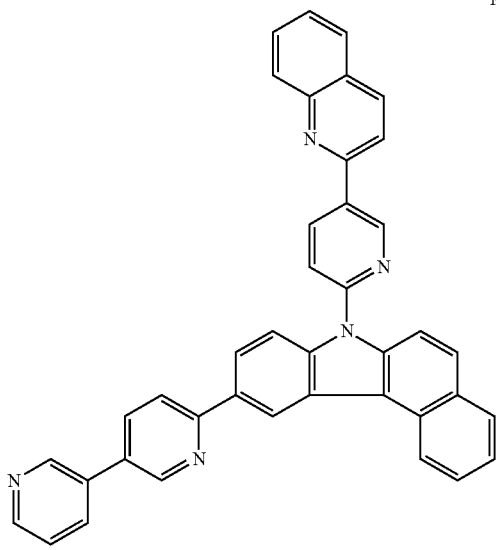
RH-78
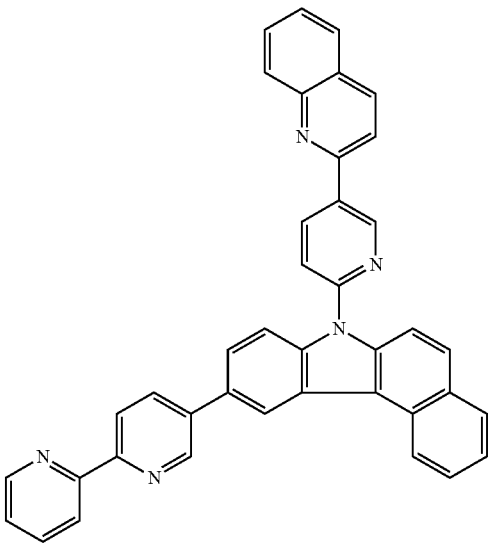
RH-79
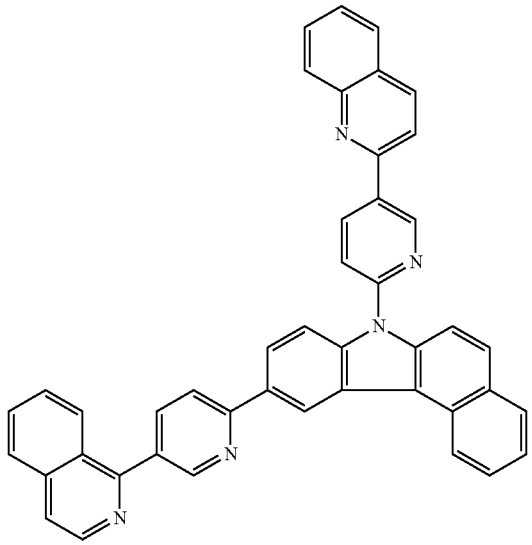

RH-80
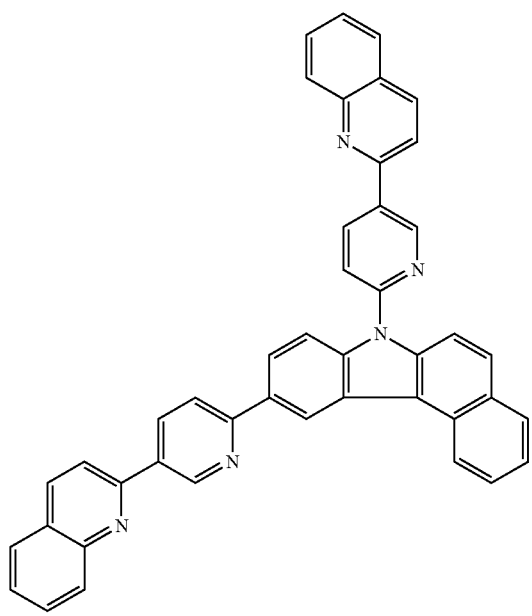
RH-81
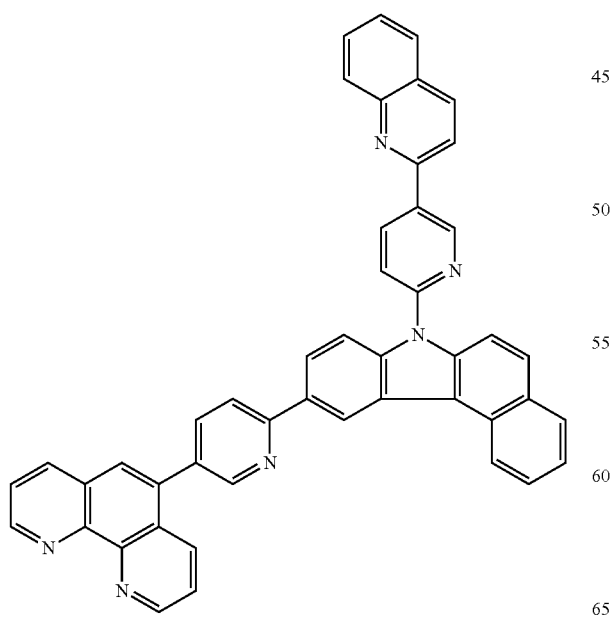
RH-82
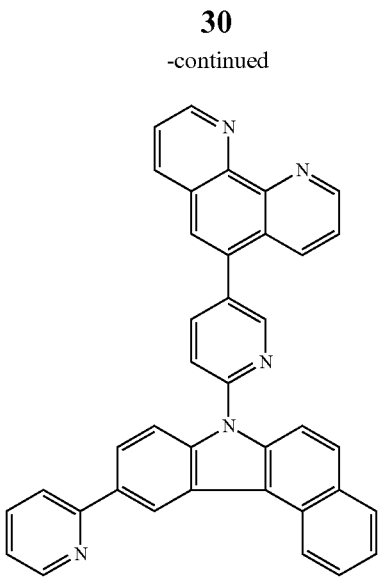
RH-83
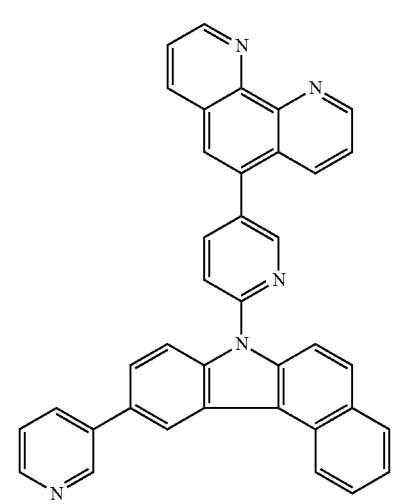
RH-84
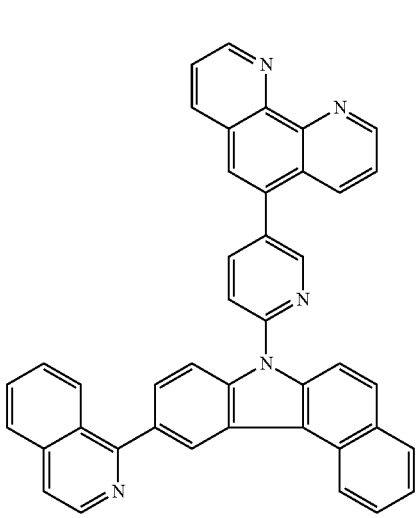

RH-85
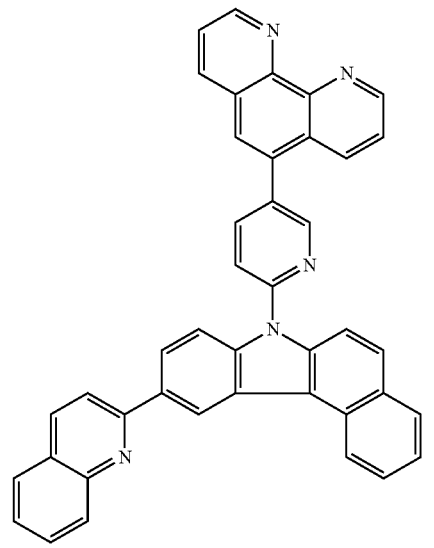
RH-86
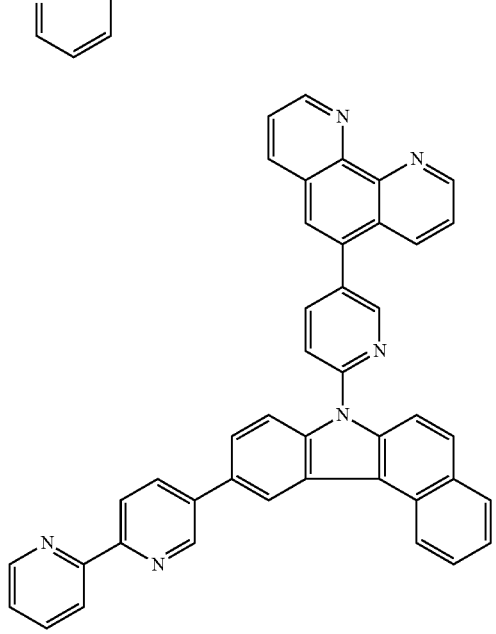
RH-88
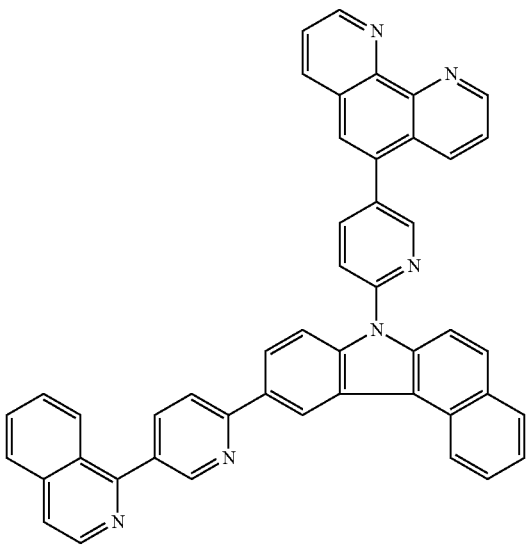
RH-89
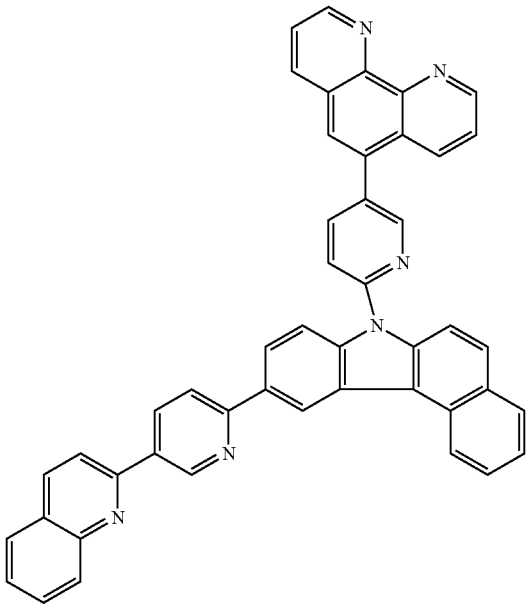
RH-87

-continued

RH-90

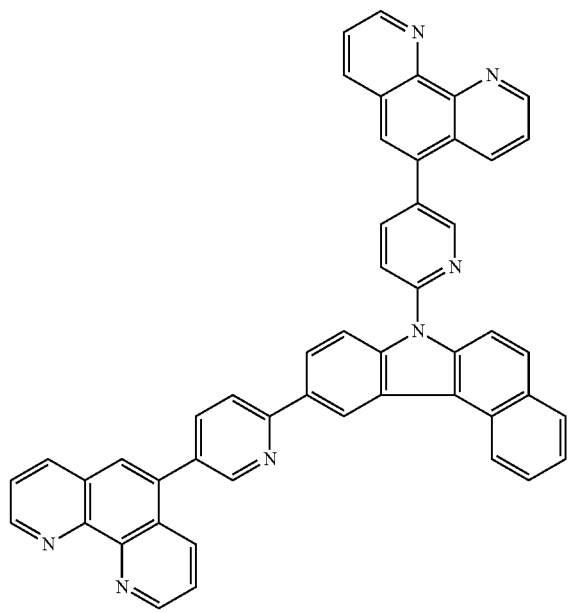

—Second Embodiment—

The red phosphorescent compound of a second embodiment of the present invention includes benzo[1,2]carbazole core. The benzo[1,2]carbazole core is substituted by a heteroaromatic group, an alicyclic group and an aliphatic group. The red phosphorescent compound is represented by following Formula 4.

[Formula 4]

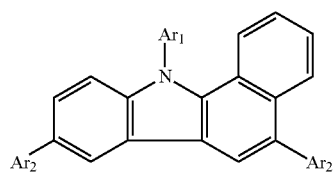

In the above Formula 4, each of Ar1 and Ar2 is independently selected from hydrogen, a substituted or non-substituted heteroaromatic group, a substituted or non-substituted alicyclic group and a substituted or non-substituted aliphatic group. At least one of Ar1 and Ar2 is not hydrogen. Namely, at least one of Ar1 and Ar2 is selected from the substituted or non-substituted heteroaromatic group, the substituted or non-substituted alicyclic group and the substituted or non-substituted aliphatic group.

For example, the heteroaromatic group for Ar1 and Ar2 may include pyridinyl, bipyridinyl, quinolinyl, isoquinolinyl, terpyridinyl and phenanthrolinyl. The alicyclic group may include five to seven carbons. For example, the alicyclic group may include pyrrolidine, imidazolidine, pyrazolidine, piperidine, piperazine, morpholine, triazine and azepane. The aliphatic compound may include C1~C10 alkyl, beneficially C1~C10 alkyl.

Each of Ar2 and Ar2 is independently substituted by C5~C20 aryl, e.g., pyridinyl, bipyridinyl, quinolinyl, isoquinolinyl, terpyridinyl and phenanthrolinyl, C1~C10 alkyl, e.g., methyl, ethyl, propyl, iso-propyl and butyl, C1~C10 alkoxy, e.g., methoxy, ethoxy, buthoxy, halogen, e.g., fluorine and chloride, cyano and silyl substituted C1~C5 alkyl, e.g., trimethylsilyl.

Each of Ar1 and Ar2 in the above Formula 4 may be one of followings in Formula 5.

[Formula 5]

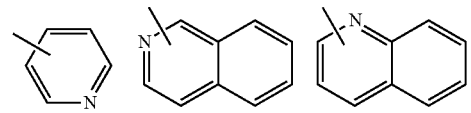

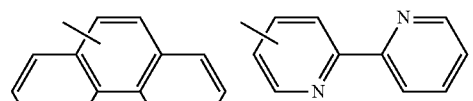

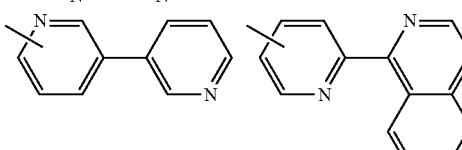

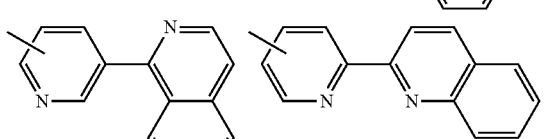

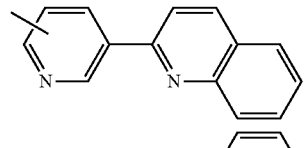

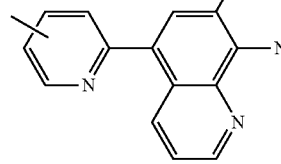

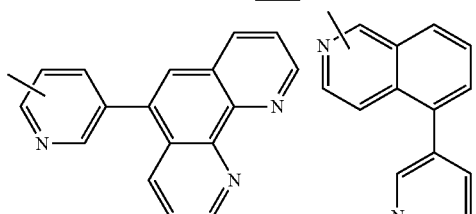

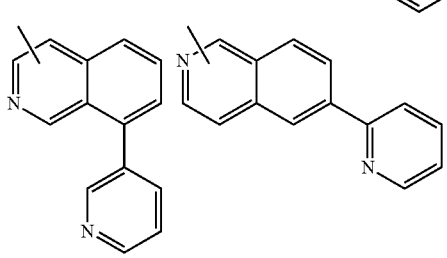

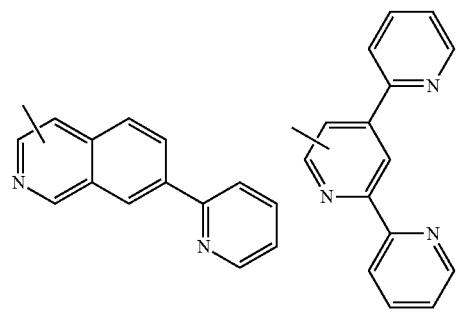
With Ar1 and Ar2, the red phosphorescent compound in the above Formula 4 may be one of followings in Formula 6.
[Formula 6]
RI-01
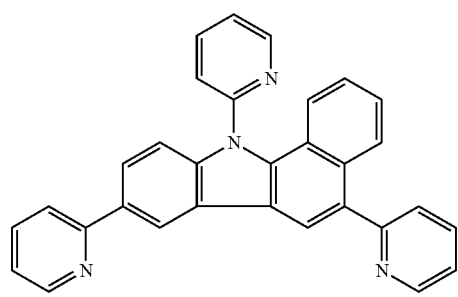
RI-02
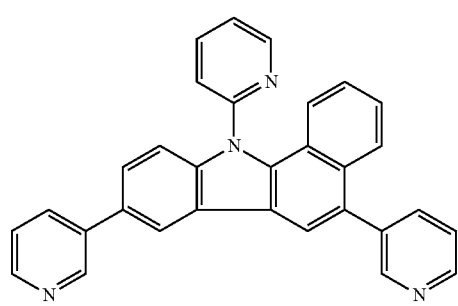
RI-03
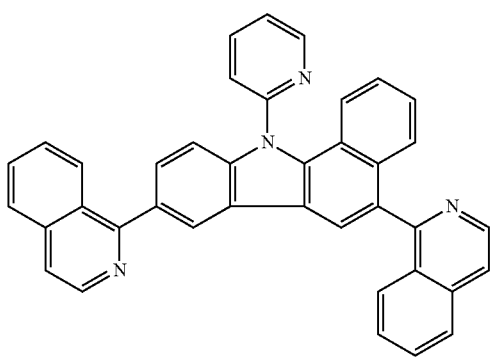
RI-04
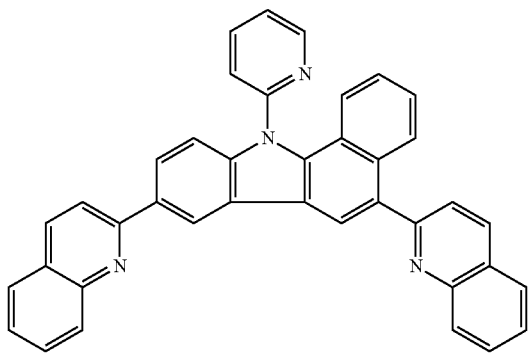
RI-05
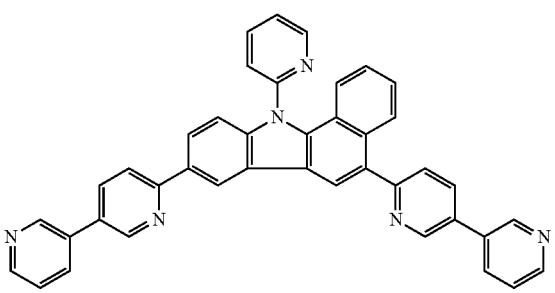
RI-06
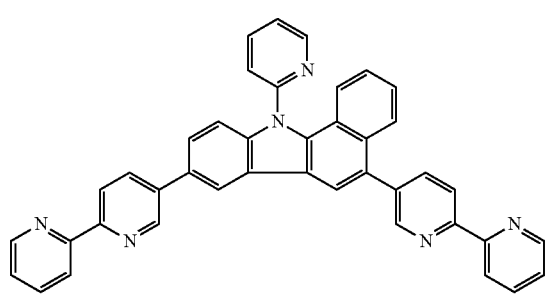
RI-07
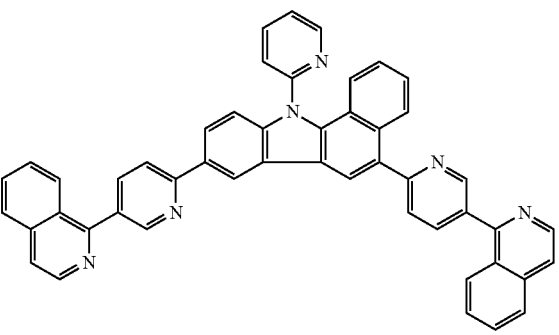

RI-08
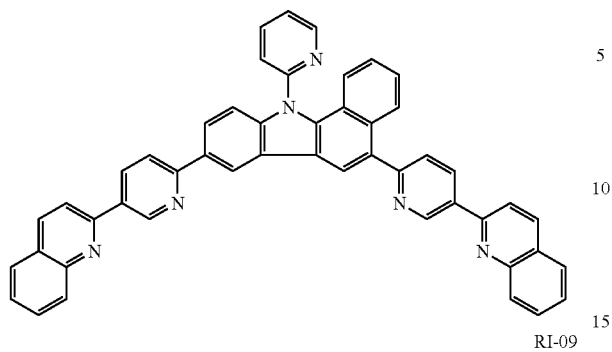
RI-13
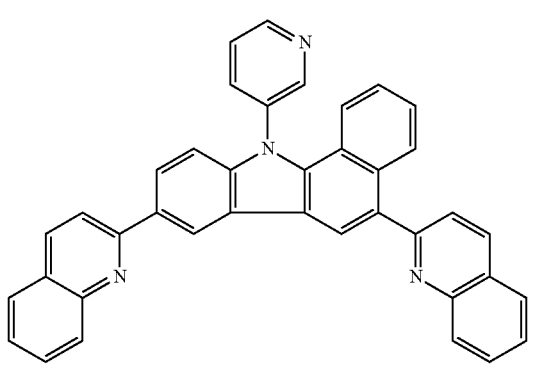
RI-09
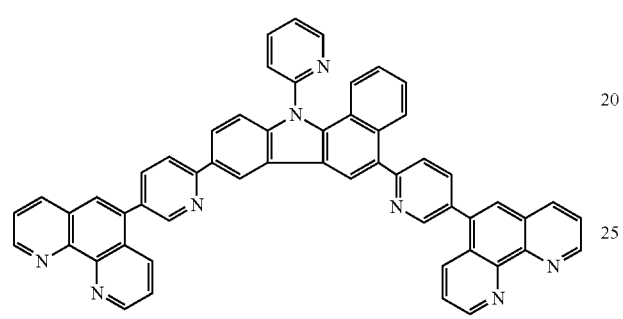
RI-14
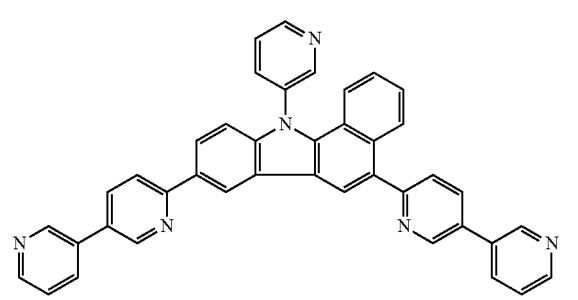
RI-10
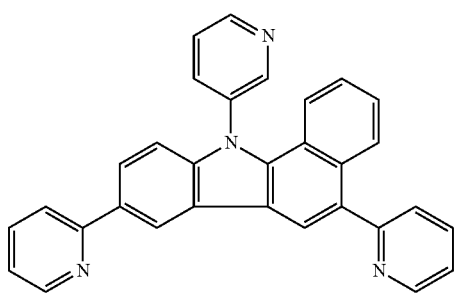
RI-11
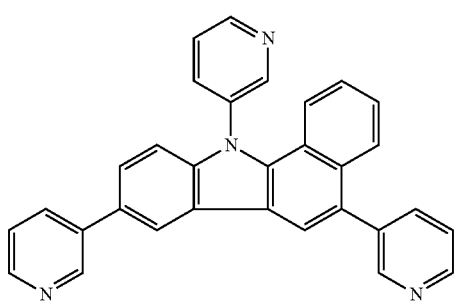
RI-15
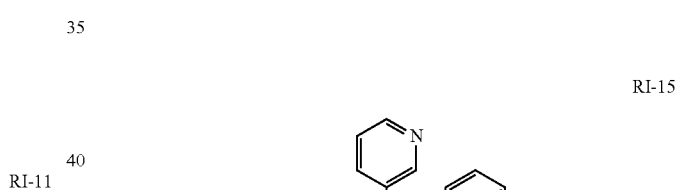
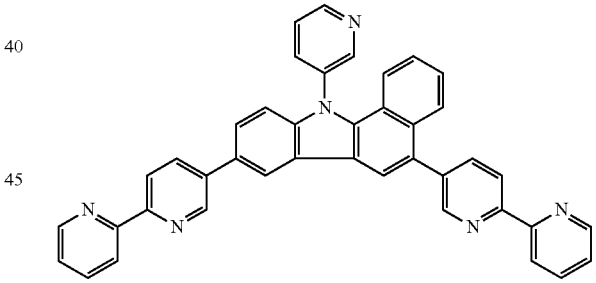
RI-12
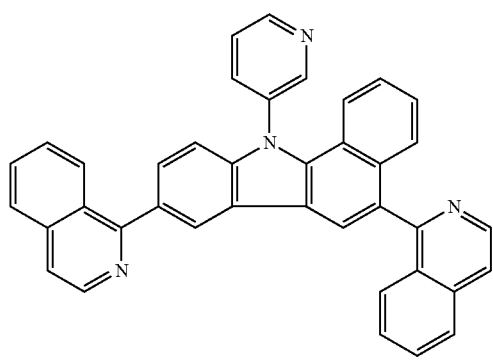
RI-16
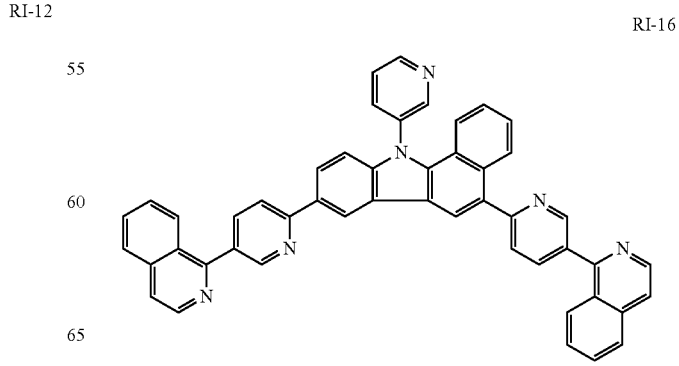

RI-17
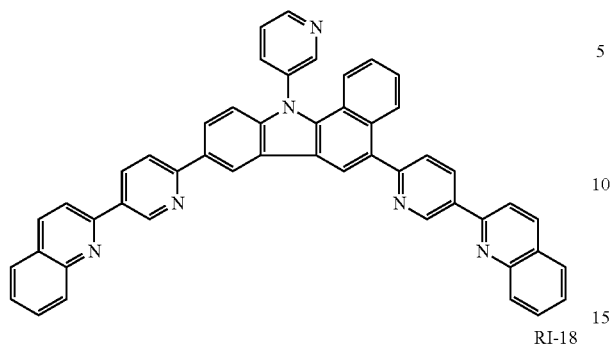
RI-18
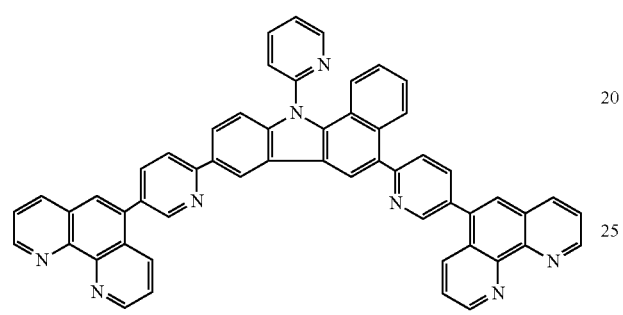
RI-19
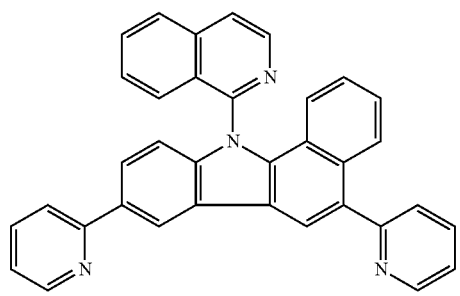
RI-20
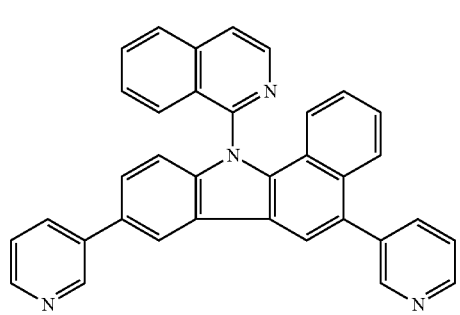
RI-21
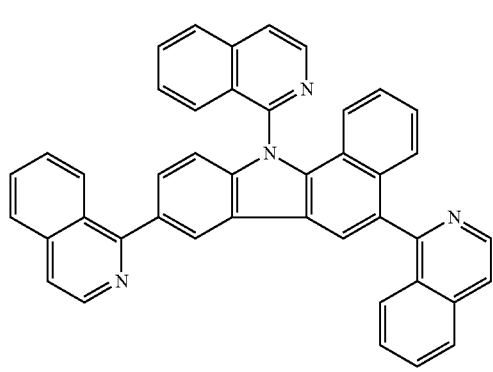
RI-22
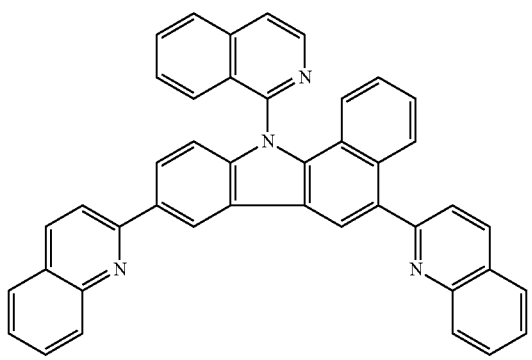
RI-23
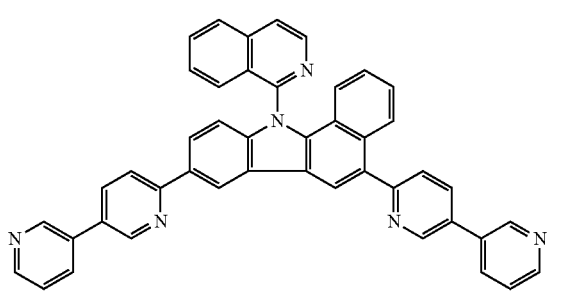
RI-24
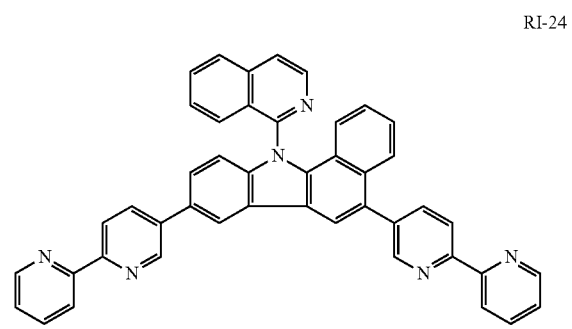
RI-25
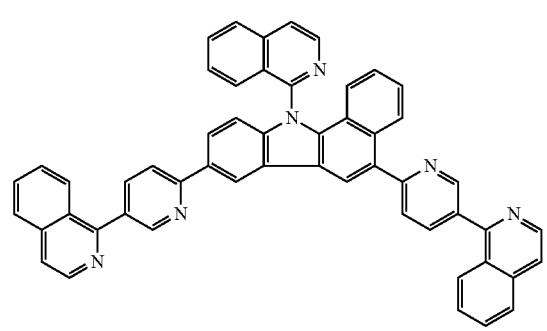

RI-26
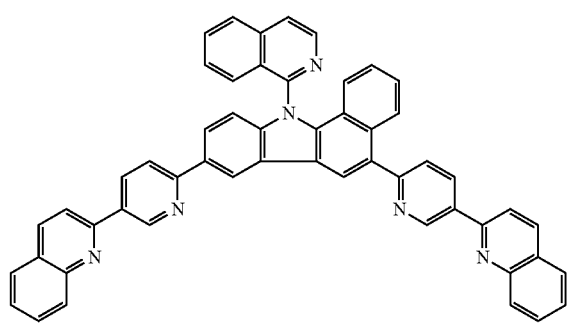
RI-27
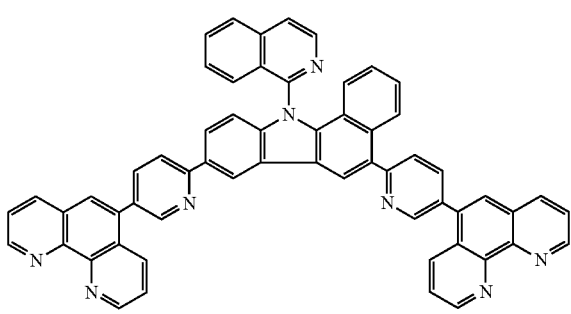
RI-28
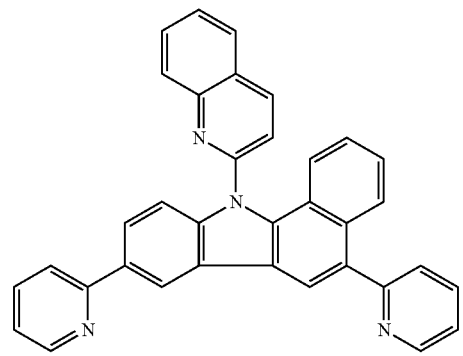
RI-29
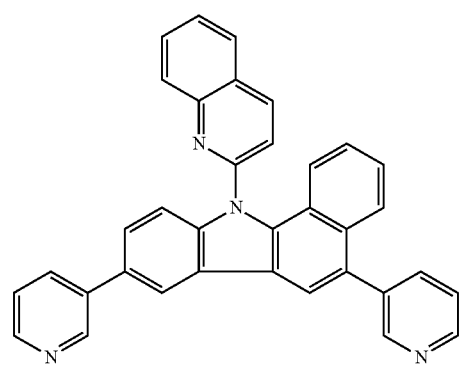
RI-30
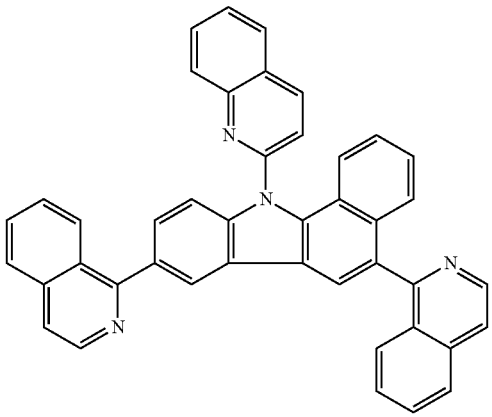
RI-31
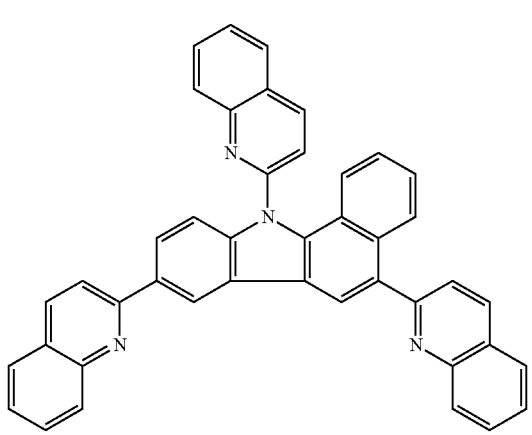
RI-32
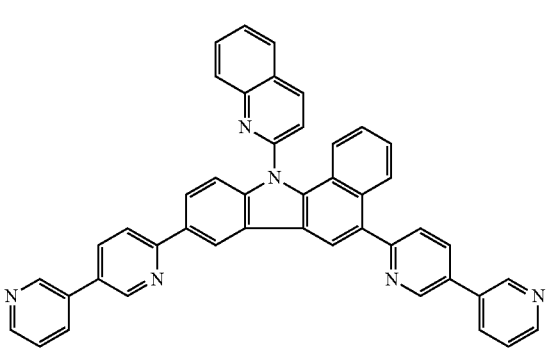
RI-33
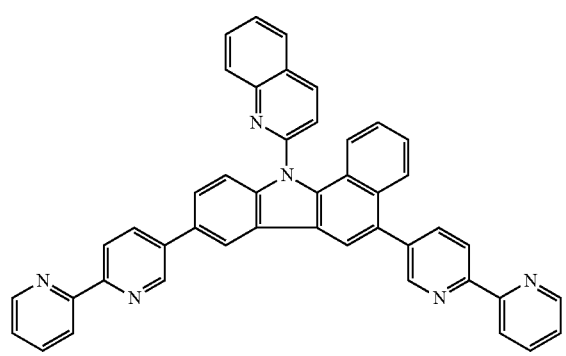

RI-34
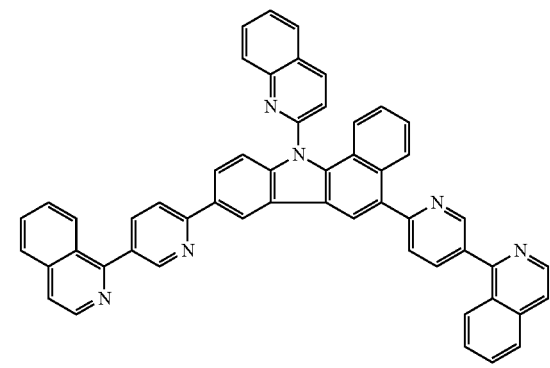
RI-35
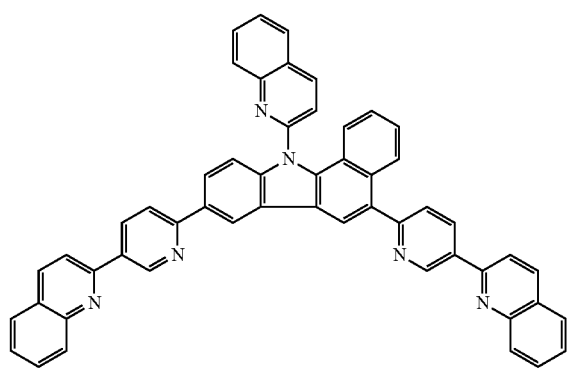
RI-36
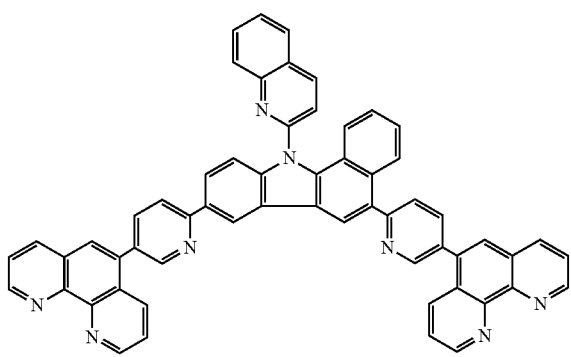
RI-37
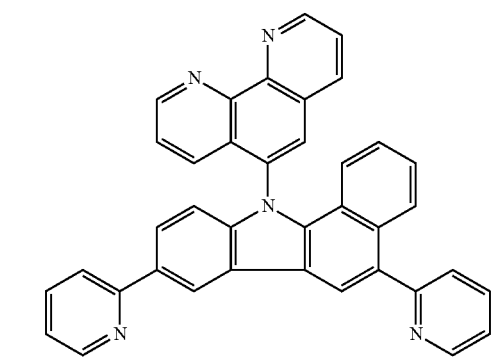
RI-38
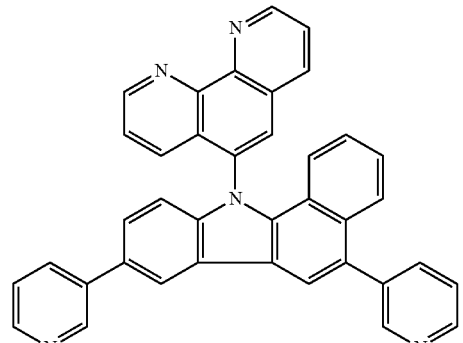
RI-39
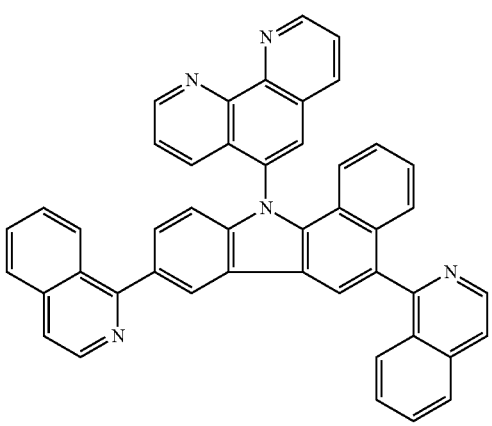
RI-40
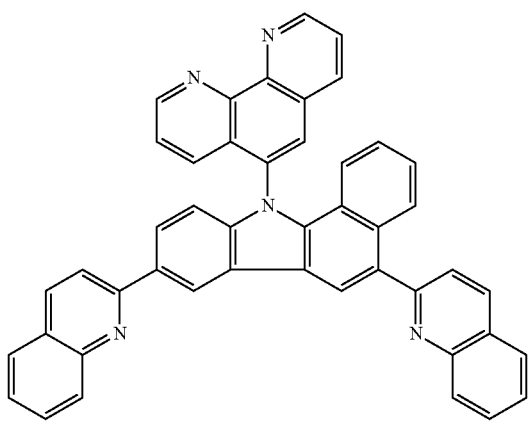
RI-41
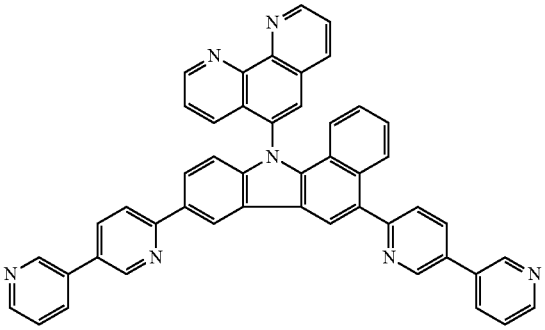

RI-42
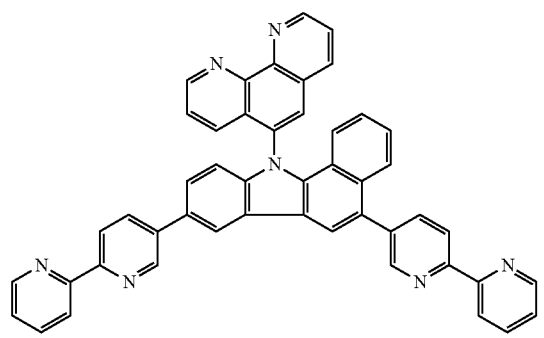
RI-43
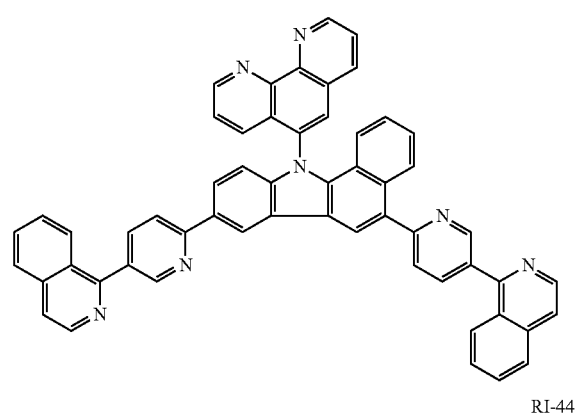
RI-44
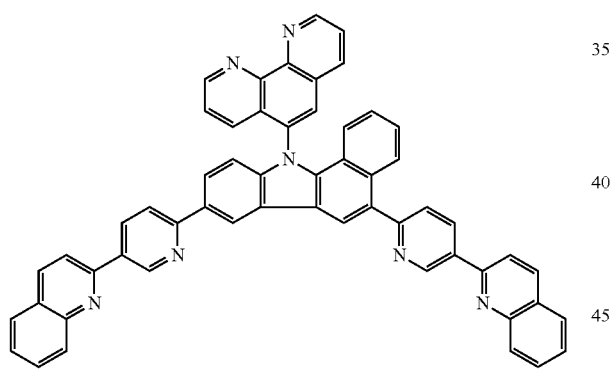
RI-45
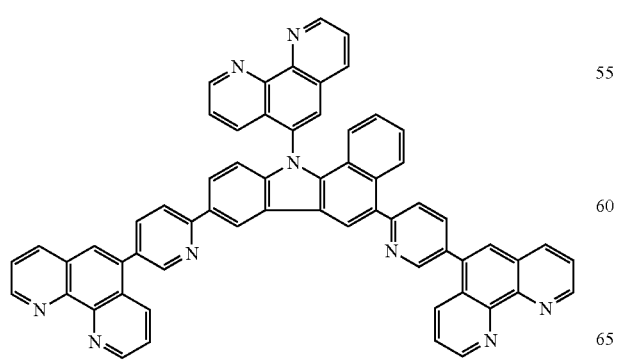
RI-46
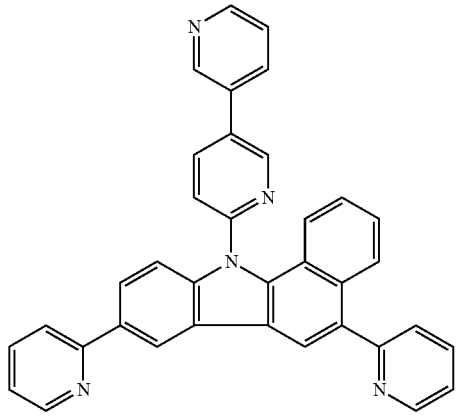
RI-47
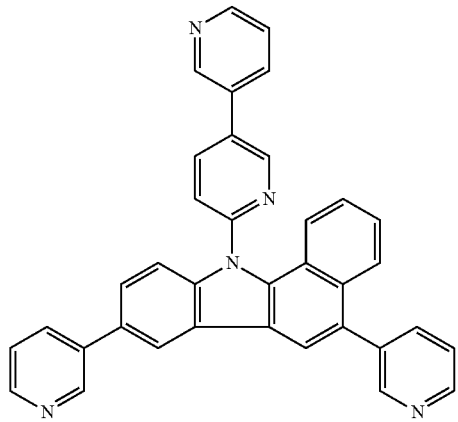
RI-48
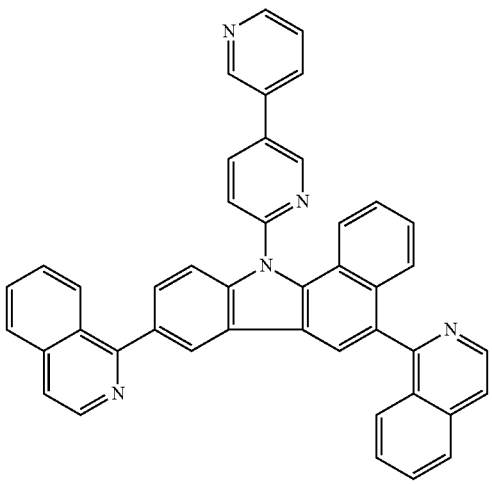

-continued
RI-49
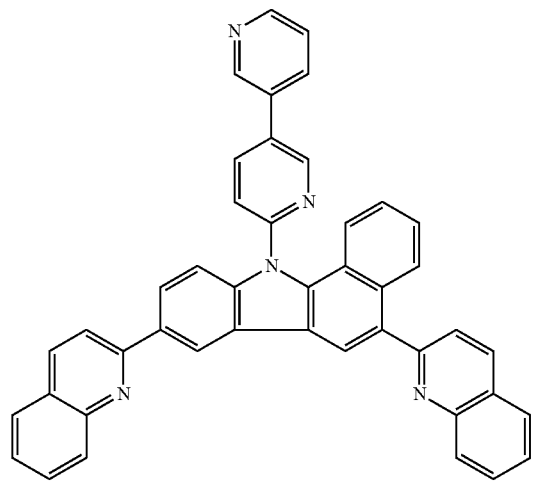
RI-50
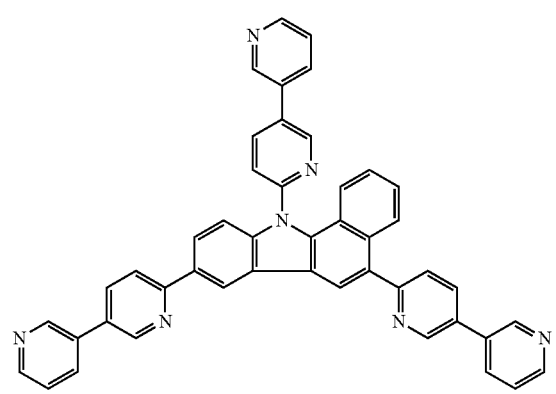
RI-51
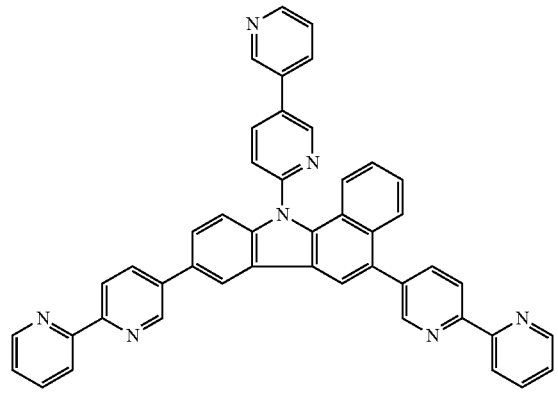
-continued
RI-52
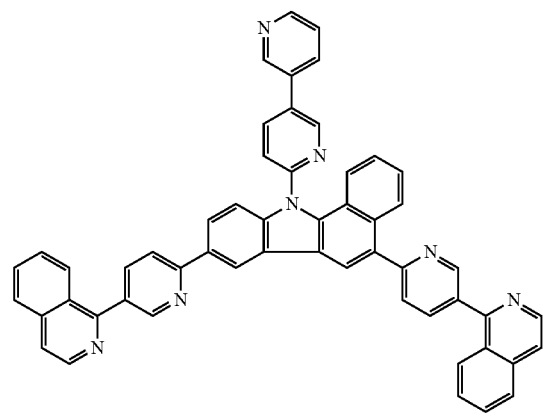
RI-53
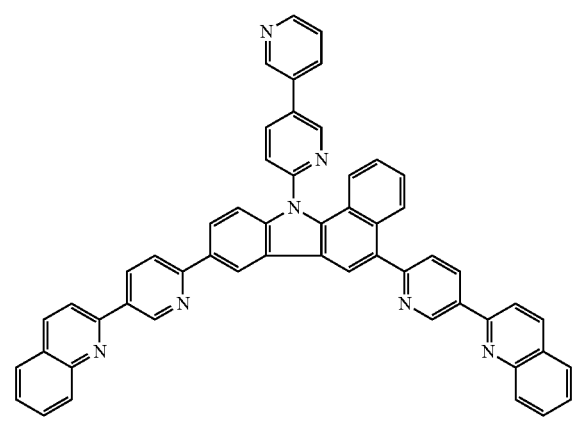
RI-54
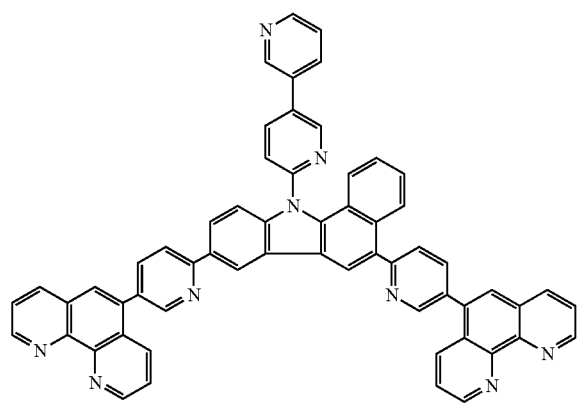

RI-55
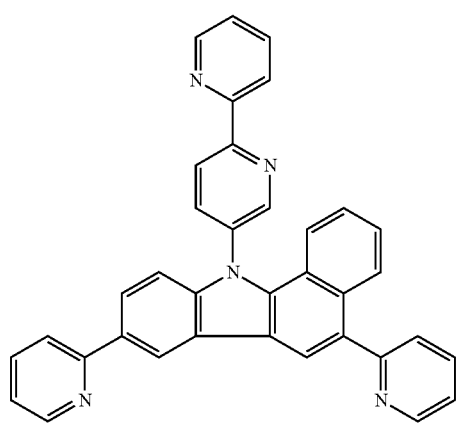
RI-58
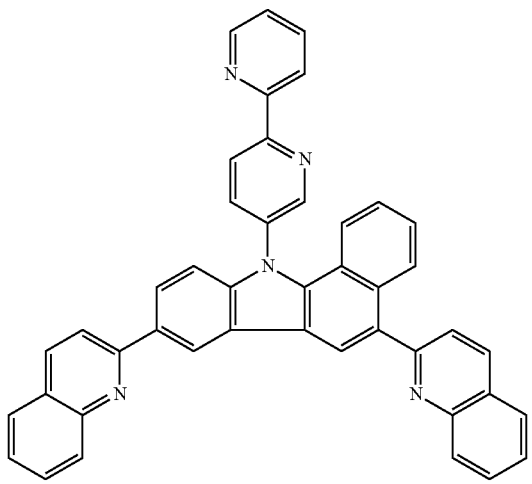
RI-56
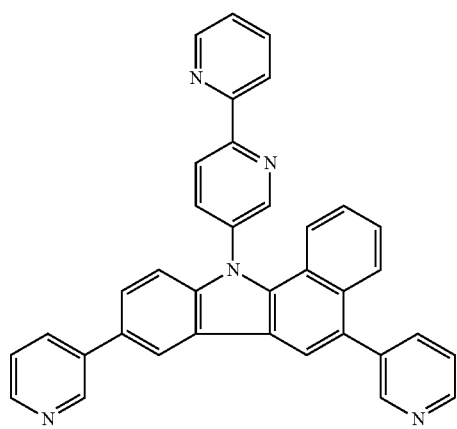
RI-59
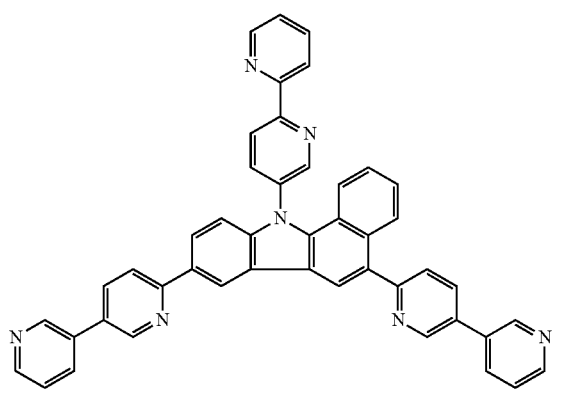
RI-57
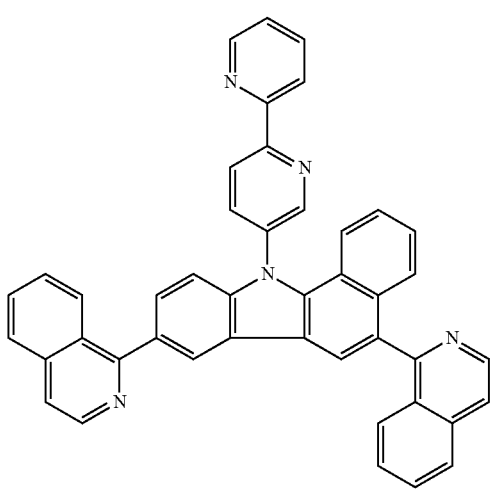
RI-60
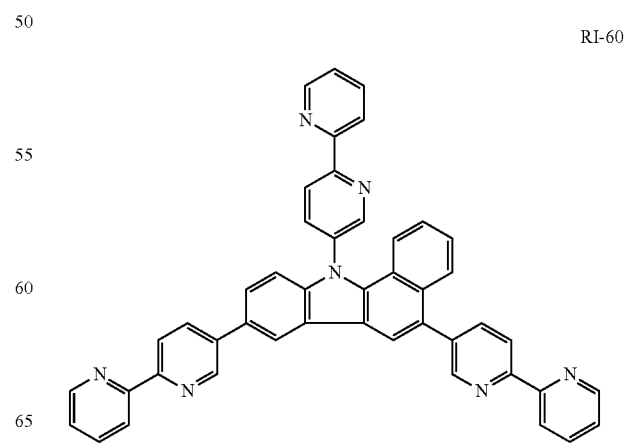

-continued
RI-61
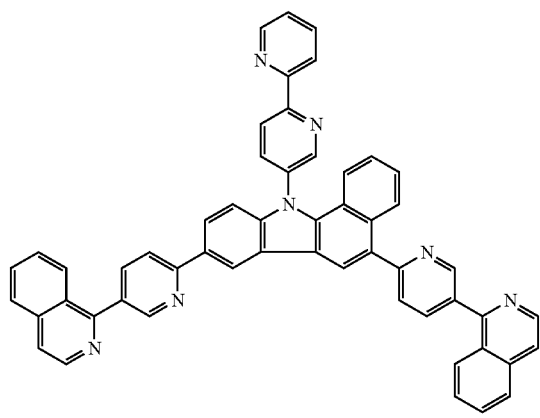
RI-62
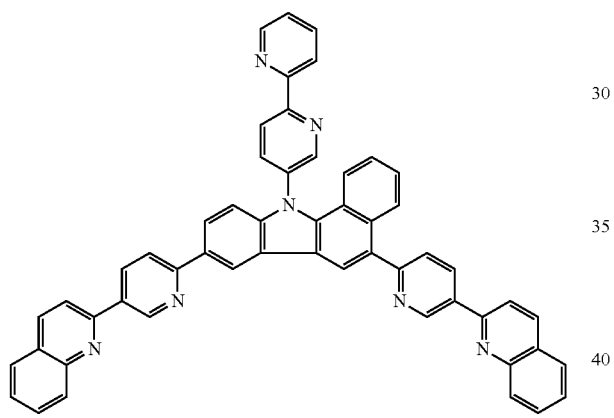
RI-63
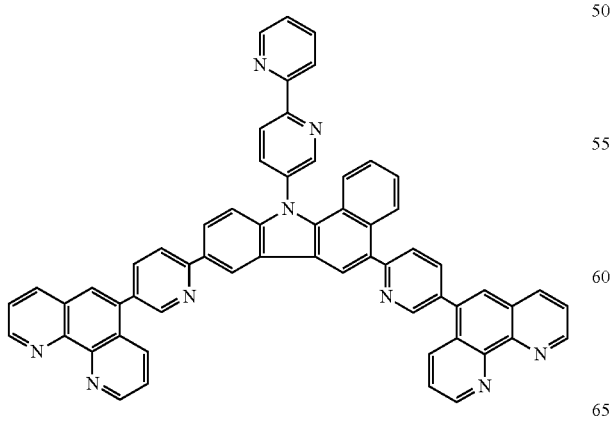
-continued
RI-64
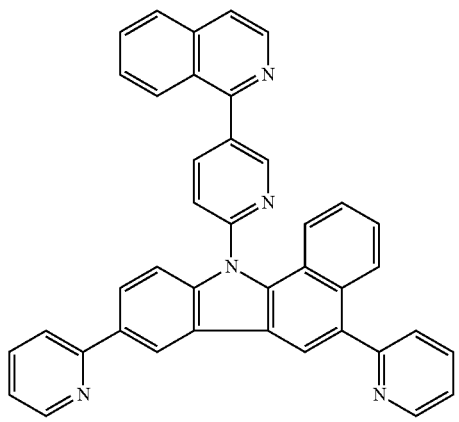
RI-65
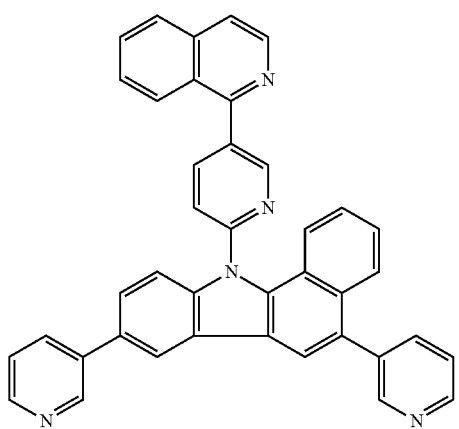
RI-66
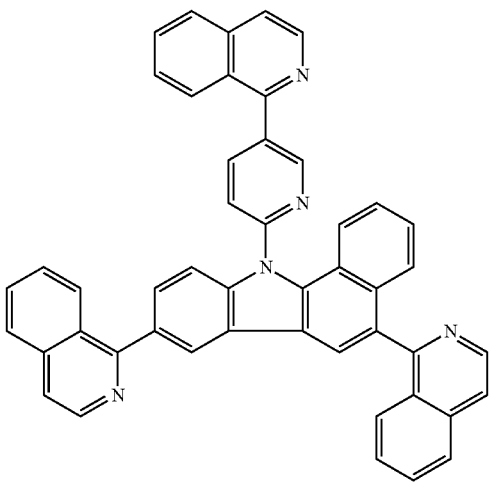

RI-67
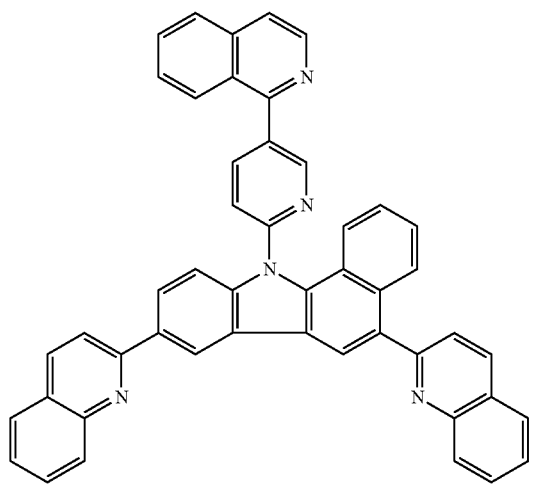
RI-68
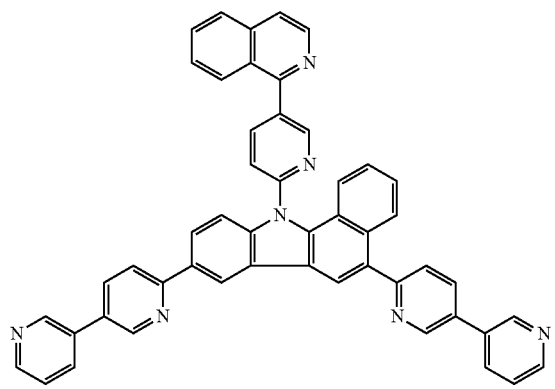
RI-69
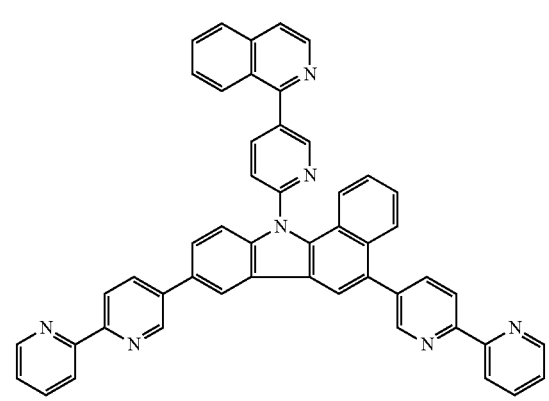
RI-70
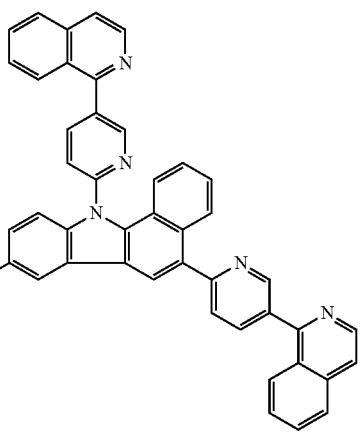
RI-71
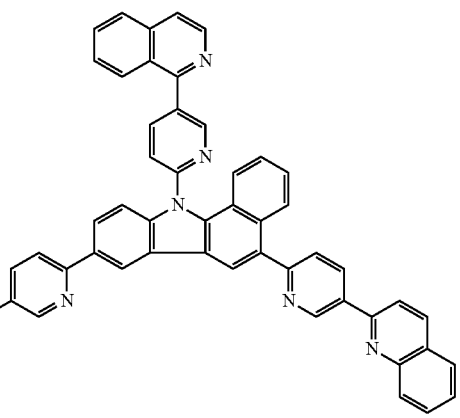
RI-72
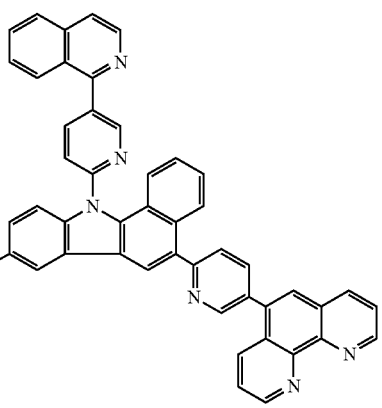

RI-73
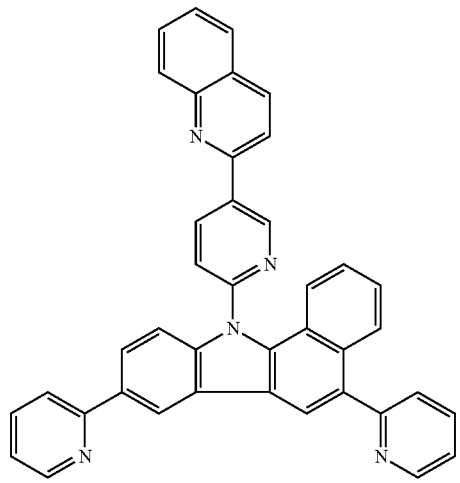
RI-74
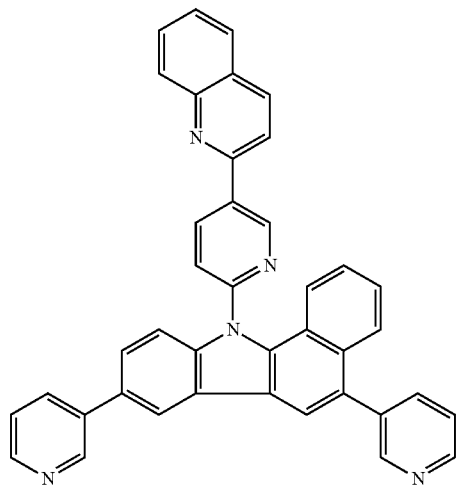
RI-75
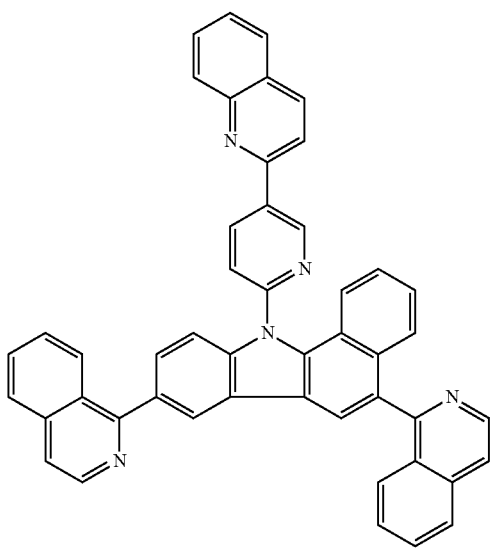
RI-76
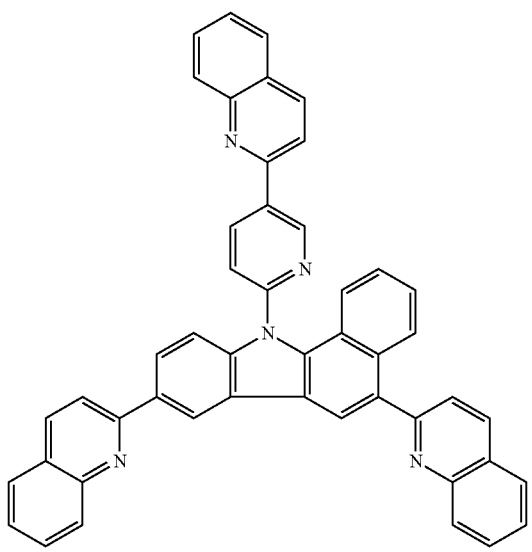
RI-77
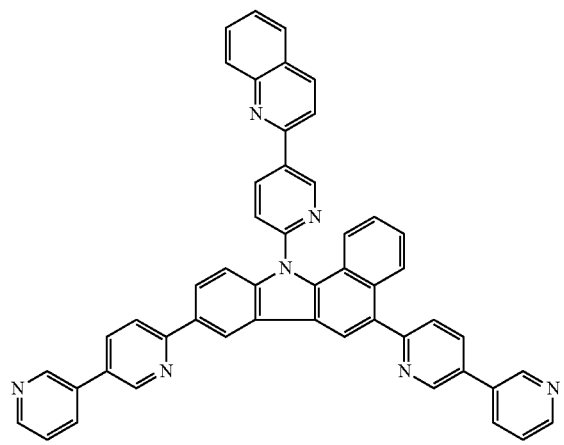
RI-78
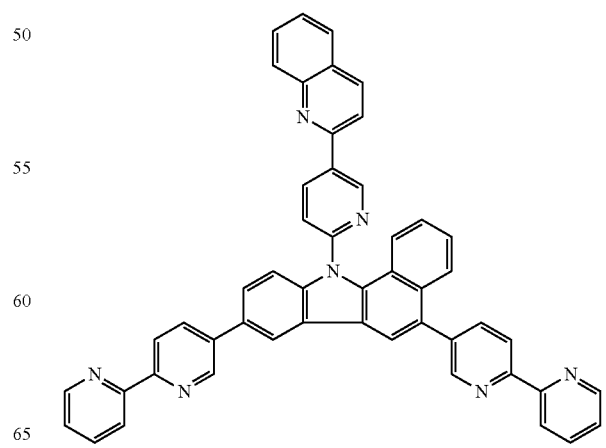

-continued
RI-79
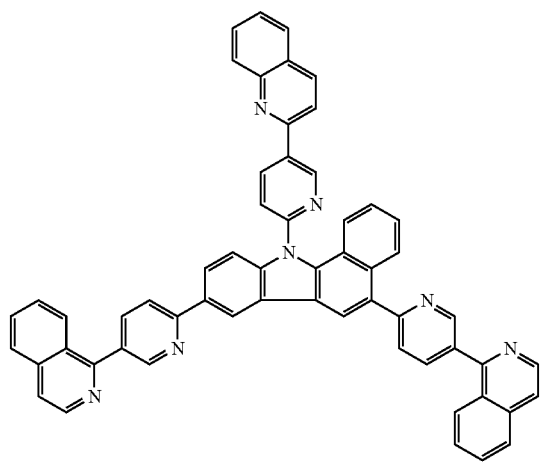
RI-80
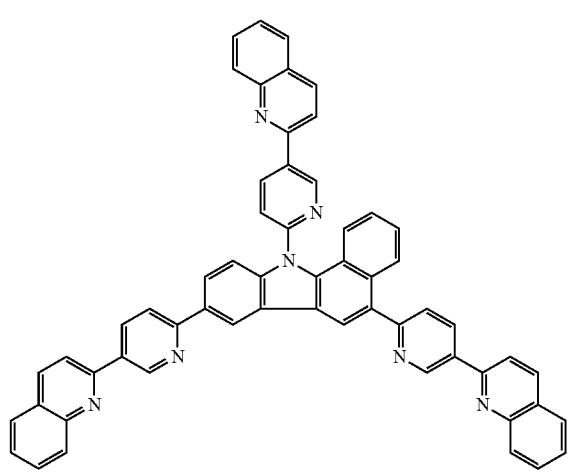
RI-81
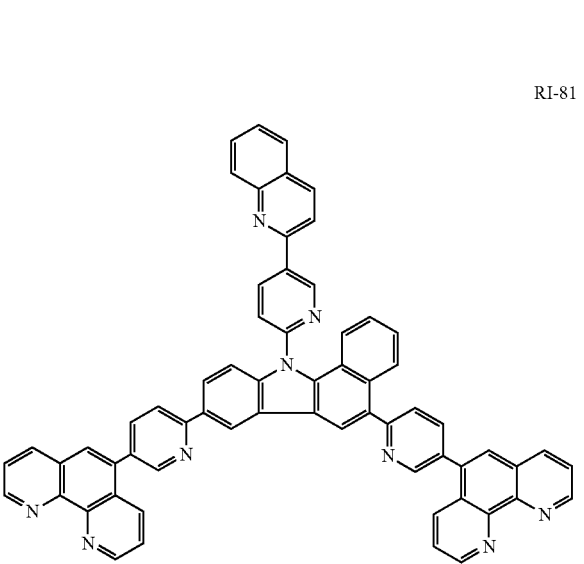
RI-82
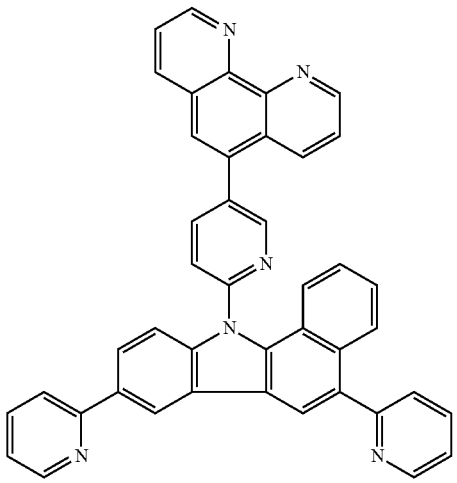
RI-83
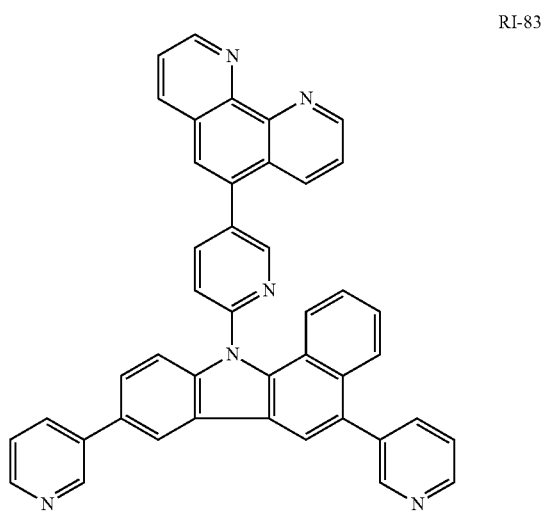
RI-84
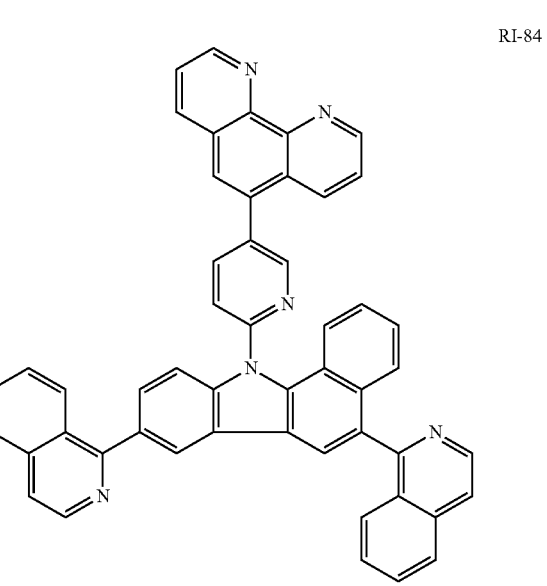

-continued

RI-85
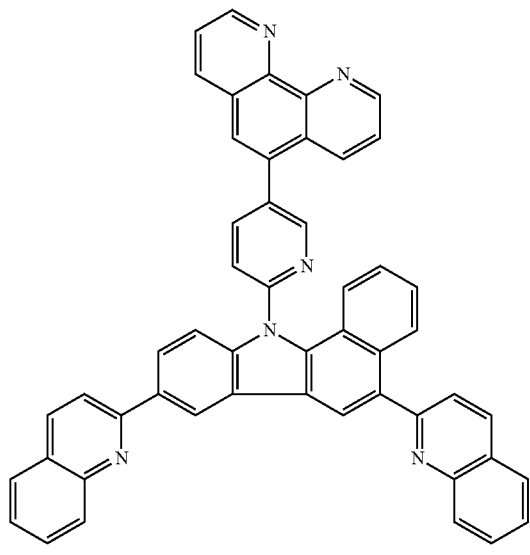

RI-86
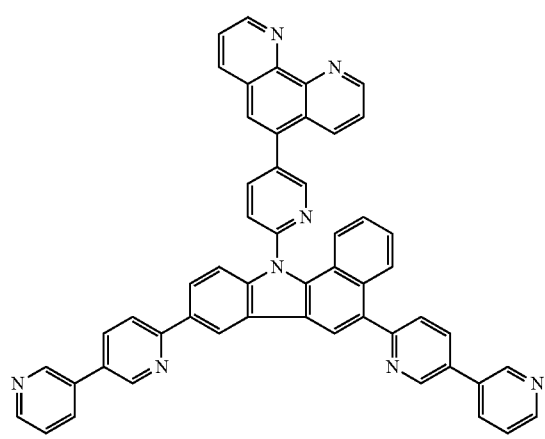

RI-87
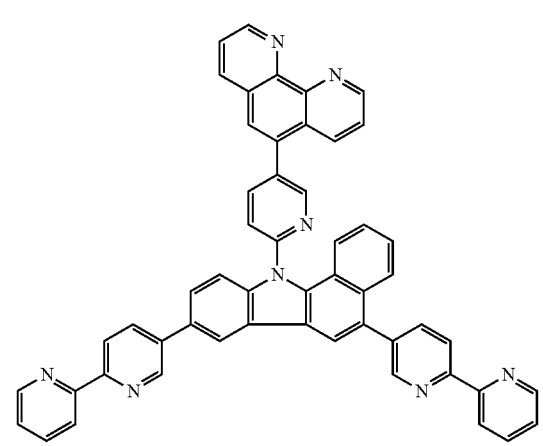

-continued

RI-88
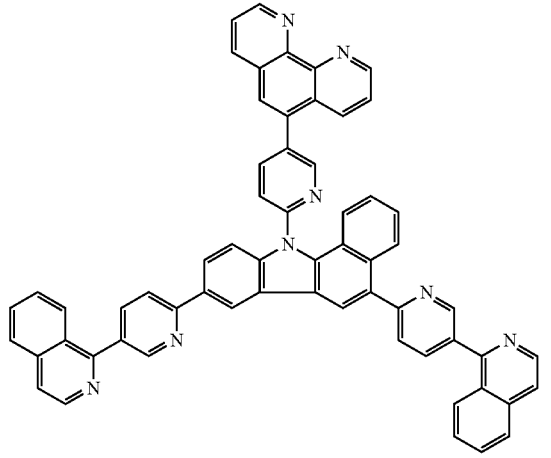

RI-89

RI-90

OLED Device

Figure 2:
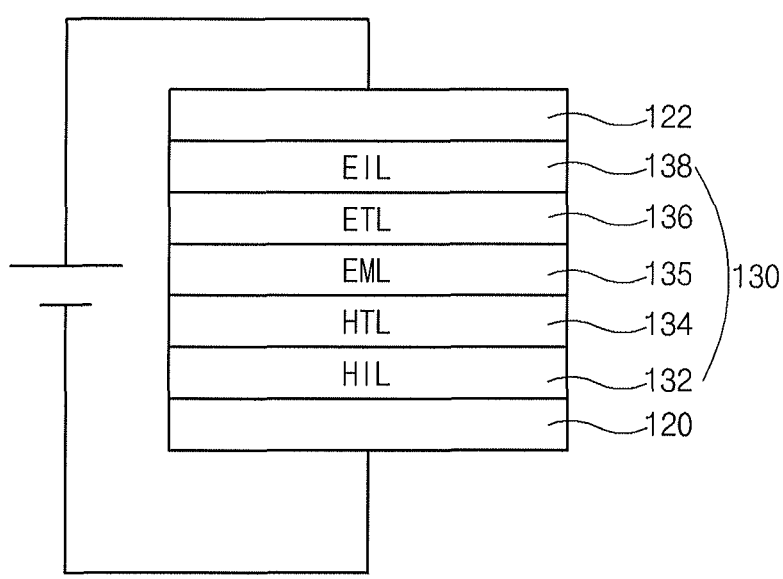
FIG. 2 is a schematic cross-sectional view of an OLED device according to an embodiment of the present invention.

The OLED device using the red phosphorescent compound of the present invention is explained with FIG. 2. FIG. 2 is a schematic cross-sectional view of an OLED device according to the present invention. Referring to FIG. 2, the OLED device 100 includes a transparent substrate (not shown), a first electrode 120 over the transparent substrate, a second electrode 122 over the first electrode 120 and an organic material layer 130 between the first and second electrodes 120 and 122.

The first and second electrodes 120 and 122 respectively serve as anode and cathode. The first electrode 120 as the anode is formed of a material having a higher work function than a material of the second electrode 122 as the cathode. The first electrode 120 has properties of efficiently injecting holes as a positive-charged carrier. In addition, the first electrode 120 may be transparent and have good conductivity. The first electrode 120 is formed of metals, mixed metals, metal alloys, mixed metal oxides or conductive polymers. For example, the first electrode 120 may be formed of one of vanadium, copper, gold, their alloys, indium-tin-oxide (ITO), indium-zinc-oxide (IZO), fluorine-doped tin oxide, $ZnO-Ga_2O_3$, $ZnO-Al_2O_3$, $SnO_2-Sb_2O_3$, carbon black, and graphene. Beneficially, the first electrode 120 may be formed of ITO.

On the other hand, the second electrode 122 over the electron injecting layer 138 has properties of efficiently injecting electrons as a negative-charged carrier. For example, the second electrode 122 may be formed of one of gold, aluminum (Al), copper, silver, their alloys, Al-calcium alloy, magnesium-silver alloy, Al-lithium alloy, Al-lithiumoxide alloy, rear-earth metals, lanthanide metals, actinide metals. Beneficially, the second electrode 122 may be formed of Al or Al-calcium alloy. A passivation layer may be formed on the second electrode 120.

Each of the first and second electrodes 120 and 122 may be formed of a vapor deposition process and have a thickness of about 5 to 400 nm.

To increase emission efficiency, the organic material layer 130 may have a multi-layered structure. For example, the organic material layer 130 may include a hole injecting layer (HIL) 132, a hole transporting layer (HTL) 134, the emitting material layer (EML) 135, the electron transporting layer (ETL) 136 and the electron injecting layer (EIL) 138. In this instance, the compound of the present invention is used for the EML 135 as a dopant.

An interfacial property between the first electrode 120 of ITO and the HTL 134 of an organic material is improved by the HIL 132 between the first electrode 120 and the HTL 134. In addition, a surface of the uneven ITO layer is planarized by the HIL 132. For example, the HIL 132 may be formed of one of copper phthalocyanine (CuPc), aromatic amines, such as 4,4',4"-tris[methylphenyl(phenyl)amino]triphenylamine (m-MTDATA), 4,4',4"-tris[1-naphthyl(phenyl)amino]triphenylamine (1-TNATA), 4,4',4"-tris[2-naphthyl(phenyl)amino]triphenylamine (2-TNATA), and 1,3,5-tris[N-(4-diphenylaminophenyl)phenylamino]benzene (p-DPA-TDAB), 4,4'-bis[N-[4-{N,N-bis(3-methylphenyl)amino}phenyl]-N-phenylamino]biphenyl (DNTPD), and hexaazatriphenylene-hexacarbonitirile (HAT-CN). The HIL 132 may have a thickness of about 10 to 100 nm.

To securely provide the holes from the first electrode 120 through the HIL 132 to the EML 135, the HTL 134 is formed of a material having highest occupied molecular orbital (HOMO) value higher than the EML 135. For example, the HTL 134 may be formed of one of N,N-bis(3-methylphenyl)-N,N-diphenyl-[1,1'-diphenyl]-4,4'-diamine (TPD), N,N'-bis(1-naphthyl)-N,N'-biphenyl-[1,1'-biphenyl]-4,4'-diamine (TPB), N,N'-bis-(1-naphyl)-N,N'-diphenyl-1,1'-biphenyl-4,4'-diamine (NPB), 1-naphtyl-N-phenyl-aminobiphenyl (NPD), triphenylamine (TPA), bis[4-(N,N-diethylamino)-2-methylphenyl](4-methylphenyl)methane (MPMP), N,N',N-tetrakis(4-methylphenyl)-(1,1'-biphenyl)-4,4-diamine (TTB), and N,N'-bis(4-methylphenyl)-N,N'-bis (4-ethylphenyl)-[1,1'-(3,3'-dimethyl)biphenyl]-4,4'-diamine (E TPD). The HTL 134 may be formed of NPB or NPD and have a thickness of about 30 to 60 nm.

The EML 135 on the HTL includes the red phosphorescent compound of the present invention. For example, the red phosphorescent compound of the present invention may be used as a host in the EML 135 to improve color purity and prevent the color shift and the quenching problem. In addition, the EML 135 may further include a dopant.

For example, iridium complex, e.g., bis(2-phenylquinoline)(acetylacetonate)iridium(III) (Ir(2-phq)2(acac), bis(2-benzo[b]thiophen-2-yl-pyridine)(acetylacetonate)iridium (III) (Ir(btp)2(acac) and tris(2-phenylquinoline)iridium(III) (Ir(2-phq)3), may be used as the dopant. The dopant may be doped with a weight % of about 0.1 to 50 of the EML 135. The EML 135 has a thickness about 5 to 200 nm, and beneficially 30 to 60 nm.

The red phosphorescent compound of the above Formula 1 and 4 includes benzo-carbazole core, which has nitrogen atom, and the heteroaromatic group substituent and/or the alicyclic group substituent, which also has nitrogen atom, such that nitrogen density in the compound is increased. As a result, the red phosphorescent compound of the present invention has an improved charge injecting property required to generate phosphorescent phenomenon. Namely, since the red phosphorescent compound includes nitrogen atom, which has good electron affinity, electron mobility and electron security in the EML 135 are improved.

In addition, since the core of the red phosphorescent compound is substituted by the heteroaromatic group and alicyclic group, each of which is substituted alkyl, alkoxy, silyl, aryl, the emitting efficiency, the lifetime and the color purity of the OLED device is remarkably improved.

Moreover, since the core of the red phosphorescent compound is substituted by the heteroaromatic group and alicyclic group, each of which is substituted alkyl, alkoxy, silyl, aryl, the red phosphorescent compound is soluble in the general organic solvent, e.g., a non-polar organic solvent. Furthermore, an interfacial property with the electrode in the OLED device is improved.

When the OLED device is fabricated by a solution process, e.g., an ink jet printing and a screen-printing, the fabricating process is simplified and process yield is improved without a vacuum deposition process and a photolithography process. In addition, the solution process is adequate to a large-size OLED device fabricating process and a flexible substrate. Moreover, wasted material in the solution process is minimized in comparison to the deposition process such that production costs are decreased.

The EIL 138 and ETL 136 are formed between the EML 135 and the second electrode 122. The EIL 138 may be formed of one of LiF, $BaF_2$ and CsF. The ETL 136 is formed of a material having relatively high electron mobility. For example, the ETL 136 may be formed of one of tris(8-hydroxyquinolinato)aluminum (Alq3), 9-dimethyl-4,7-diphenyl-1,10-phenanthroline (DDPA), 2-(4-biphenyl)-5-(4-tert-butyl)-1,3,4-oxadiazole (PBD), 3-(4-biphenyl)-4-phenyl-5-(4-tert-butyl)-1,2,4-triazole (TAZ) and phenylquinozaline. The ETL 136 may have a thickness of about 5 to 150 nm.

Although not shown, a hole blocking layer (HBL) of a material having a relatively low HOMO level may be formed between the EML 135 and the ETL 136. For example, the HBL may be formed of one of 2,9-dimethyl-4,7-diphenyl-1,10-phenanthroline (BCP) and have a thickness of about 5 to 50 nm.

Hereinafter, synthesis of the red phosphorescent compound of the present invention is explained. However, the synthesis of the red phosphorescent compound of the present invention is not limited thereto.

SYNTHESIS 1

1. Synthesis of RH-04 Compound
1) dihydrobenzo[3,4]carbazole
Dihydrobenzo[3,4]carbazole was synthesized by following Reaction Formula 1-1.

[Reaction Formula 1-1]

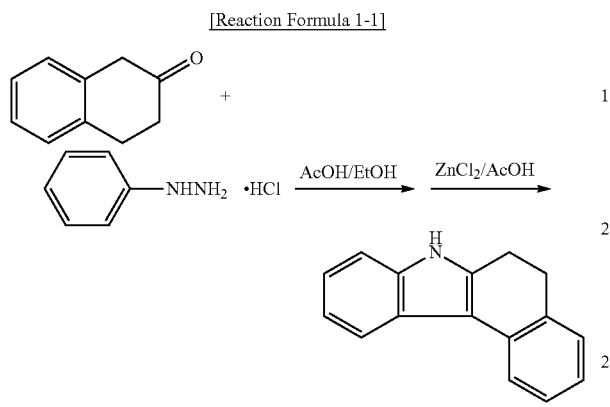

β-teralone (25 g, 0.17 mol), phenylhydrazinuim chloride (24.7 g, 0.17 mol) and acetic acid were put in ethanol in a two-round flask and refluxed for about 1 hour. The solution was cooled into a room temperature, filtered and evaporated to remove the solvent. Zinc chloride (58 g, 0.42 mol) and acetic acid were added into the resultant and refluxed for about 30 minutes. The resulting solution was cooled in to a room temperature and evaporated to remove the solvent. The resultant was precipitated with MC/PE to obtain dihydrobenzo[3,4]carbazole (30 g, yield: 80%).

2) benzo[3,4]carbazole
Benzo[3,4]carbazole was synthesized by following Reaction Formula 1-2.

[Reaction Formula 1-2]

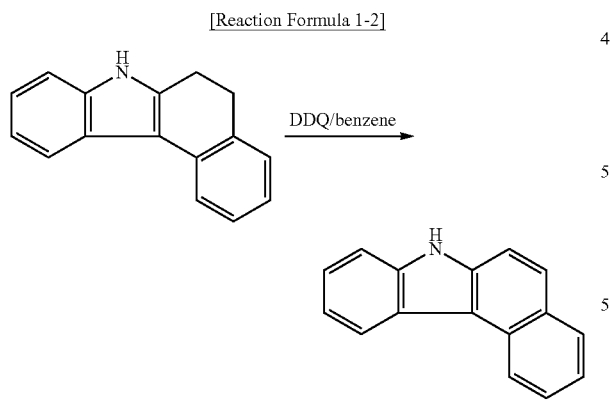

Dihydrobenzo[3,4]carbazole (20 g, 0.09 mol), 2,3-dichloro-5,6-dicyanobenzoquinone (24.6 g, 0.11 mol) and benzene were put in a two-round flask and stirred at a room temperature and for about 3 hours. The solution was extracted with ethyl acetate and evaporated to remove the solvent. The resultant were purified by a silica-gel column to obtain benzo[3,4]carbazole (17.6 g, yield: 90%).

3) 9-2'-pyridylbenzo[3,4]carbazole
9-2'-pyridylbenzo[3,4]carbazole was synthesized by following Reaction Formula 1-3.

[Reaction Formula 1-3]

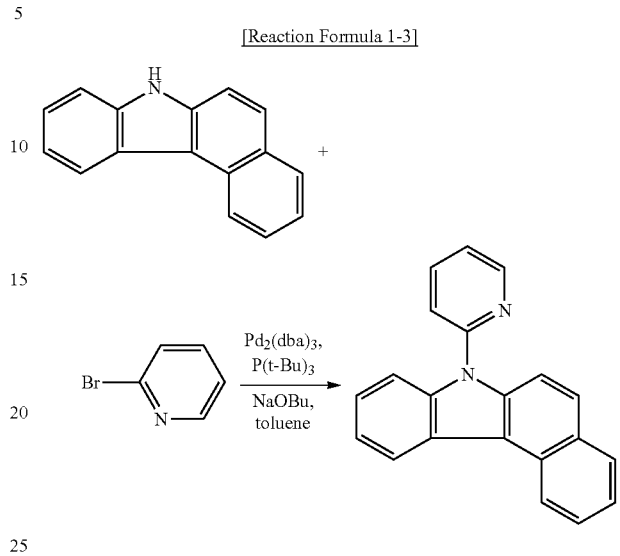

Benzo[3,4]carbazole (5 g, 0.02 mol), 2-bromopyridine (4 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-2'-pyridylbenzo[3,4]carbazole (6 g, yield: 90%).

4) 9-2'-pyridyl-6-bromobenzo[3,4]carbazole
9-2'-pyridyl-6-bromobenzo[3,4]carbazole was synthesized by following Reaction Formula 1-4.

[Reaction Formula 1-4]

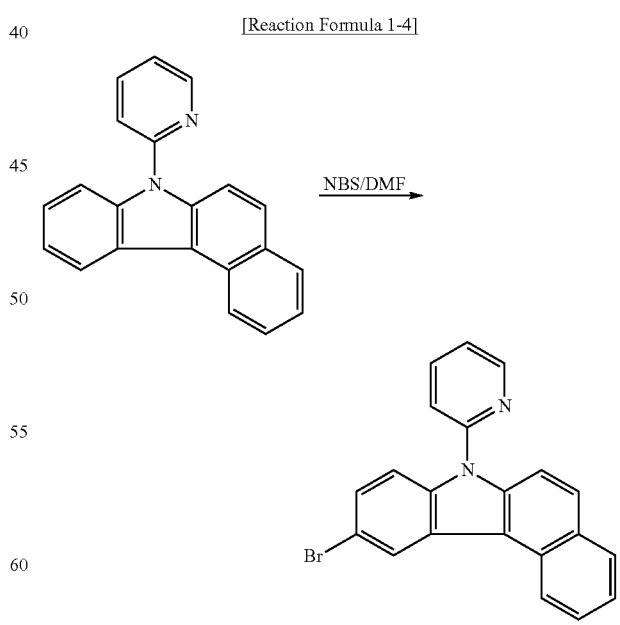

9-2'-pyridylbenzo[3,4]carbazole (6 g, 0.02 mol) and DMF were put in a two-round flask. NBS (3.8 g, 0.021 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 9-2'-pyridyl-6-bromobenzo[3,4]carbazole (7.4 g, yield: 80%).

5) 6-2'-quinolyl-9-2'-pyridylbenzo[3,4]carbazole (RH-04 compound)

RH-04 compound was synthesized by following Reaction Formula 1-5.

[Reaction Formula 1-5]

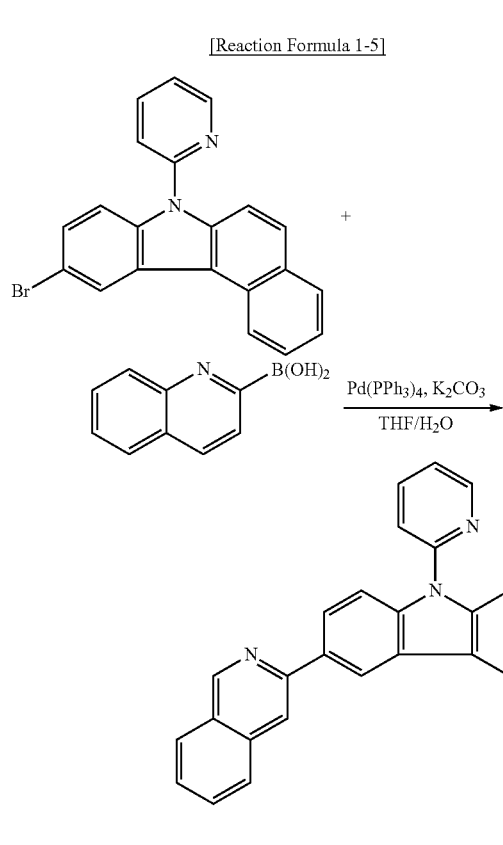

9-2'-pyridyl-6-bromobenzo[3,4]carbazole (2 g, 5.3 mol), 2-quinolineboronic acid (1.0 g, 5.4 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 6-2'-quinolyl-9-2'-pyridylbenzo[3,4]carbazole (RH-04 compound) (1.7 g, yield: 70%).

2. Synthesis of RH-13 Compound 1) 9-3'-pyridylbenzo[3,4]carbazole 9-3'-pyridylbenzo[3,4]carbazole was synthesized by following Reaction Formula 2-1.

[Reaction Formula 2-1]

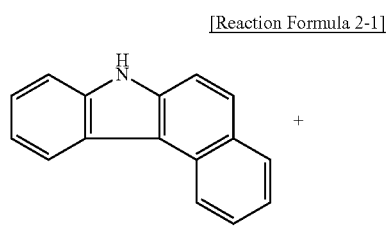

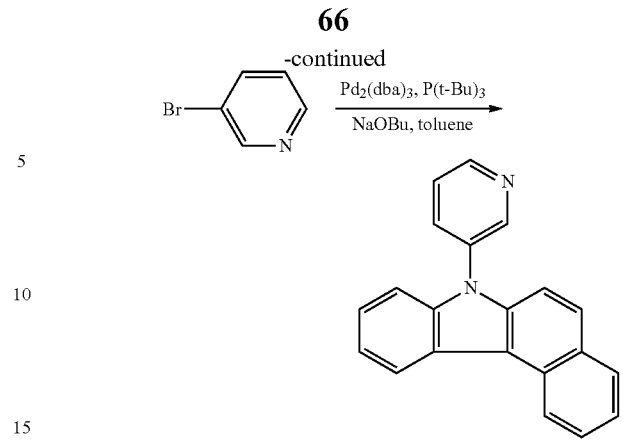

Benzo[3,4]carbazole (5 g, 0.02 mol), 3-bromopyridine (4 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-3'-pyridylbenzo[3,4]carbazole (6 g, yield: 90%).

2) 9-3'-pyridyl-6-bromobenzo[3,4]carbazole 9-3'-pyridyl-6-bromobenzo[3,4]carbazole was synthesized by following Reaction Formula 2-2.

[Reaction Formula 2-2]

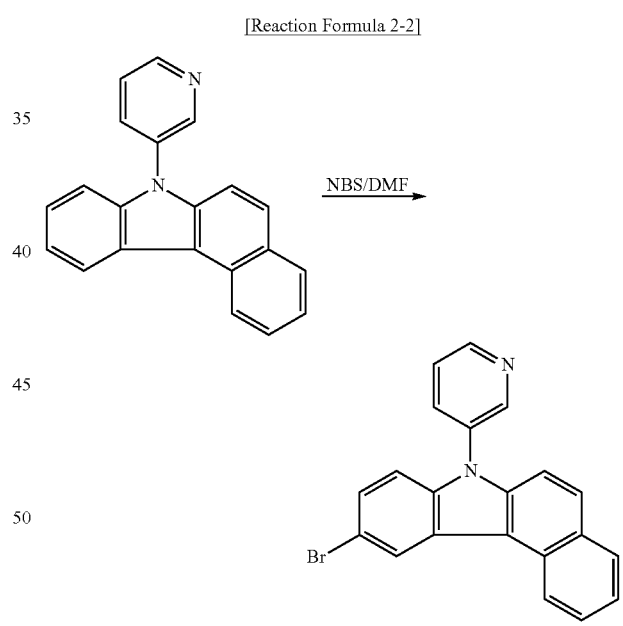

9-3'-pyridylbenzo[3,4]carbazole (6 g, 0.02 mol) and DMF were put in a two-round flask. NBS (3.8 g, 0.021 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 9-3'-pyridyl-6-bromobenzo[3,4]carbazole (7.4 g, yield: 80%).

3) 6-2'-quinolyl-9-3'-pyridylbenzo[3,4]carbazole (RH-13 compound)

RH-13 compound was synthesized by following Reaction Formula 2-3.

[Reaction Formula 2-3]

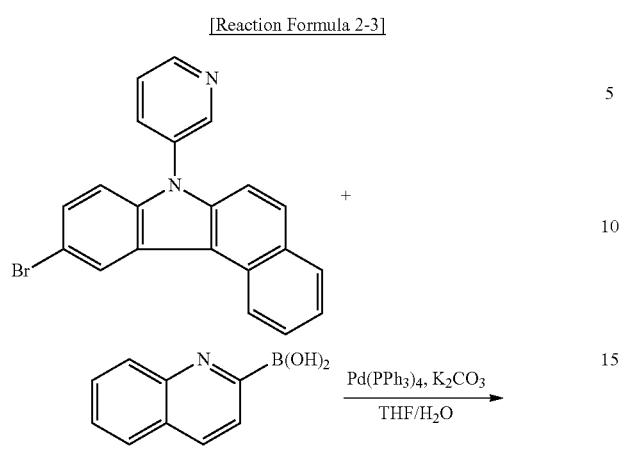

9-3'-pyridyl-6-bromobenzo[3,4]carbazole (2 g, 5.3 mol), 2-quinolineboronic acid (1.0 g, 5.4 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 6-2'-quinolyl-9-3'-pyridylbenzo[3,4]carbazole (RH-13 compound) (1.7 g, yield: 70%).

3. Synthesis of RH-49 Compound 1) 9-2'-pyridyl-4'-3''-pyridinebenzo[3,4]carbazole 9-2'-pyridyl-4'-3''-pyridinebenzo[3,4]carbazole was synthesized by following Reaction Formula 3-1.

[Reaction Formula 3-1]

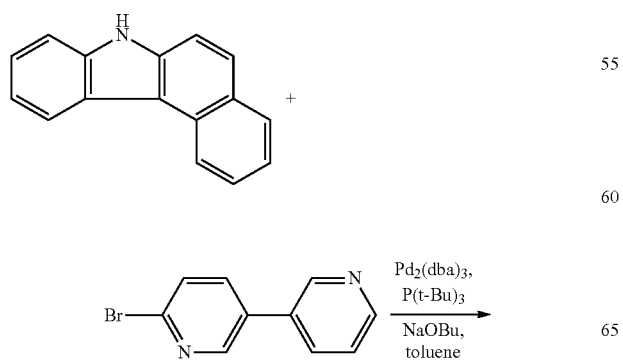

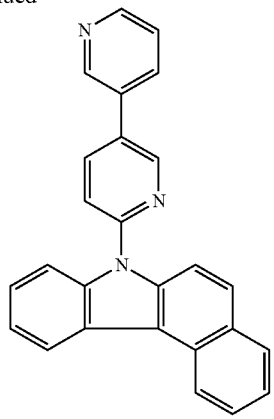

Benzo[3,4]carbazole (5 g, 0.02 mol), 2-bromopyridyl-5-3'-pyridine (8.1 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-2'-pyridyl-4'-3''-pyridinebenzo[3,4]carbazole (6 g, yield: 80%).

2) 6-bromo-9-2'-pyridyl-4'-3''-pyridinebenzo[3,4]carbazole 6-bromo-9-2'-pyridyl-4'-3''-pyridinebenzo[3,4]carbazole was synthesized by following Reaction Formula 3-2.

[Reaction Formula 3-2]

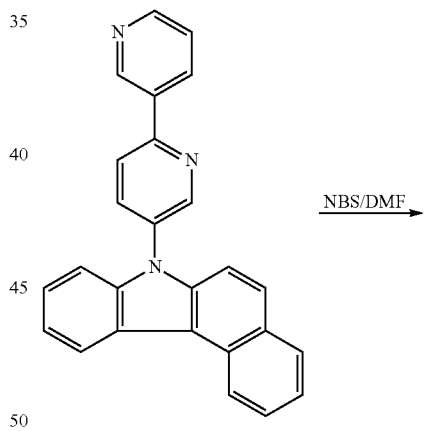

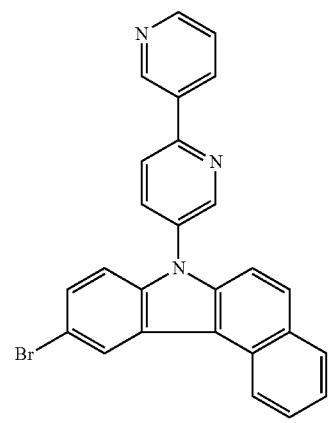

9-2'-pyridyl-4'-3"-pyridinebenzo[3,4]carbazole (6 g, 0.02 mol) and DMF were put in a two-round flask. NBS (3.8 g, 0.021 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 6-bromo-9-2'-pyridyl-4'-3"-pyridinebenzo[3,4]carbazole (5.7 g, yield: 80%).

3) 6-quinolyl-9-2'-pyridyl-4'-3"-pyridinebenzo[3,4]carbazole (RH-49)

RH-49 compound was synthesized by following Reaction Formula 3-3.

[Reaction Formula 3-3]

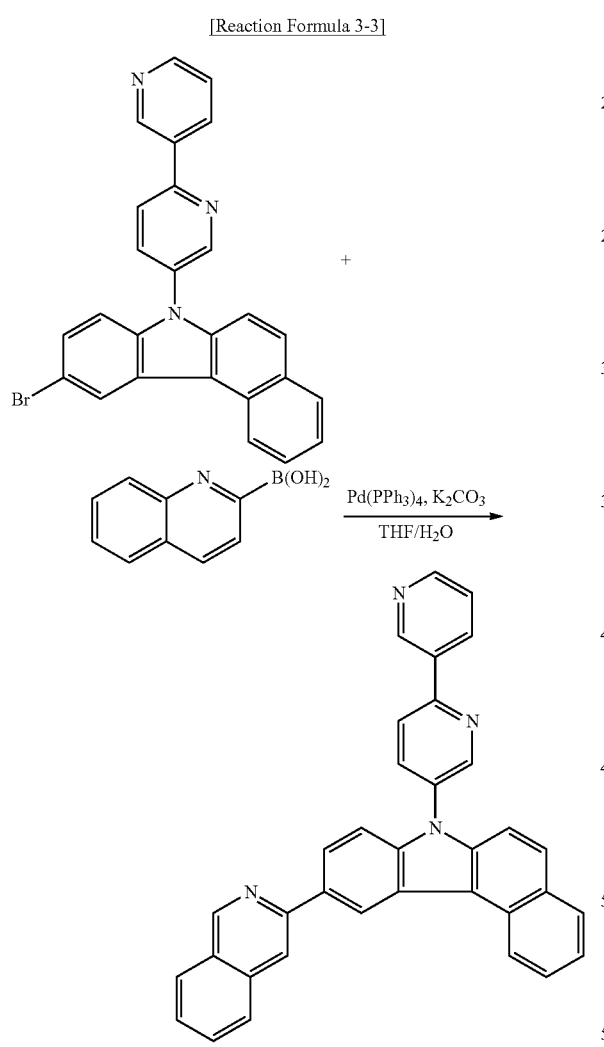

6-bromo-9-2'-pyridyl-4'-3"-pyridinebenzo[3,4]carbazole (2 g, 4.4 mol), 2-quinolineboronic acid (0.9 g, 5.3 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 6-quinolyl-9-2'-pyridyl-4'-3"-pyridinebenzo[3,4]carbazole (RH-49) (1.5 g, yield: 70%).

4. Synthesis of RH-58 Compound 1) 9-3'-pyridyl-4'-2"-pyridinebenzo[3,4]carbazole 9-3'-pyridyl-4'-2"-pyridinebenzo[3,4]carbazole was synthesized by following Reaction Formula 4-1.

[Reaction Formula 4-1]

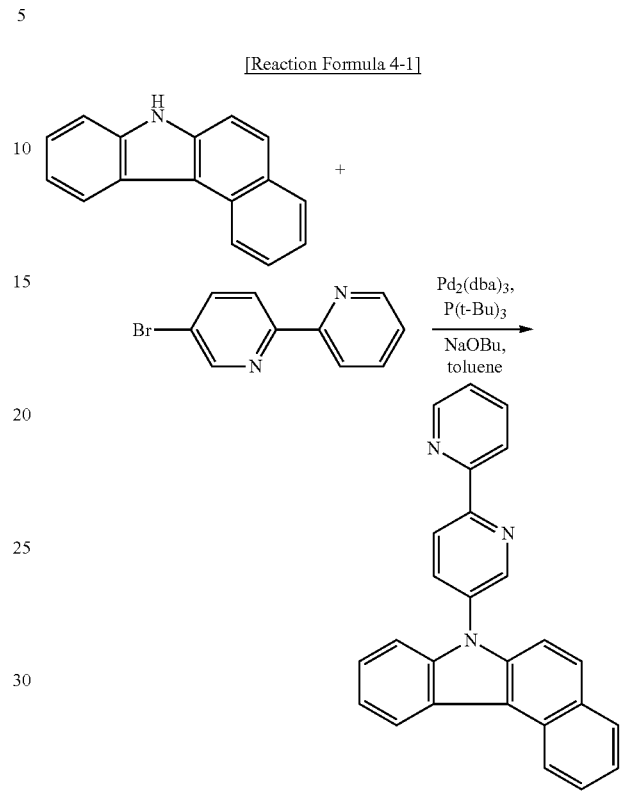

Benzo[3,4]carbazole (5 g, 0.02 mol), 3-bromopyridyl-6-2'-pyridine (8.1 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-3'-pyridyl-4'-2"-pyridinebenzo[3,4]carbazole (6 g, yield: 80%).

2) 6-bromo-9-3'-pyridyl-4'-2"-pyridinebenzo[3,4]carbazole 6-bromo-9-3'-pyridyl-4'-2"-pyridinebenzo[3,4]carbazole was synthesized by following Reaction Formula 4-2.

[Reaction Formula 4-2]

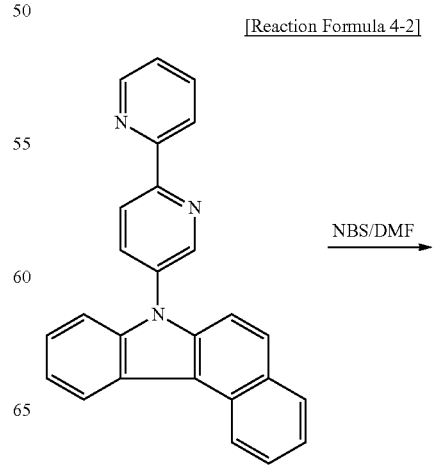

-continued

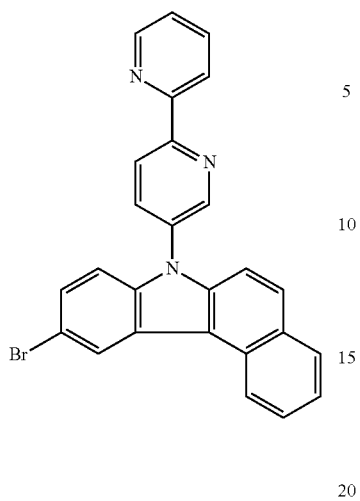

9-3'-pyridyl-4'-2"-pyridinebenzo[3,4]carbazole (6 g, 0.02 mol) and DMF were put in a two-round flask. NBS (3.8 g, 0.021 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 6-bromo-9-3'-pyridyl-4'-2"-pyridinebenzo[3,4]carbazole (5.7 g, yield: 80%).

3) 6-quinolyl-9-3'-pyridyl-4'-2"-pyridinebenzo[3,4]carbazole (RH-58)

RH-58 compound was synthesized by following Reaction Formula 4-3.

[Reaction Formula 4-3]

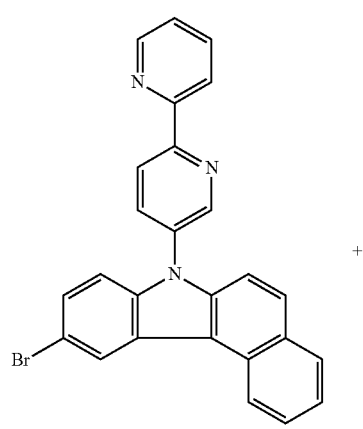

+

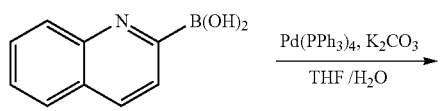

-continued

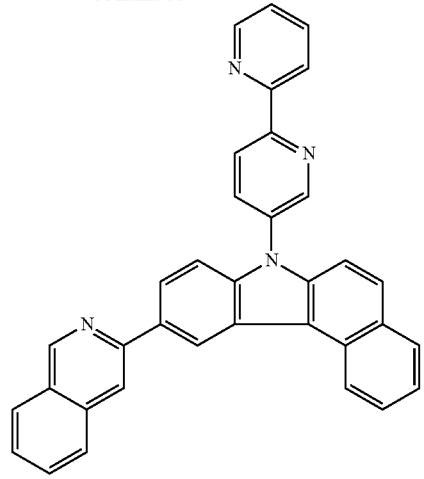

6-bromo-9-3'-pyridyl-5'-3"-pyridinebenzo[3,4]carbazole (2 g, 4.4 mol), 2-quinolineboronic acid (0.9 g, 5.3 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 6-quinolyl-9-3'-pyridyl-4'-3"-pyridinebenzo[3,4]carbazole (RH-58) (1.5 g, yield: 70%).

EXAMPLE 1

OLED Device Using RH-04 Compound as a Host

An ITO layer is deposited on a substrate and washed. The substrate is loaded in a vacuum chamber, and CuPC (650 Å), NPB (400 Å), an emitting material layer (200 Å) of RH-04 and (Ir(btp)2(acac) (5%), Alq3 (350 Å), LiF (5 Å), and Al (1000 Å) are sequentially formed.

The emitting diode produces a brightness of 1170 cd/m$^2$ at an electric current of 0.9 mA and a voltage of 6.0 V and has the CIE(x) and CIE(y) of 0.648 and 0.339, respectively.

EXAMPLE 2

OLED Device Using RH-13 Compound as a Host

An ITO layer is deposited on a substrate and washed. The substrate is loaded in a vacuum chamber, and CuPC (650 Å), NPB (400 Å), an emitting material layer (200 Å) of RH-13 and (Ir(btp)2(acac) (5%), Alq3 (350 Å), LiF (5 Å), and Al (1000 Å) are sequentially formed.

The emitting diode produces a brightness of 1185 cd/m$^2$ at an electric current of 0.9 mA and a voltage of 5.5 V and has the CIE(x) and CIE(y) of 0.650 and 0.340, respectively.

EXAMPLE 3

OLED Device Using RH-49 Compound as a Host

An ITO layer is deposited on a substrate and washed. The substrate is loaded in a vacuum chamber, and CuPC (650 Å), NPB (400 Å), an emitting material layer (200 Å) of RH-49 and (Ir(btp)2(acac) (5%), Alq3 (350 Å), LiF (5 Å), and Al (1000 Å) are sequentially formed.

The emitting diode produces a brightness of 1250 cd/m² at an electric current of 0.9 mA and a voltage of 5.3 V and has the CIE(x) and CIE(y) of 0.649 and 0.336, respectively.

EXAMPLE 4

OLED Device Using RH-58 Compound as a Host

An ITO layer is deposited on a substrate and washed. The substrate is loaded in a vacuum chamber, and CuPC (650 Å), NPB (400 Å), an emitting material layer (200 Å) of RH-58 and (Ir(btp)2(acac) (5%), Alq3 (350 Å), LiF (5 Å), and Al (1000 Å) are sequentially formed.

The emitting diode produces a brightness of 1231 cd/m² at an electric current of 0.9 mA and a voltage of 5.4 V and has the CIE(x) and CIE(y) of 0.651 and 0.331, respectively.

EXAMPLE 5

OLED Device Using RH-58 Compound as a Host (Solution Process)

An ITO layer is deposited on a substrate and washed to form an anode. The substrate is loaded in a vacuum chamber, and a hole injecting layer (800 Å) of PEDOT:PSS (spin coating: 3000 rpm, baking condition: 120° C. for 1 hr) and an emitting material layer (250 Å) of RH-58 and (Ir(btp)2 (acac) (2%) (spin coating: 3000 rpm, baking condition: 100° C. for 30 min) are coated. Alq3 (350 Å), LiF (5 Å), and Al (1000 Å) are sequentially formed on the emitting material layer.

The emitting diode produces a brightness of 762 cd/m² at an electric current of 0.9 mA and a voltage of 6.5 V and has the CIE(x) and CIE(y) of 0.649 and 0.336, respectively.

COMPARATIVE 1

OLED Device Using CBP as a Host

An ITO layer is deposited on a substrate and washed. The substrate is loaded in a vacuum chamber, and CuPC (650 Å), NPB (400 Å), an emitting material layer (200 Å) of CBP and (Ir(btp)2(acac) (5%), Alq3 (350 Å), LiF (5 Å), and Al (1000 Å) are sequentially formed.

The emitting diode produces a brightness of 780 cd/m² at an electric current of 0.9 mA and a voltage of 7.5 V and has the CIE(x) and CIE(y) of 0.651 and 0.329, respectively.

The properties and characteristics of the emitting diode in Example 1 to Example 5, Comparative 1 are listed in Table 1. (voltage [V], electric current [mA], brightness [cd/m²], current efficiency [cd/A], power efficiency Pm/WI internal quantum efficiency (IQE) [%])

TABLE 1

| | voltage | electric current | Brightness | Current efficiency | Power efficiency | IQE | CIE (X) | CIE (Y) |
|---|---|---|---|---|---|---|---|---|
| Ex. 1 | 6.0 | 0.9 | 1170 | 11.7 | 6.1 | 15.8 | 0.648 | 0.339 |
| Ex. 2 | 5.5 | 0.9 | 1185 | 11.8 | 6.8 | 16.6 | 0.650 | 0.340 |
| Ex. 3 | 5.3 | 0.9 | 1250 | 12.5 | 7.4 | 17.1 | 0.649 | 0.336 |
| Ex. 4 | 5.4 | 0.9 | 1231 | 12.3 | 7.2 | 16.9 | 0.651 | 0.331 |
| Ex. 5 | 6.5 | 0.9 | 762 | 7.6 | 3.7 | 10.8 | 0.649 | 0.336 |
| Com. 1 | 7.5 | 0.9 | 780 | 7.8 | 3.3 | 10.4 | 0.659 | 0.329 |

As shown in Table 1, the emitting diode using the red phosphorescent compound has advantages in properties of a driving voltage, brightness, current efficiency, power efficiency, internal quantum efficiency and color purity than the related art compound. In addition, the OLED device having improved color purity can be fabricated by a solution process.

SYNTHESIS 2

1. Synthesis of RI-04 Compound
1) dihydrobenzo[1,2]carbazole

Dihydrobenzo[1,2]carbazole was synthesized by following Reaction Formula 5-1.

[Reaction Formula 5-1]

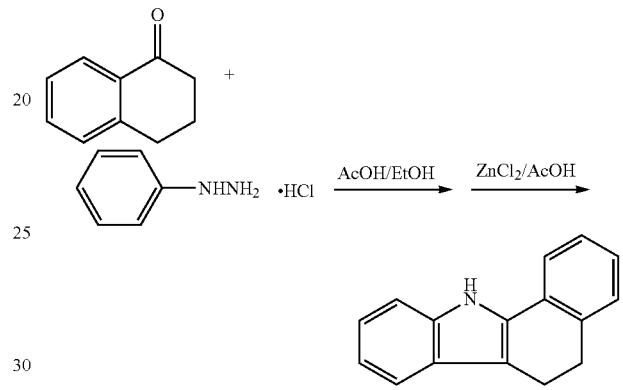

α-teralone (25 g, 0.17 mol), phenylhydrazinuim chloride (24.7 g, 0.17 mol) and acetic acid were put in ethanol in a two-round flask and refluxed for about 1 hour. The solution was cooled into a room temperature, filtered and evaporated to remove the solvent. Zinc chloride (58 g, 0.42 mol) and acetic acid were added into the resultant and refluxed for about 30 minutes. The resulting solution was cooled in to a room temperature and evaporated to remove the solvent. The resultant was precipitated with MC/PE to obtain dihydrobenzo[1,2]carbazole (30 g, yield: 80%).

2) benzo[1,2]carbazole

Benzo[1,2]carbazole was synthesized by following Reaction Formula 5-2.

[Reaction Formula 5-2]

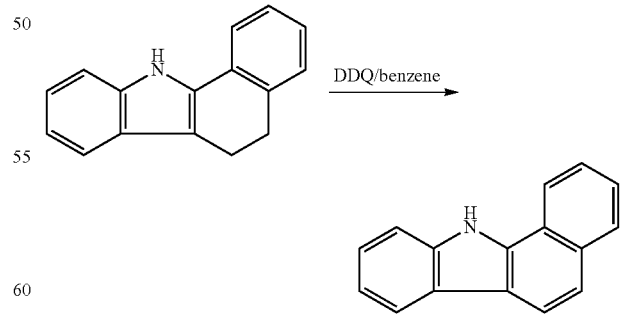

Dihydrobenzo[1,2]carbazole (20 g, 0.09 mol), 2,3-dichloro-5,6-dicyanobenzoquinone (24.6 g, 0.11 mol) and benzene were put in a two-round flask and stirred at a room temperature and for about 3 hours. The solution was extracted with ethyl acetate and evaporated to remove the solvent. The resultant were purified by a silica-gel column to obtain benzo[1,2]carbazole (17.6 g, yield: 90%).

3) 9-2'-pyridylbenzo[1,2]carbazole 9-2'-pyridylbenzo[1,2]carbazole was synthesized by following Reaction Formula 5-3.

[Reaction Formula 5-3]

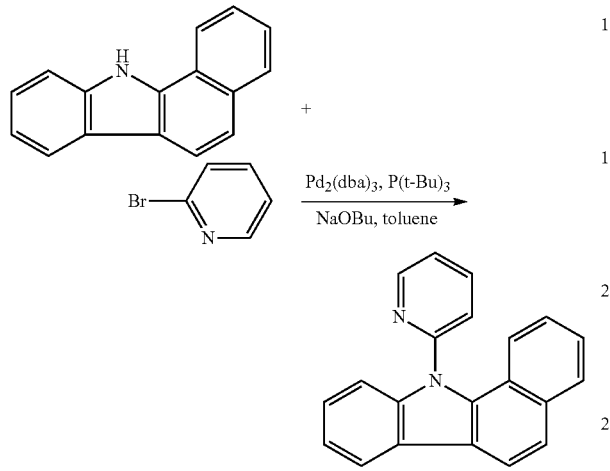

Benzo[1,2]carbazole (5 g, 0.02 mol), 2-bromopyridine (4 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-2'-pyridylbenzo[1,2]carbazole (6 g, yield: 90%).

4) 9-2'-pyridyl-3,6-dibromobenzo[1,2]carbazole 9-2'-pyridyl-3,6-dibromobenzo[1,2]carbazole was synthesized by following Reaction Formula 5-4.

[Reaction Formula 5-4]

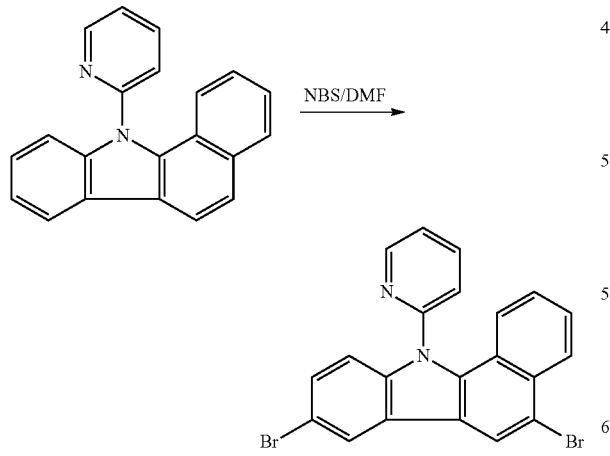

9-2'-pyridylbenzo[1,2]carbazole (6 g, 0.02 mol) and DMF were put in a two-round flask. NBS (7.6 g, 0.042 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 9-2'-pyridyl-3,6-dibromobenzo[1,2]carbazole (7.4 g, yield: 80%).

5) 3,6-di-2'-quinoline-9-2'-pyridylbenzo[1,2]carbazole (RI-04 compound)

RI-04 compound was synthesized by following Reaction Formula 5-5.

[Reaction Formula 5-5]

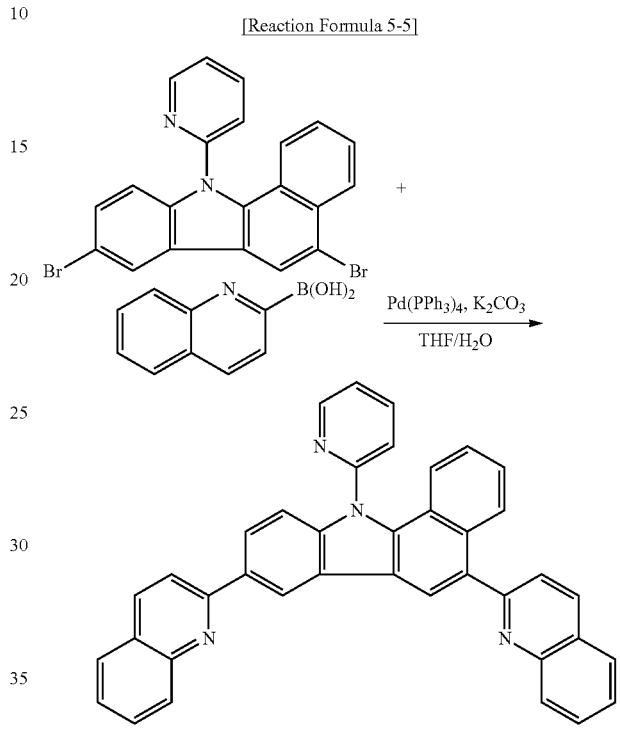

9-2'-pyridyl-3,6-dibromobenzo[1,2]carbazole (2 g, 4.4 mol), 2-quinolineboronic acid (1.7 g, 9.8 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 3,6-di-2'-quinoline-9-2'-pyridylbenzo[1,2]carbazole (RI-04 compound) (1.7 g, yield: 70%).

2. Synthesis of RI-13 Compound 1) 9-3'-pyridylbenzo[1,2]carbazole 9-3'-pyridylbenzo[1,2]carbazole was synthesized by following Reaction Formula 6-1.

[Reaction Formula 6-1]

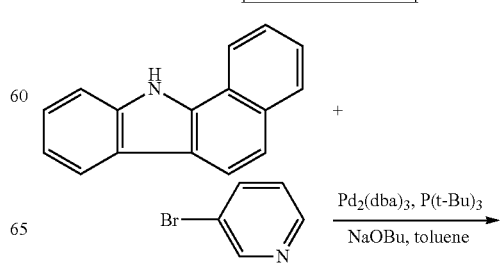

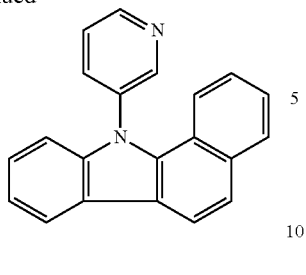

[Reaction Formula 6-3]

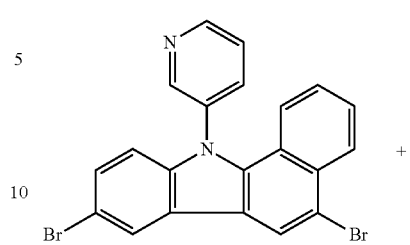

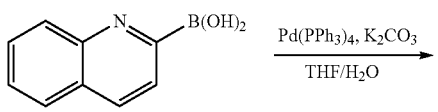

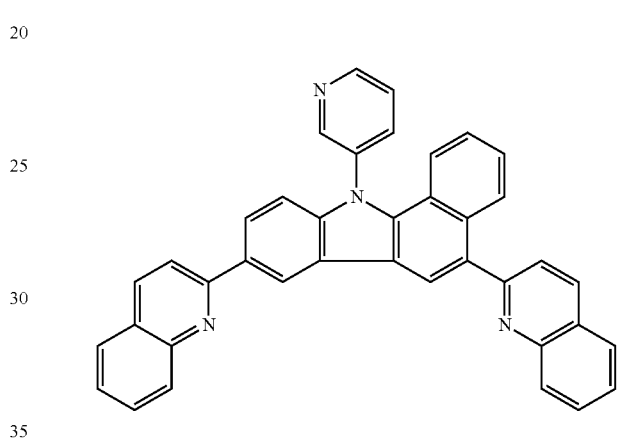

Benzo[1,2]carbazole (5 g, 0.02 mol), 3-bromopyridine (4 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-3'-pyridylbenzo[1,2]carbazole (6 g, yield: 90%).

2) 9-3'-pyridyl-3,6-dibromobenzo[1,2]carbazole 9-3'-pyridyl-3,6-dibromobenzo[1,2]carbazole was synthesized by following Reaction Formula 6-2.

[Reaction Formula 6-2]

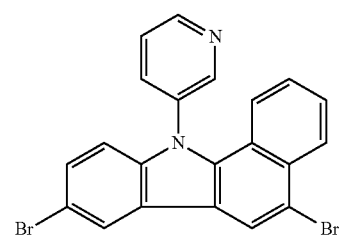

9-3'-pyridylbenzo[1,2]carbazole (6 g, 0.02 mol) and DMF were put in a two-round flask. NBS (7.6 g, 0.042 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 9-3'-pyridyl-3,6-dibromobenzo[1,2]carbazole (7.4 g, yield: 80%).

3) 3,6-di-2'-quinoline-9-3'-pyridylbenzo[1,2]carbazole (RI-13 compound)

RI-13 compound was synthesized by following Reaction Formula 6-3.

3,6-dibromo-9-3'-pyridylbenzo[1,2]carbazole (2 g, 4.4 mol), 2-quinolineboronic acid (1.7 g, 9.8 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 3,6-di-2'-quinoline-9-3'-pyridylbenzo[1,2]carbazole (RI-13 compound) (1.7 g, yield: 70%).

3. Synthesis of RI-49 Compound 1) 9-2'-pyridyl-4'-3"-pyridinebenzo[1,2]carbazole 9-2'-pyridyl-4'-3"-pyridinebenzo[1,2]carbazole was synthesized by following Reaction Formula 7-1.

[Reaction Formula 7-1]

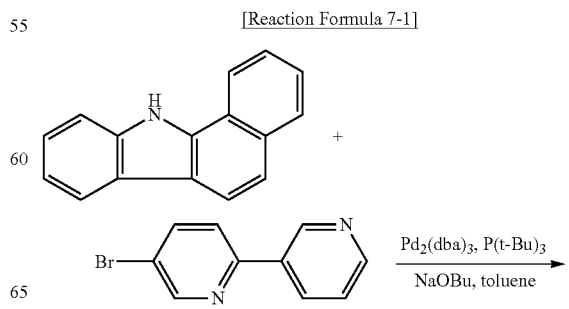

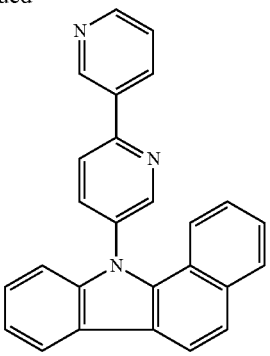

Benzo[1,2]carbazole (5 g, 0.02 mol), 2-bromopyridyl-5-3'-pyridine (8.1 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-2'-pyridyl-4'-3''-pyridinebenzo[1,2]carbazole (6 g, yield: 80%).

2) 3,6-dibromo-9-2'-pyridyl-4'-3''-pyridinebenzo[1,2]carbazole 3,6-dibromo-9-2'-pyridyl-4'-3''-pyridinebenzo[1,2]carbazole was synthesized by following Reaction Formula 7-2.

[Reaction Formula 7-2]

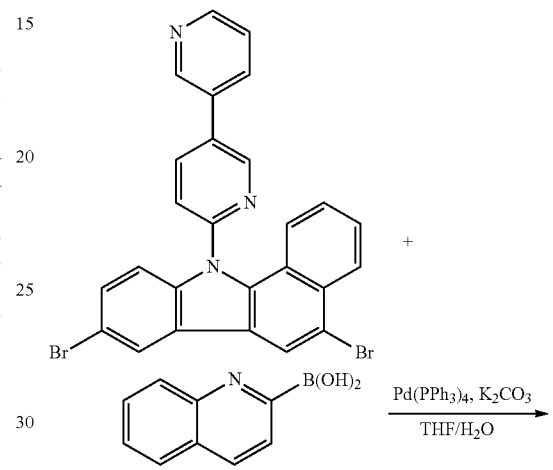

9-2'-pyridyl-4'-3''-pyridinebenzo[1,2]carbazole (6 g, 0.02 mol) and DMF were put in a two-round flask. NBS (6.3 g, 0.04 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 3,6-dibromo-9-2'-pyridyl-4'-3''-pyridinebenzo[1,2]carbazole (6 g, yield: 70%).

3) 3,6-di-2'-quinoline-9-2'-pyridyl-4'-3''-pyridinebenzo[1,2]carbazole (RI-49)

RI-49 compound was synthesized by following Reaction Formula 7-3.

[Reaction Formula 7-3]

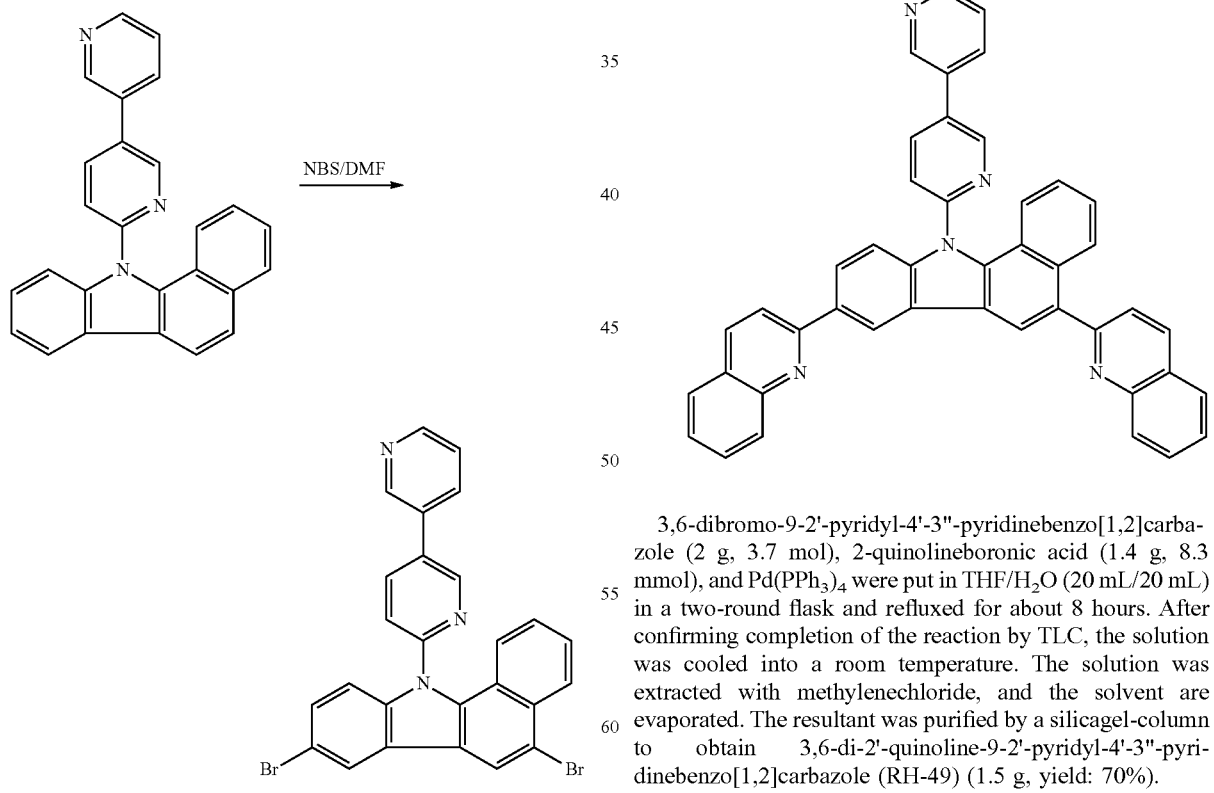

3,6-dibromo-9-2'-pyridyl-4'-3''-pyridinebenzo[1,2]carbazole (2 g, 3.7 mol), 2-quinolineboronic acid (1.4 g, 8.3 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 3,6-di-2'-quinoline-9-2'-pyridyl-4'-3''-pyridinebenzo[1,2]carbazole (RH-49) (1.5 g, yield: 70%).

4. Synthesis of RI-58 Compound 1) 9-3'-pyridyl-5'-2''-pyridinebenzo[1,2]carbazole 9-3'-pyridyl-5'-2''-pyridinebenzo[1,2]carbazole was synthesized by following Reaction Formula 8-1.

[Reaction Formula 8-1]

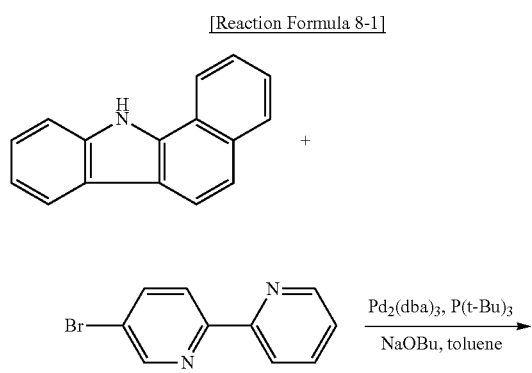

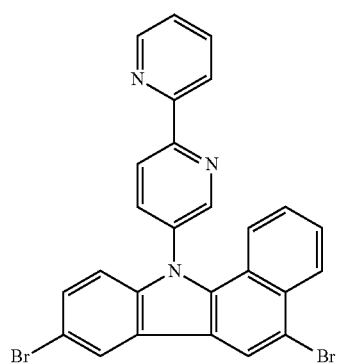

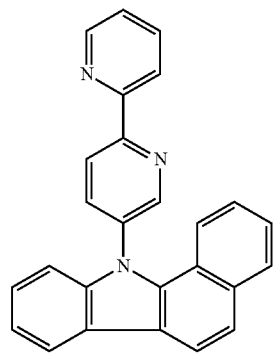

Benzo[1,2]carbazole (5 g, 0.02 mol), 3-bromopyridyl-6-3'-pyridine (8.1 g, 0.025 mol), Pd$_2$(dba)$_3$ (0.42 g, 0.046 mol %), P(t-Bu)$_3$ (0.14 g, 0.069 mol %) and NaOBu (3.3 g, 0.03 mol) were put in toluene in a two-round flask and refluxed at 130° C. and for about 6 hours. The solution was cooled into a room temperature, extracted with methylene chloride, and evaporated to remove the solvent. The resultant was purified by a silica-gel column to obtain 9-3'-pyridyl-4'-2''-pyridinebenzo[1,2]carbazole (6 g, yield: 80%).

2) 3,6-dibromo-9-3'-pyridyl-4'-2''-pyridinebenzo[1,2]carbazole 3,6-dibromo-9-3'-pyridyl-4'-2''-pyridinebenzo[1,2]carbazole was synthesized by following Reaction Formula 8-2.

[Reaction Formula 8-2]

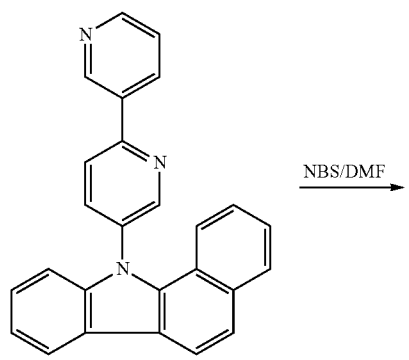

9-3'-pyridyl-4'-2''-pyridinebenzo[1,2]carbazole (6 g, 0.02 mol) and DMF were put in a two-round flask. NBS (6.3 g, 0.04 mol) were slowly dropped in an ice-bath, and the solution was stirred for about 3 hours. The solution was quenched by distilled water, extracted with methylene chloride, and evaporated to remove the solvent. The resultant was purified by a silica-gel column to obtain 3,6-dibromo-9-3'-pyridyl-4'-2''-pyridinebenzo[1,2]carbazole (6 g, yield: 80%).

3) 3,6-di-2'-quinoline-9-3'-pyridyl-4'-2''-pyridinebenzo[1,2]carbazole (RI-58)

RH-58 compound was synthesized by following Reaction Formula 8-3.

[Reaction Formula 8-3]

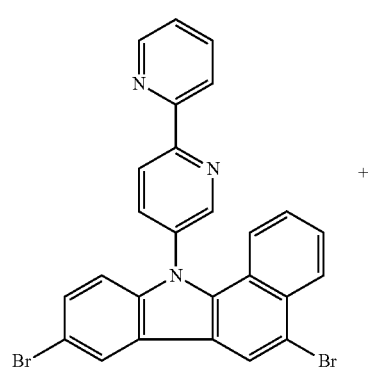

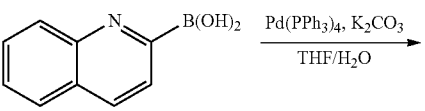

-continued

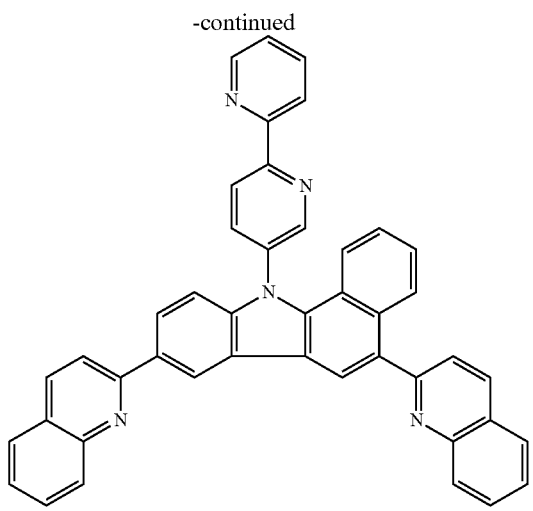

3,6-dibromo-9-3'-pyridyl-4'-2"-pyridinebenzo[1,2]carbazole (2 g, 3.7 mol), 2-quinolineboronic acid (1.4 g, 8.3 mmol), and Pd(PPh$_3$)$_4$ were put in THF/H$_2$O (20 mL/20 mL) in a two-round flask and refluxed for about 8 hours. After confirming completion of the reaction by TLC, the solution was cooled into a room temperature. The solution was extracted with methylenechloride, and the solvent are evaporated. The resultant was purified by a silicagel-column to obtain 3,6-di-2'-quinoline-9-3'-pyridyl-4'-2"-pyridinebenzo[1,2]carbazole (RI-58) (1.7 g, yield: 70%).

EXAMPLE 6

OLED Device Using RI-04 Compound as a Host

An ITO layer is deposited on a substrate and washed. The substrate is loaded in a vacuum chamber, and CuPC (650 Å), NPB (400 Å), an emitting material layer (200 Å) of RI-04 and (Ir(btp)2(acac) (5%), Alq3 (350 Å), LiF (5 Å), and Al (1000 Å) are sequentially formed.

The emitting diode produces a brightness of 1180 cd/m$^2$ at an electric current of 0.9 mA and a voltage of 5.9 V and has the CIE(x) and CIE(y) of 0.649 and 0.338, respectively.

EXAMPLE 7

OLED Device Using RI-13 Compound as a Host

An ITO layer is deposited on a substrate and washed. The substrate is loaded in a vacuum chamber, and CuPC (650 Å), NPB (400 Å), an emitting material layer (200 Å) of RI-13 and (Ir(btp)2(acac) (5%), Alq3 (350 Å), LiF (5 Å), and Al (1000 Å) are sequentially formed.

The emitting diode produces a brightness of 1195 cd/m$^2$ at an electric current of 0.9 mA and a voltage of 5.7 V and has the CIE(x) and CIE(y) of 0.650 and 0.340, respectively.

EXAMPLE 8

OLED Device Using RI-49 Compound as a Host

An ITO layer is deposited on a substrate and washed. The substrate is loaded in a vacuum chamber, and CuPC (650 Å), NPB (400 Å), an emitting material layer (200 Å) of RI-49 and (Ir(btp)2(acac) (5%), Alq3 (350 Å), LiF (5 Å), and Al (1000 Å) are sequentially formed.

The emitting diode produces a brightness of 1260 cd/m$^2$ at an electric current of 0.9 mA and a voltage of 5.6 V and has the CIE(x) and CIE(y) of 0.650 and 0.336, respectively.

EXAMPLE 9

OLED Device Using RI-58 Compound as a Host

An ITO layer is deposited on a substrate and washed. The substrate is loaded in a vacuum chamber, and CuPC (650 Å), NPB (400 Å), an emitting material layer (200 Å) of RI-58 and (Ir(btp)2(acac) (5%), Alq3 (350 Å), LiF (5 Å), and Al (1000 Å) are sequentially formed.

The emitting diode produces a brightness of 1211 cd/m$^2$ at an electric current of 0.9 mA and a voltage of 5.5 V and has the CIE(x) and CIE(y) of 0.651 and 0.330, respectively.

EXAMPLE 10

OLED Device Using RI-58 Compound as a Host (Solution Process)

An ITO layer is deposited on a substrate and washed to form an anode. The substrate is loaded in a vacuum chamber, and a hole injecting layer (800 Å) of PEDOT:PSS (spin coating: 3000 rpm, baking condition: 120° C. for 1 hr) and an emitting material layer (250 Å) of RI-58 and (Ir(btp)2 (acac) (2%) (spin coating: 3000 rpm, baking condition: 100° C. for 30 min) are coated. Alq3 (350 Å), LiF (5 Å), and Al (1000 Å) are sequentially formed on the emitting material layer.

The emitting diode produces a brightness of 772 cd/m$^2$ at an electric current of 0.9 mA and a voltage of 6.5 V and has the CIE(x) and CIE(y) of 0.650 and 0.336, respectively.

COMPARATIVE 2

OLED Device Using CBP as a Host

An ITO layer is deposited on a substrate and washed. The substrate is loaded in a vacuum chamber, and CuPC (650 Å), NPB (400 Å), an emitting material layer (200 Å) of CBP and (Ir(btp)2(acac) (5%), Alq3 (350 Å), LiF (5 Å), and Al (1000 Å) are sequentially formed.

The emitting diode produces a brightness of 780 cd/m$^2$ at an electric current of 0.9 mA and a voltage of 7.5 V and has the CIE(x) and CIE(y) of 0.651 and 0.329, respectively.

The properties and characteristics of the emitting diode in Example 6 to Example 10, Comparative 2 are listed in Table 2. (voltage [V], electric current [mA], brightness [cd/m$^2$], current efficiency [cd/A], power efficiency [1 m/W], internal quantum efficiency (IQE) [%])

TABLE 2

| | voltage | electric current | Brightness | Current efficiency | Power efficiency | IQE | CIE (X) | CIE (Y) |
|---|---|---|---|---|---|---|---|---|
| Ex. 6 | 5.9 | 0.9 | 1180 | 11.8 | 6.3 | 15.8 | 0.649 | 0.338 |
| Ex. 7 | 5.7 | 0.9 | 1195 | 11.9 | 6.6 | 16.6 | 0.650 | 0.340 |
| Ex. 8 | 5.6 | 0.9 | 1260 | 12.6 | 7.1 | 17.1 | 0.650 | 0.336 |
| Ex. 9 | 5.5 | 0.9 | 1241 | 12.4 | 7.1 | 16.9 | 0.651 | 0.330 |
| Ex. 10 | 6.5 | 0.9 | 772 | 7.7 | 3.7 | 10.8 | 0.650 | 0.336 |
| Com. 2 | 7.5 | 0.9 | 780 | 7.8 | 3.3 | 10.4 | 0.659 | 0.329 |

As shown in Table 2, the emitting diode using the red phosphorescent compound has advantages in properties of a driving voltage, brightness, current efficiency, power efficiency, internal quantum efficiency and color purity than the related art compound. In addition, the OLED device having improved color purity can be fabricated by a solution process.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A red phosphorescent compound having the following formula:

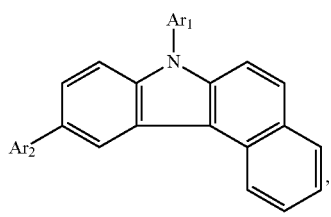

wherein Ar1 is selected from substituted or non-substituted pyridine, substituted or non-substituted quinoline and substituted or non-substituted phenanthroline, and Ar2 is selected from substituted or non-substituted pyridine and substituted or non-substituted quinoline.

2. The compound according to claim 1, wherein the substituent of Ar1 and Ar2 is independently selected from C5-C20 aryl, C1-C10 alkyl, C1-C10 alkoxy, halogen, cyano and silyl.

3. The compound according to claim 1, wherein the substituent of Ar1 and Ar2 is independently selected from pyridinyl, bipyridinyl, quinolinyl, isoquinolinyl, terpyridinyl, phenanthrolinyl, methyl, ethyl, propyl, iso-propyl, butyl, methoxy, ethoxy, buthoxy, fluorine, chloride, cyano and trimethylsilyl.

4. The compound according to claim 1, wherein Ar1 and Ar2 is independently selected from following:

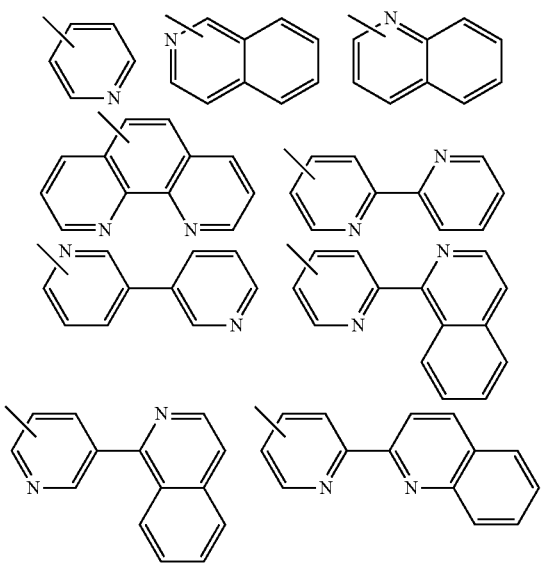

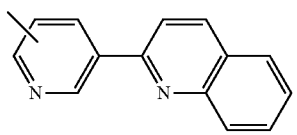

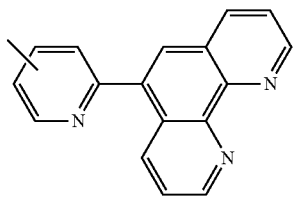

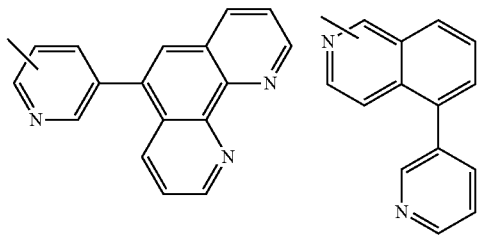

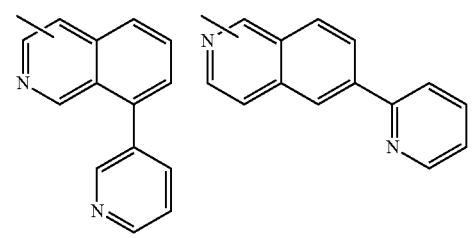

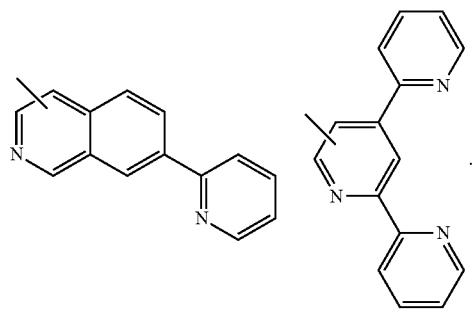

5. The compound according to claim 1, wherein the compound includes one of following:

RH-19

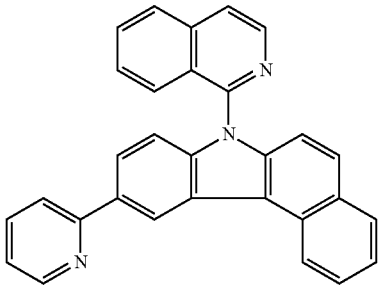

-continued
RH-20
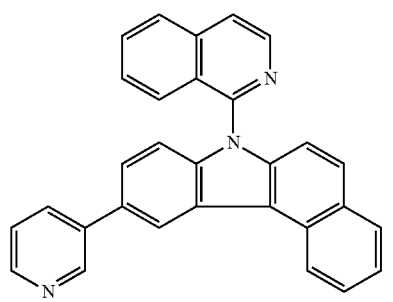
RH-21
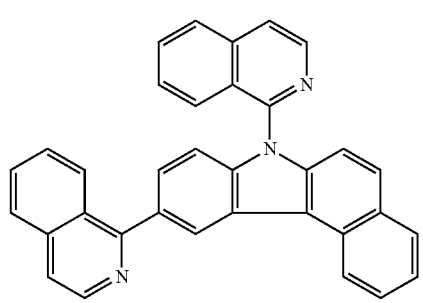
RH-22
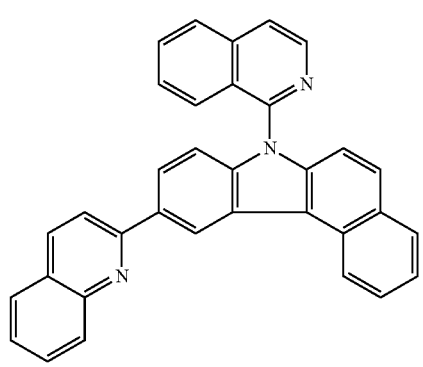
RH-23
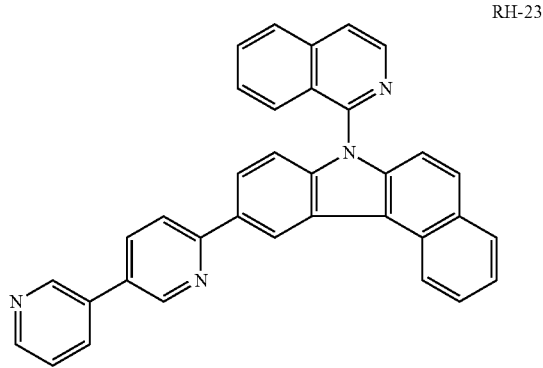
-continued
RH-24
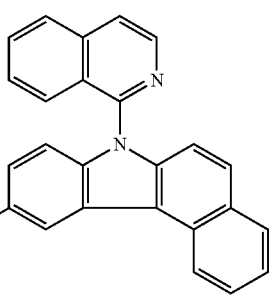
RH-25
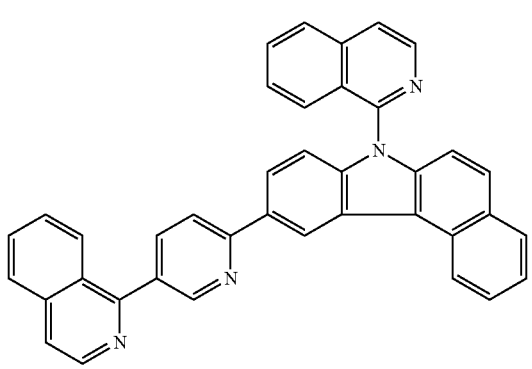
RH-26
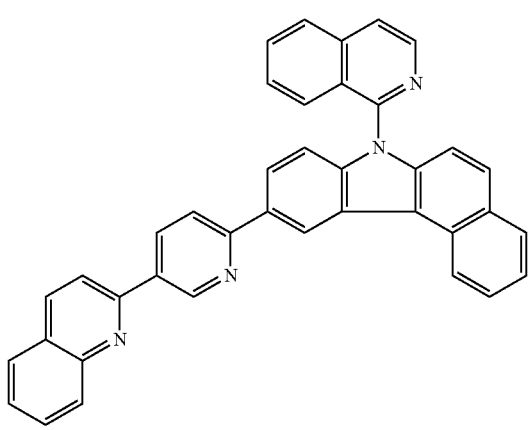
RH-27
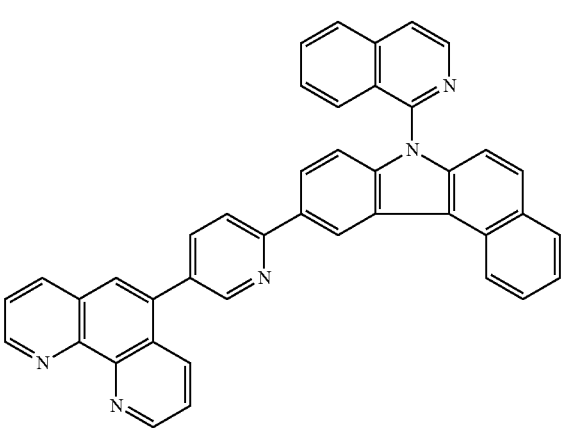

RH-28
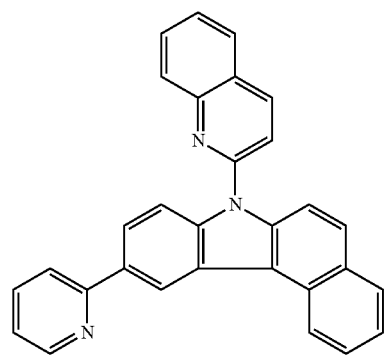
RH-29
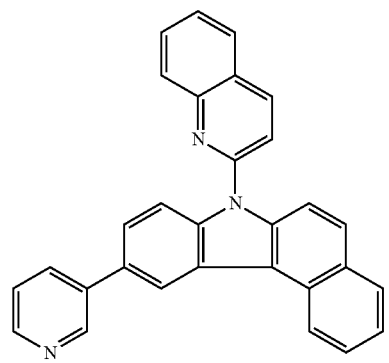
RH-30
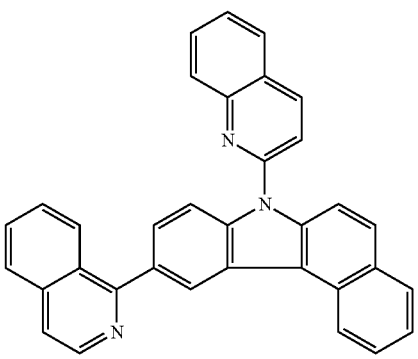
RH-31
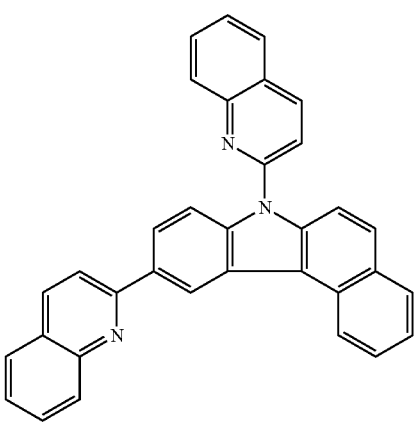
RH-32
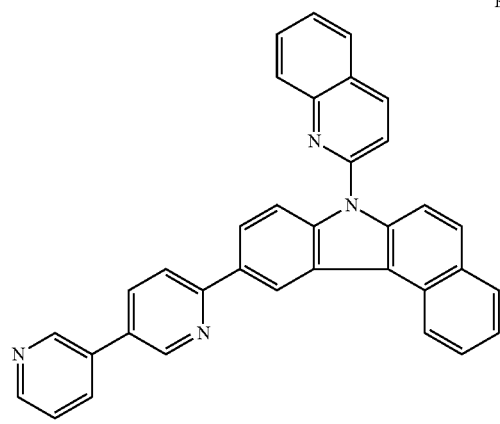
RH-33
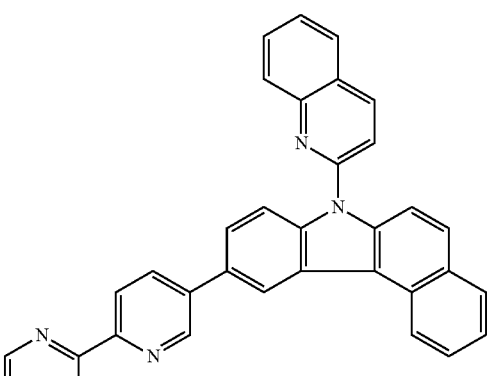
RH-34
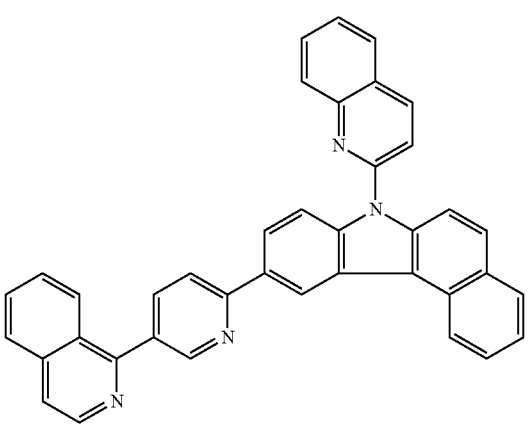

-continued
RH-35
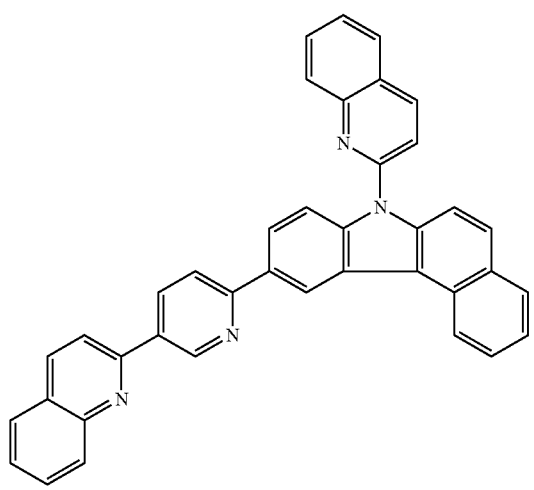
RH-36
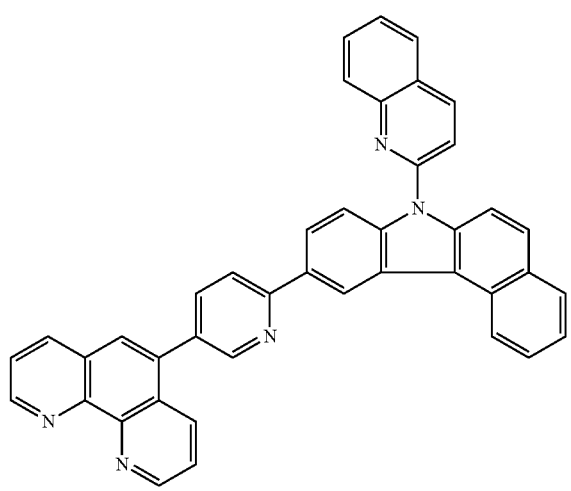
RH-37
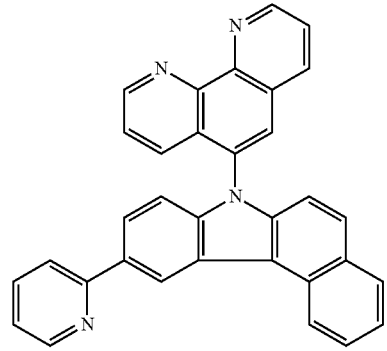
-continued
RH-38
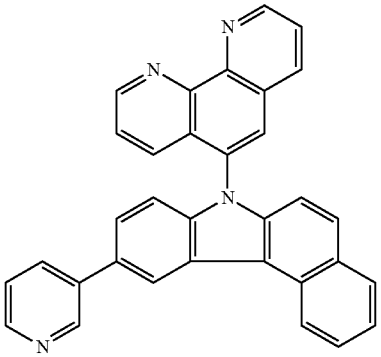
RH-39
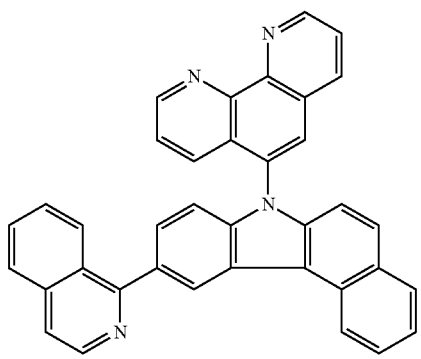
RH-40
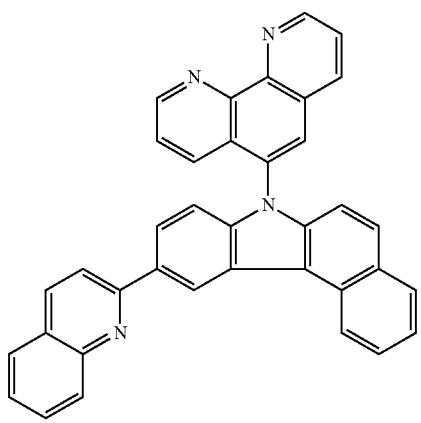
RH-41
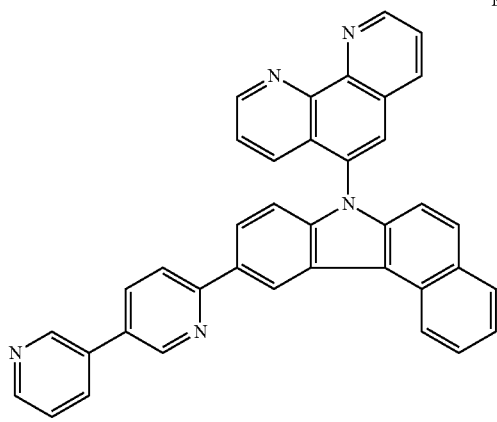

-continued
RH-42
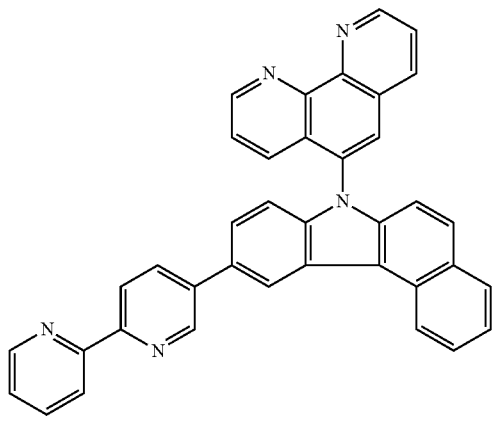
RH-43
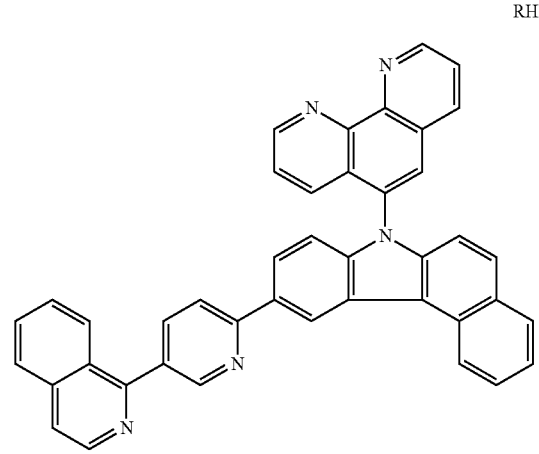
RH-44
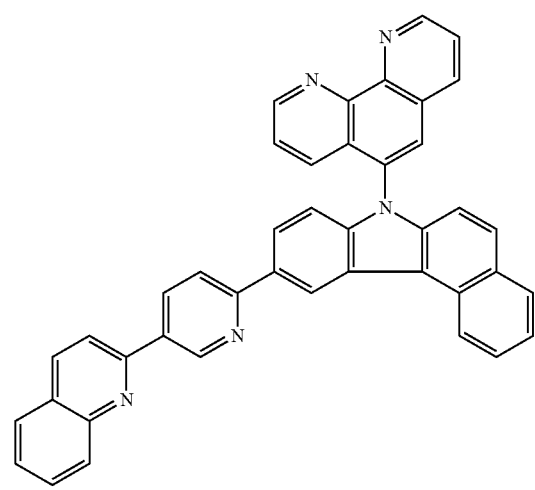
-continued
RH-45
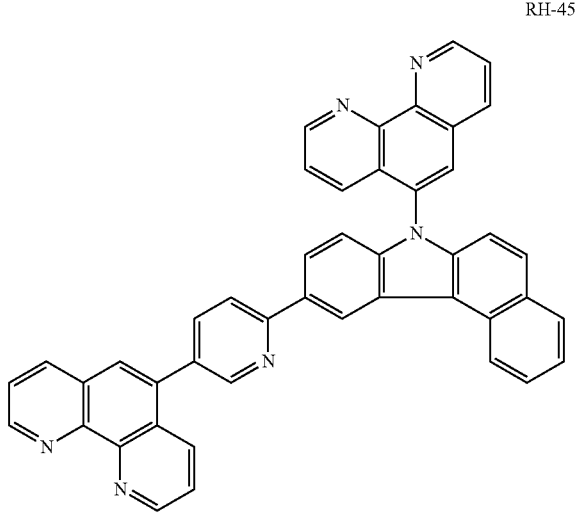
RH-46
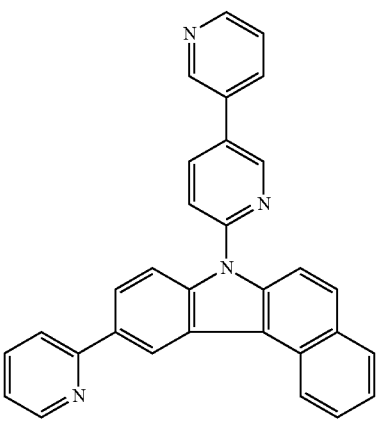
RH-47
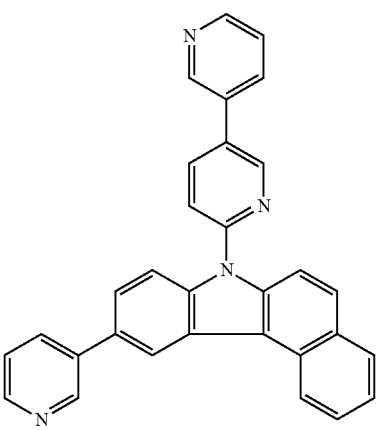

RH-48
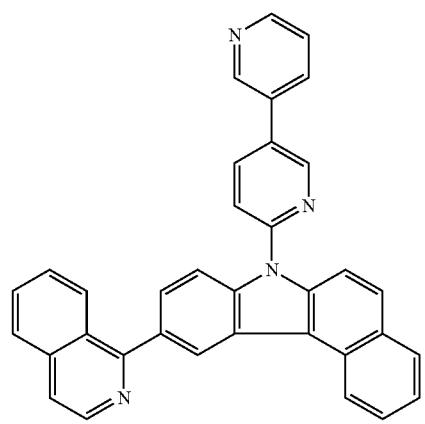
RH-51
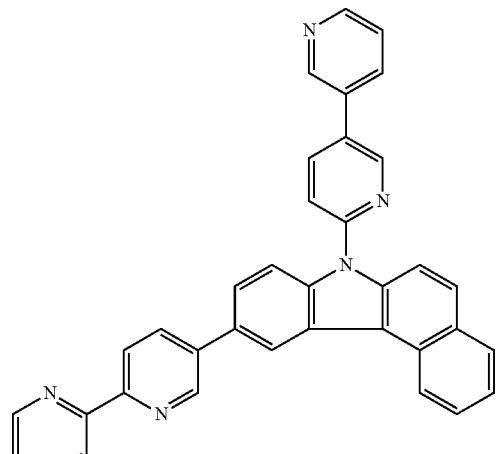
RH-49
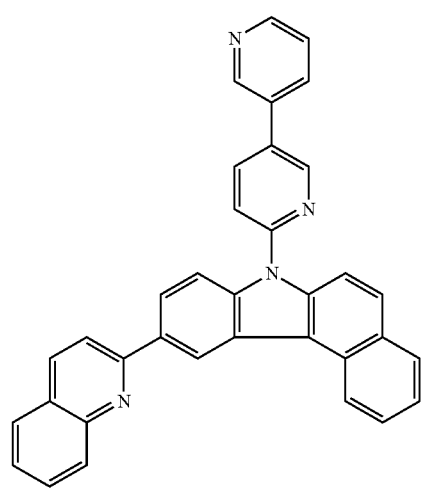
RH-52
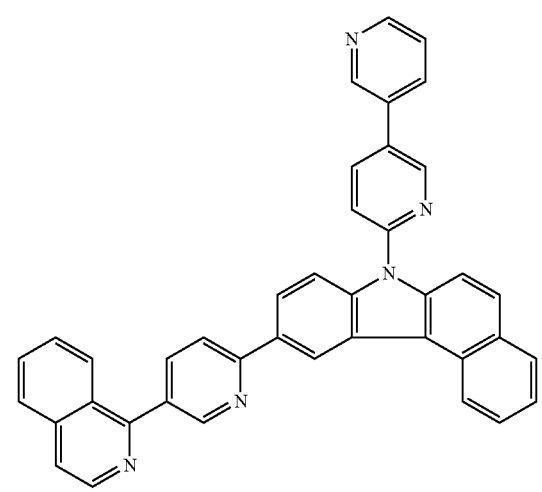
RH-50
RH-53
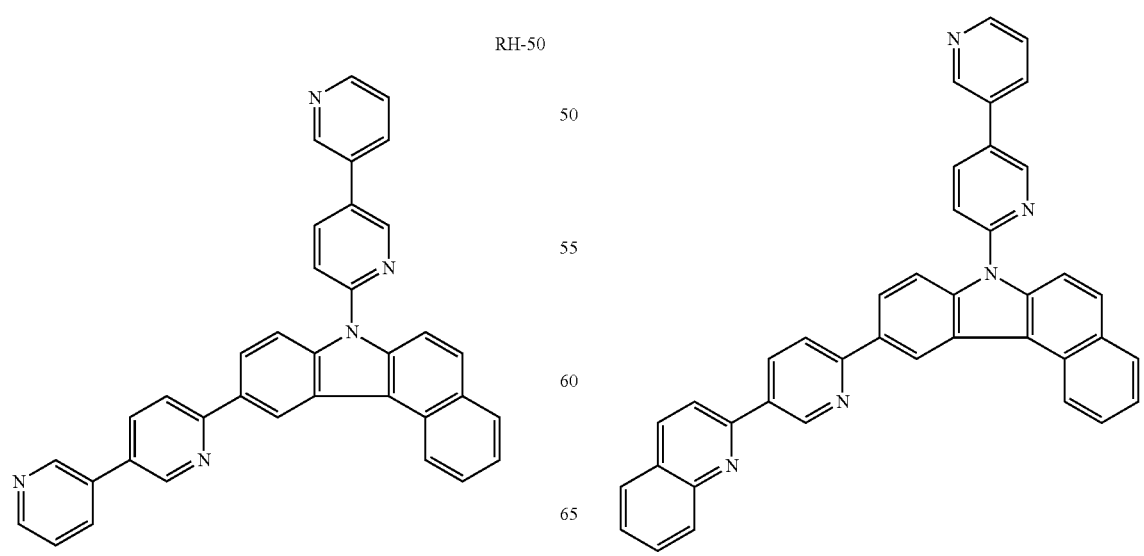

-continued
RH-54
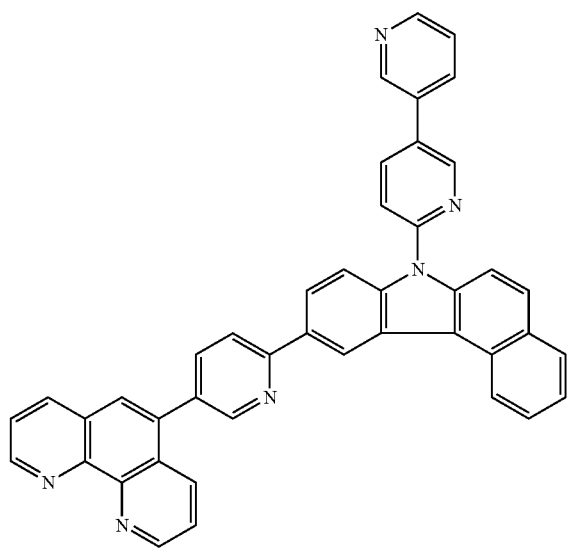
RH-55
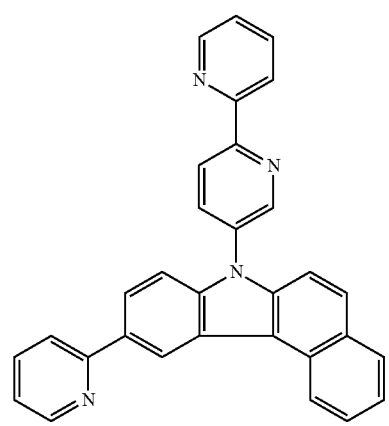
RH-56
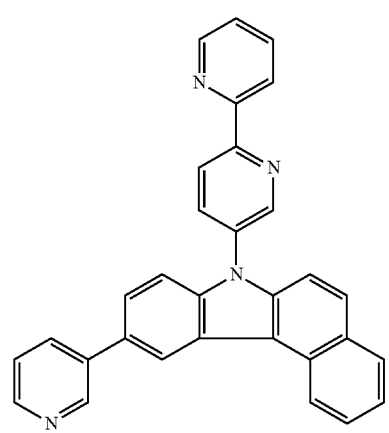
-continued
RH-57
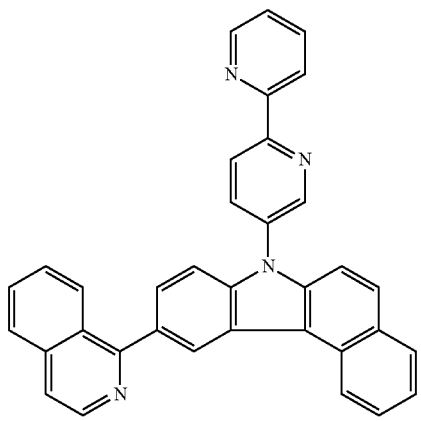
RH-58
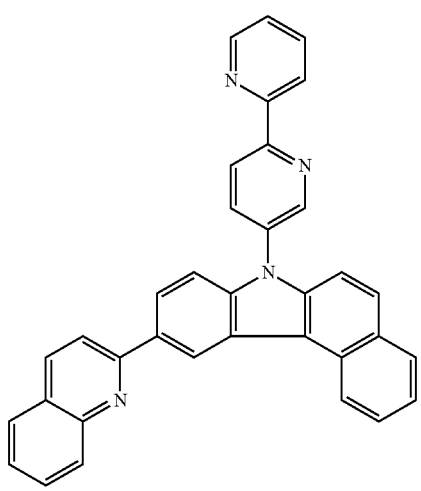
RH-59
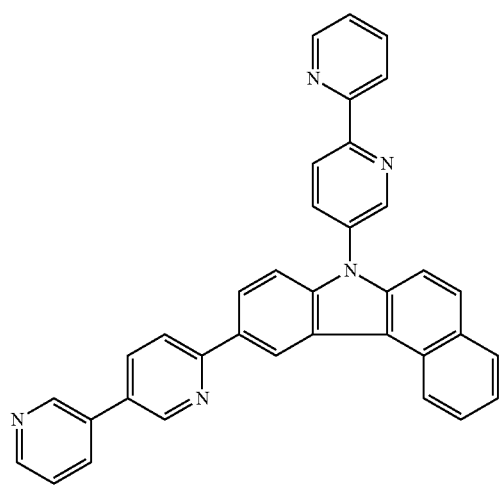

RH-60
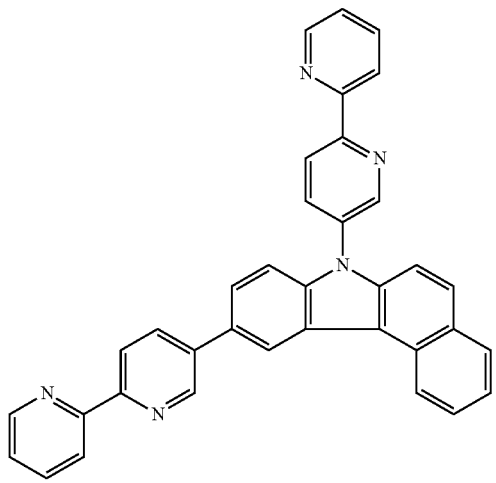
RH-61
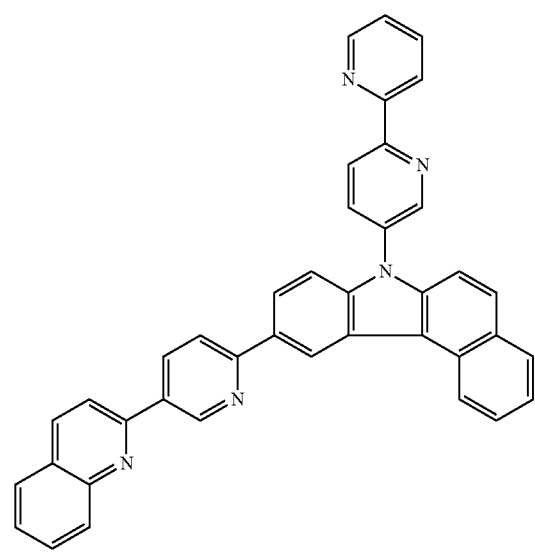
RH-62
RH-63
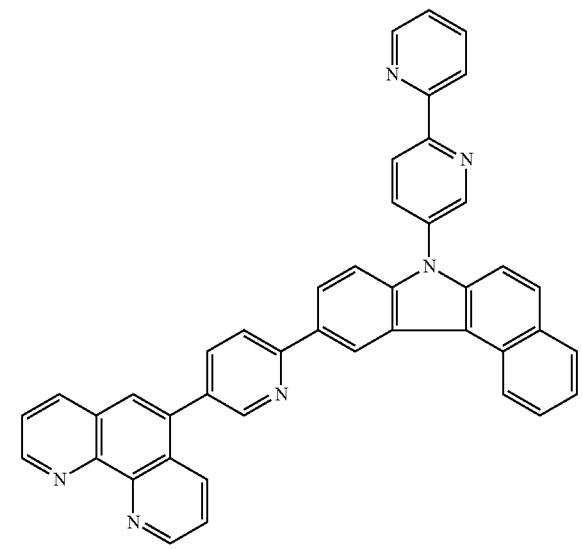
RH-64
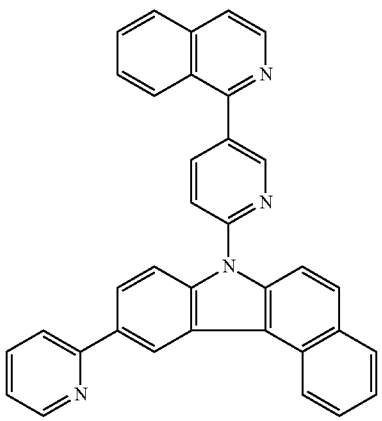
RH-65
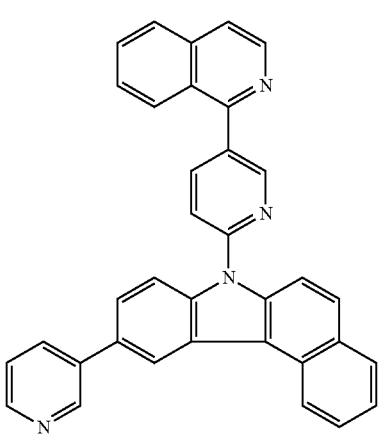

-continued
RH-66
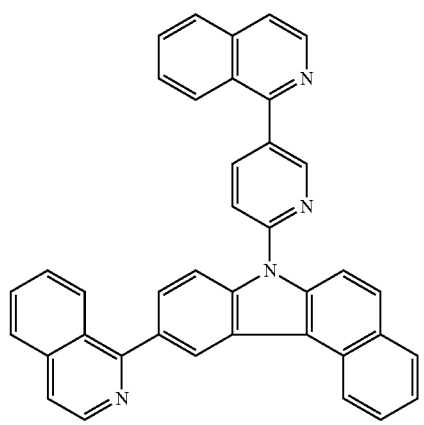
RH-67
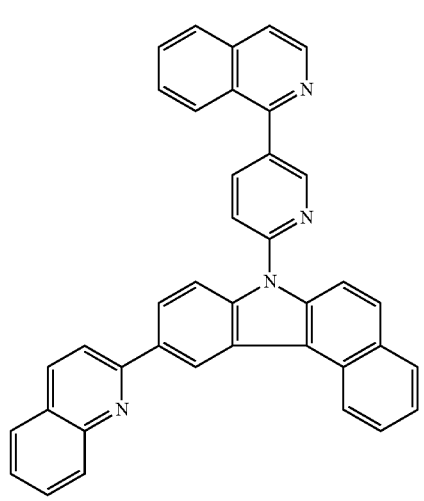
RH-68
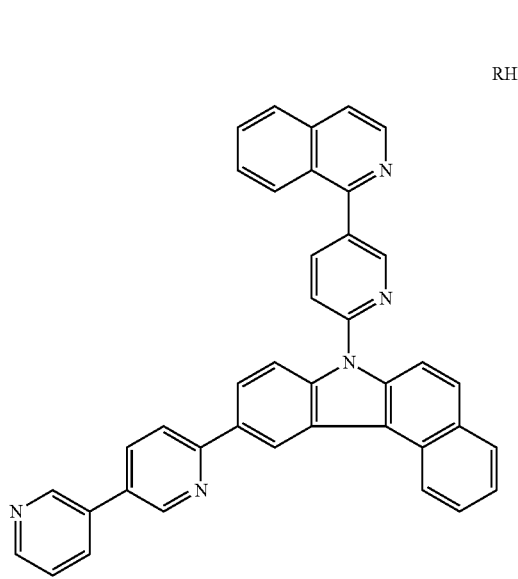
-continued
RH-69
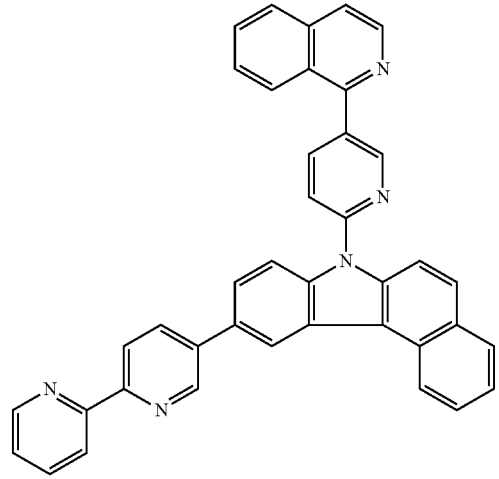
RH-70
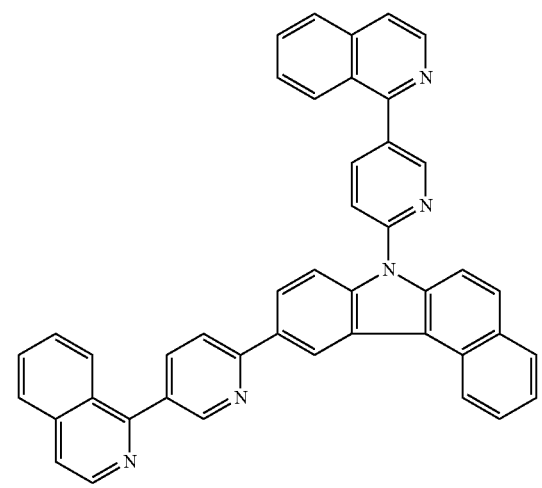
RH-71
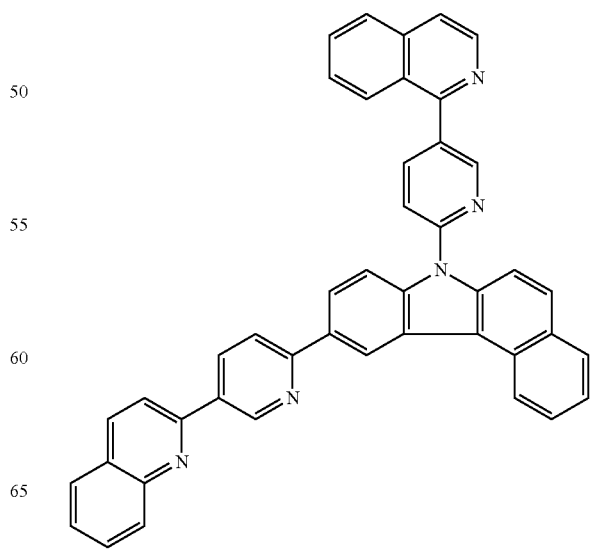

RH-72
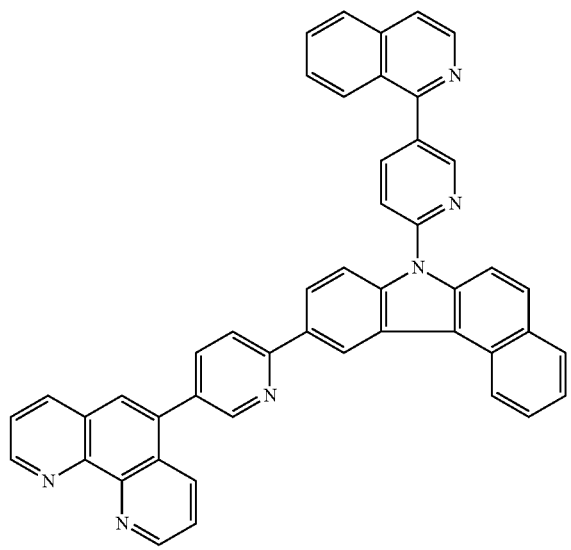
RH-73
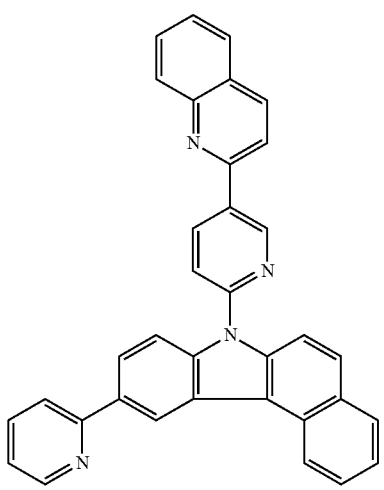
RH-74
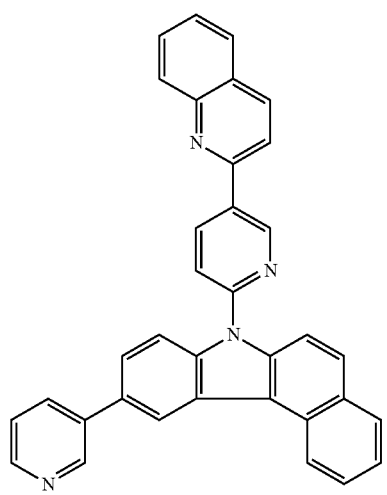
RH-75
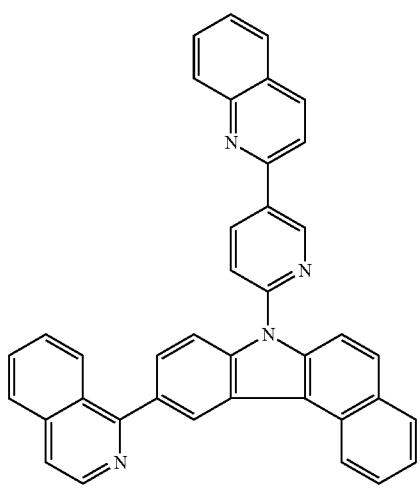
RH-76
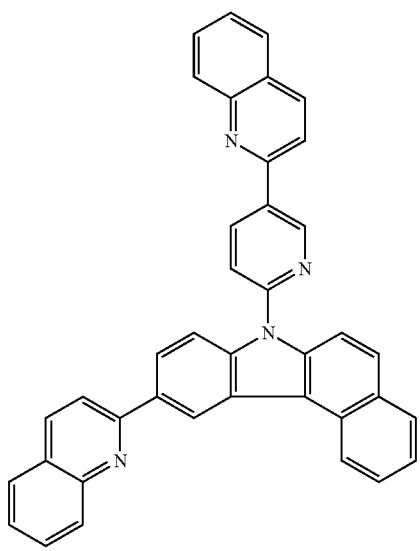
RH-77
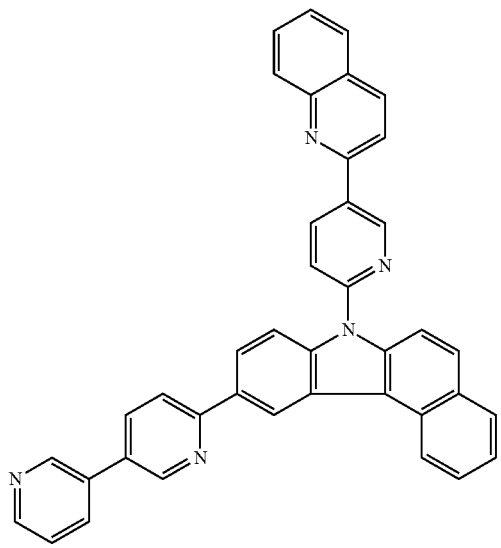

RH-78
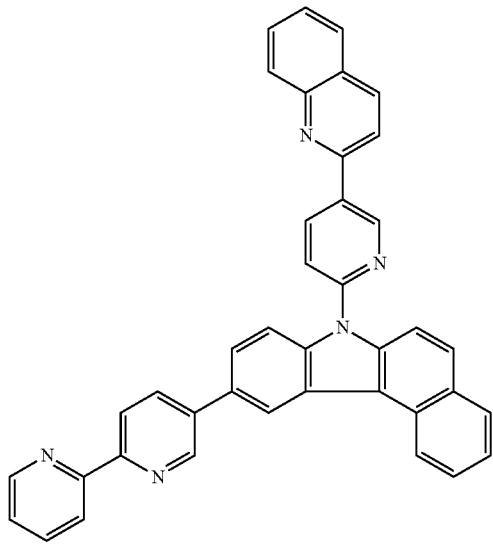
RH-79
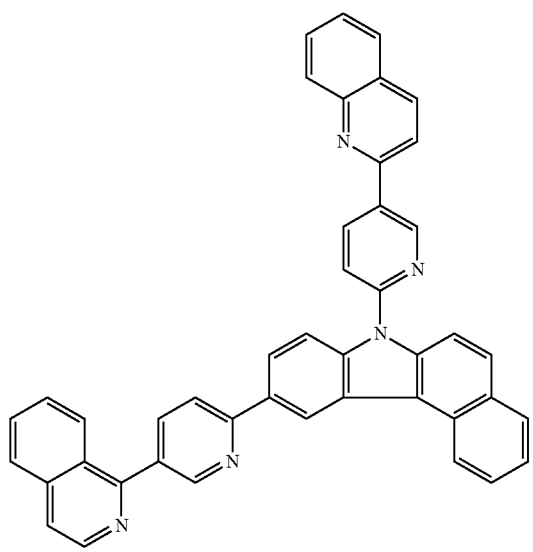
RH-80
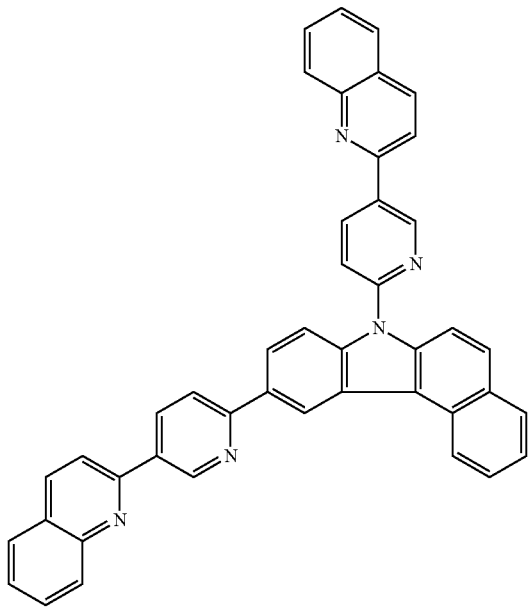
RH-81
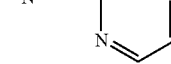

RH-82
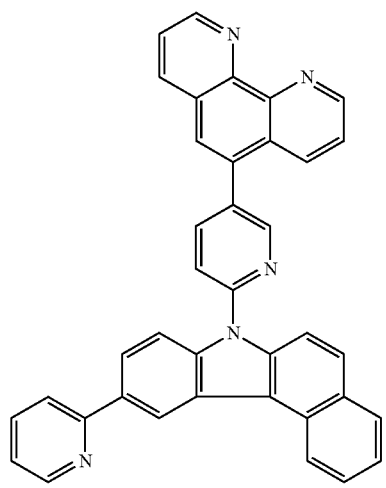
RH-83
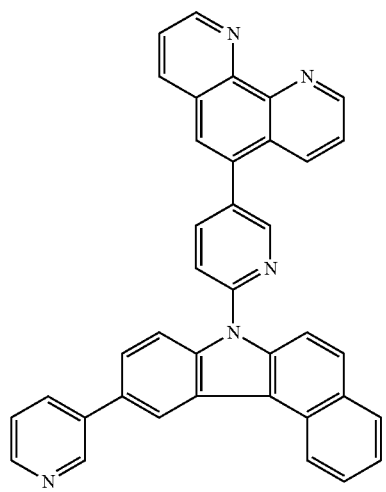
RH-84
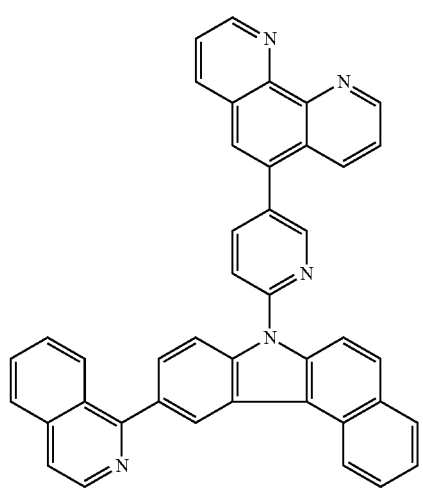
RH-85
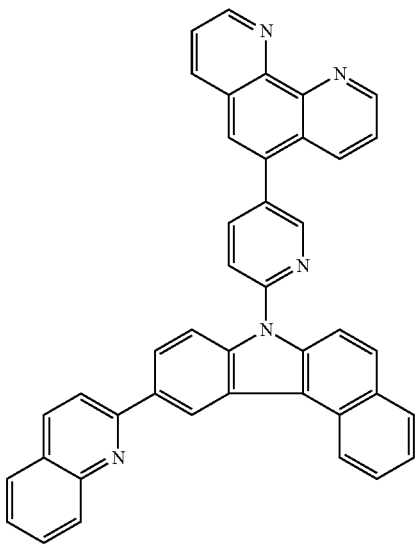
RH-86
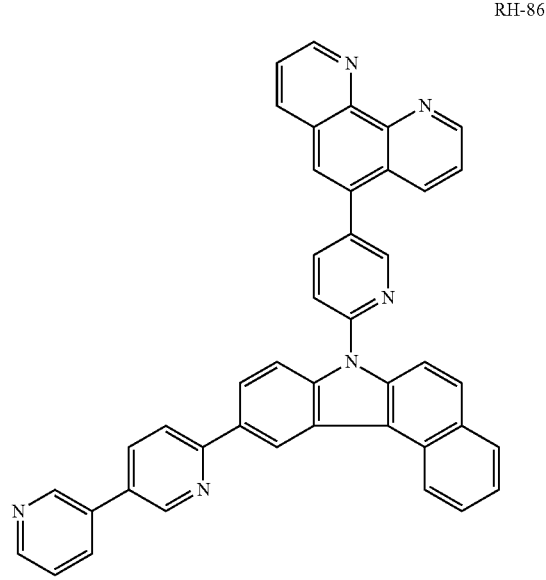

-continued
RH-87
RH-88
-continued
RH-89
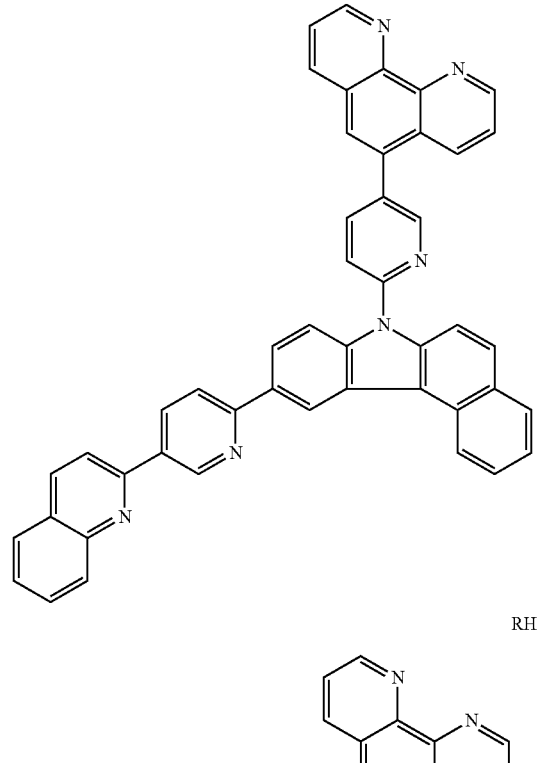
RH-90
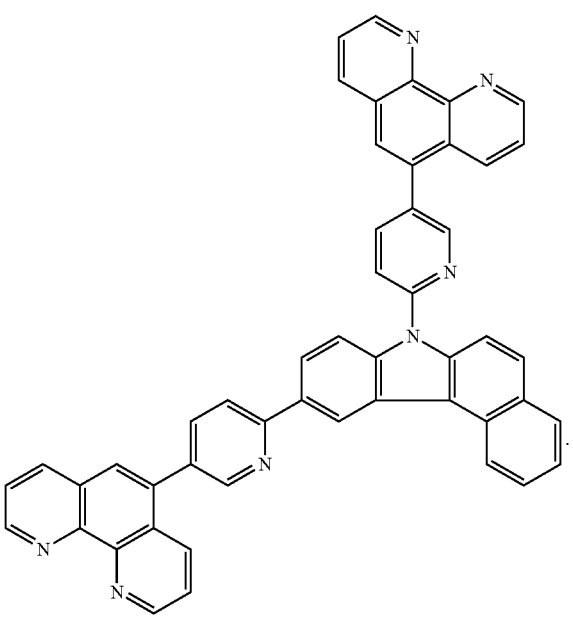
6. A red phosphorescent compound having the following formula:
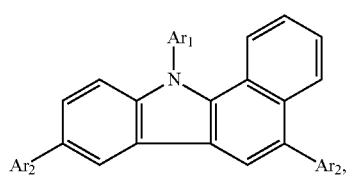
wherein Ar1 is selected from substituted or non-substituted pyridine, substituted or non-substituted quinoline and substituted or non-substituted phenanthroline, and Ar2 is selected from substituted or non-substituted pyridine and substituted or non-substituted quinoline.

7. The compound according to claim 6, wherein the substituent of Ar1 and Ar2 is independently selected from C5-C20 aryl, C1-C10 alkyl, C1-C10 alkoxy, halogen, cyano and silyl.

8. The compound according to claim 6, wherein the substituent of Ar1 and Ar2 is independently selected from pyridinyl, bipyridinyl, quinolinyl, isoquinolinyl, terpyridinyl, phenanthrolinyl, methyl, ethyl, propyl, iso-propyl, butyl, methoxy, ethoxy, buthoxy, fluorine, chloride, cyano and trimethylsilyl.

9. The compound according to claim 6, wherein Ar1 and Ar2 is independently selected from following:

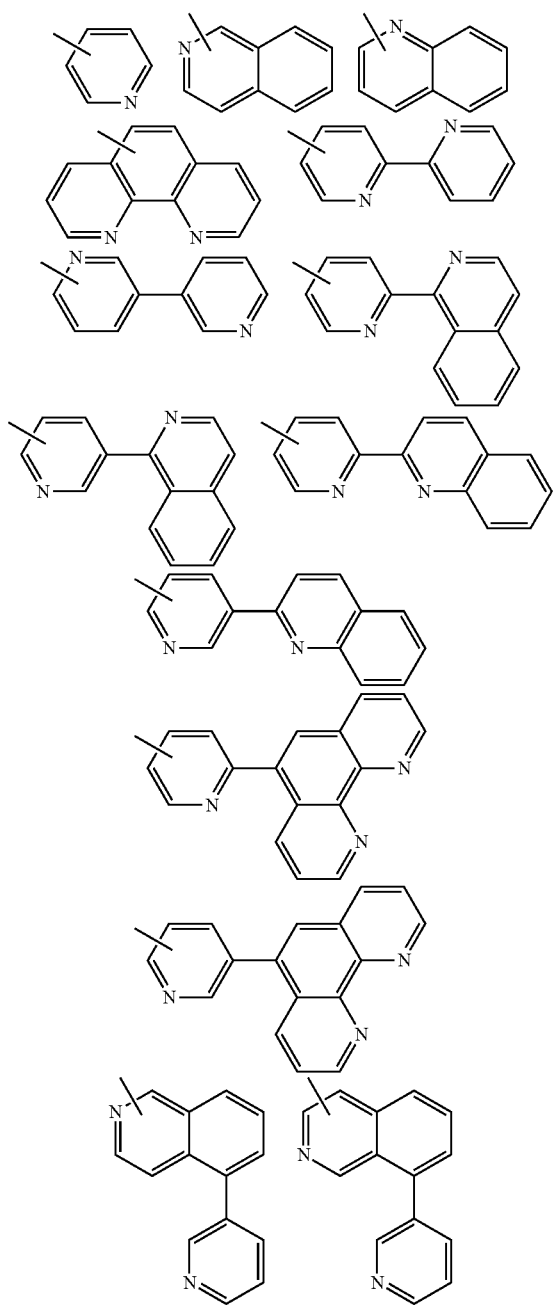

-continued

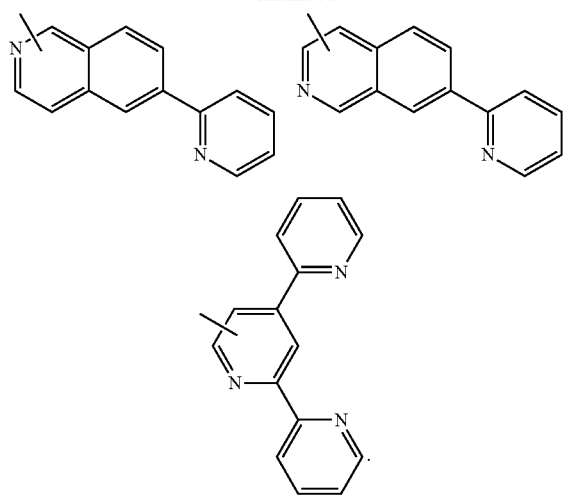

10. The compound according to claim 6, wherein the compound includes one of following:

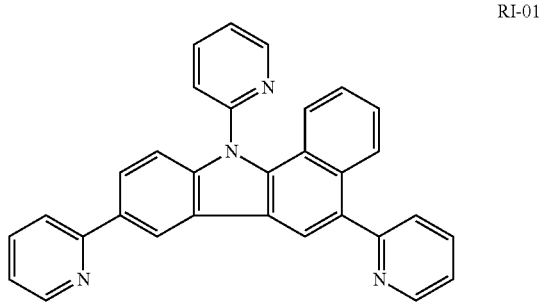

RI-01

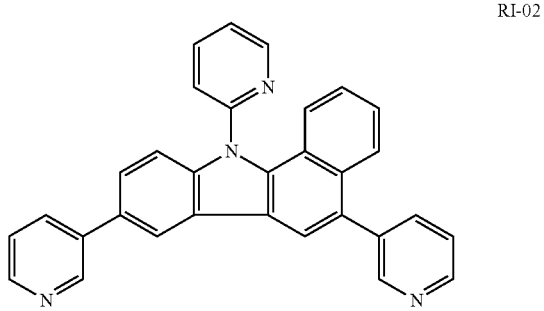

RI-02

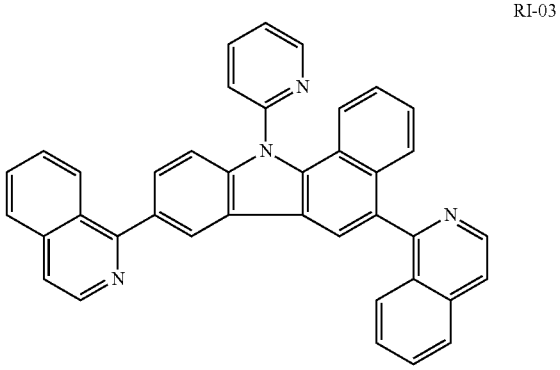

RI-03

RI-04
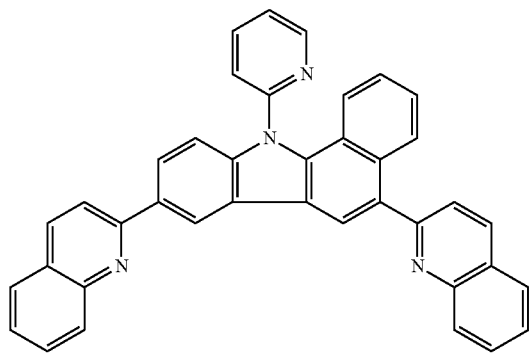
RI-05
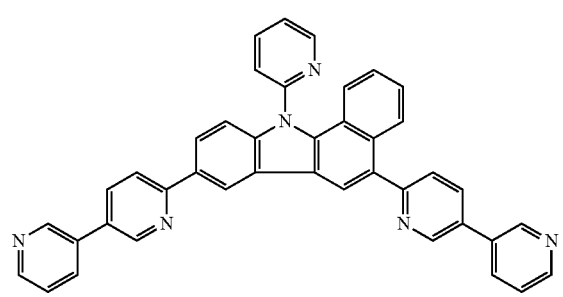
RI-06
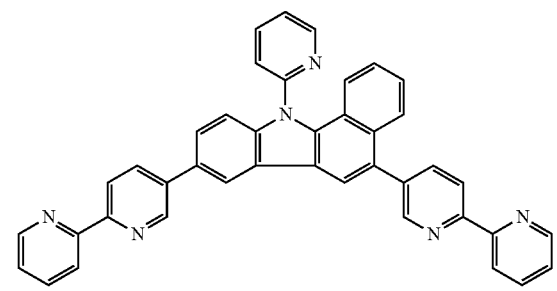
RI-07
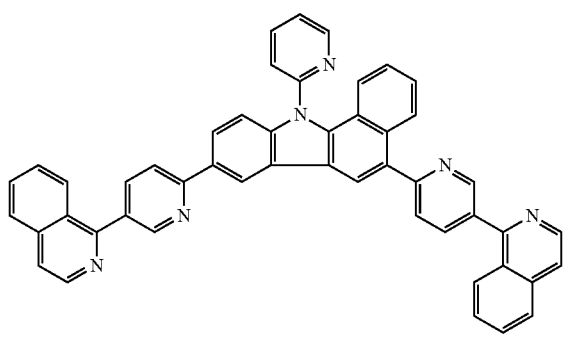
RI-08
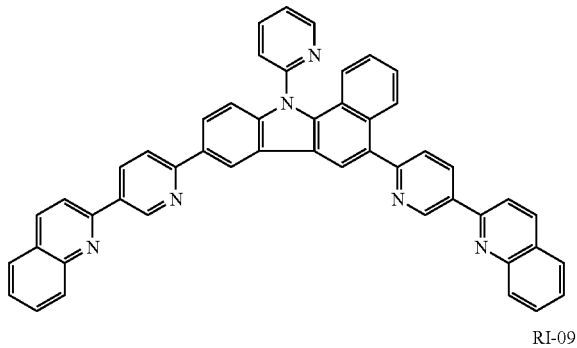
RI-09
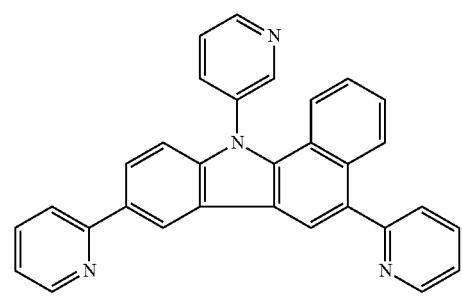
RI-10
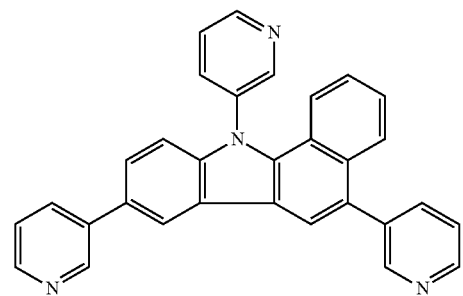
RI-11
RI-12
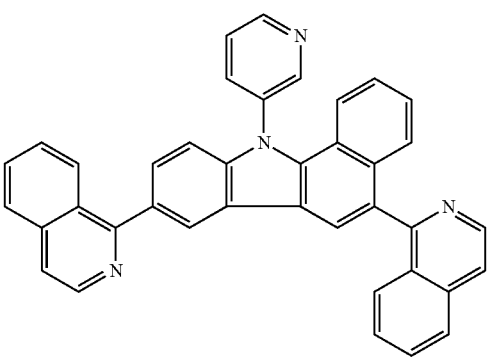

RI-13
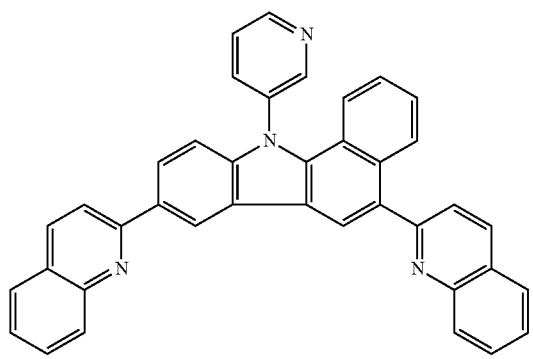
RI-14
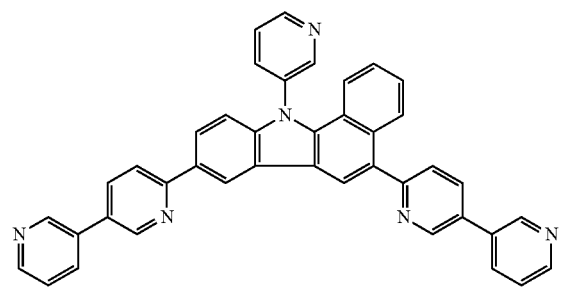
RI-15
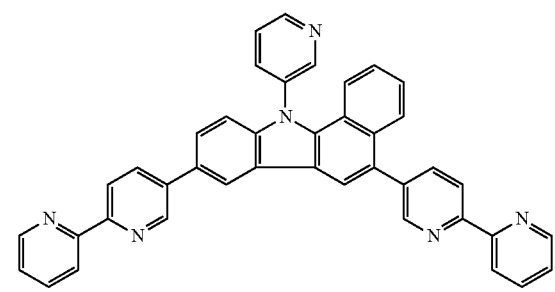
RI-16
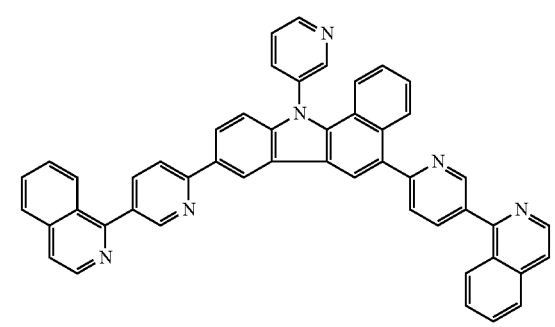
RI-17
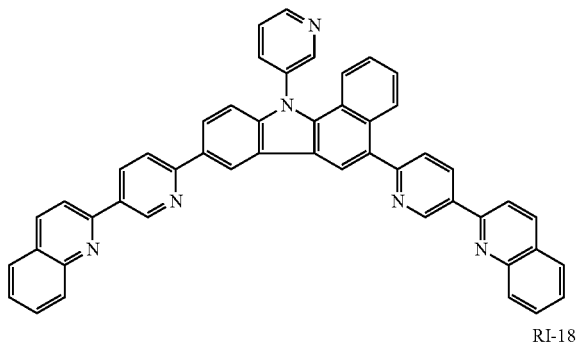
RI-18
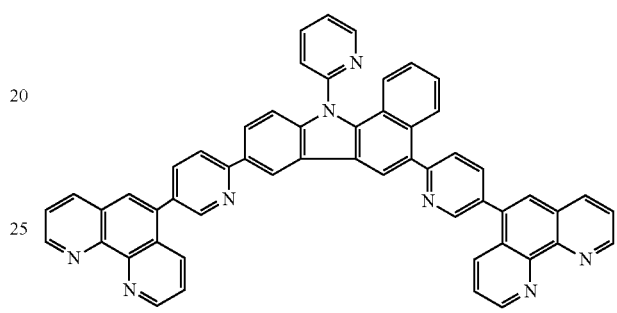
RI-19
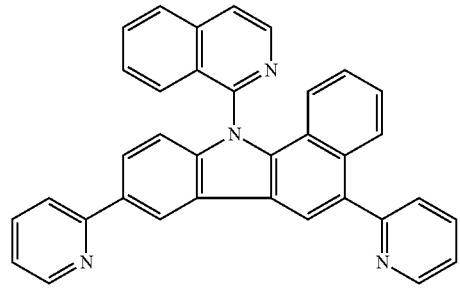
RI-20
RI-21
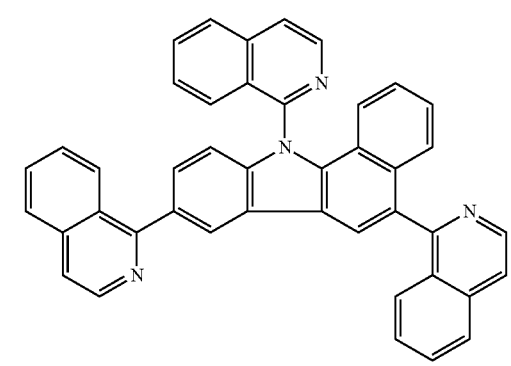

RI-22
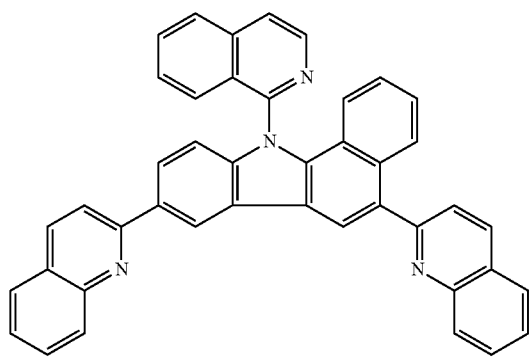
RI-23
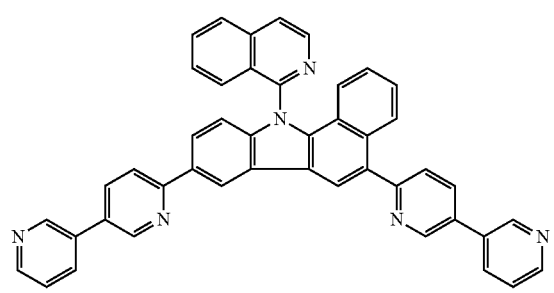
RI-24
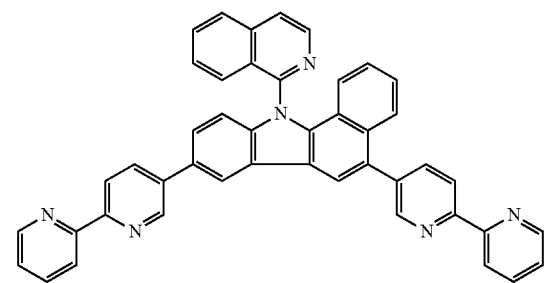
RI-25
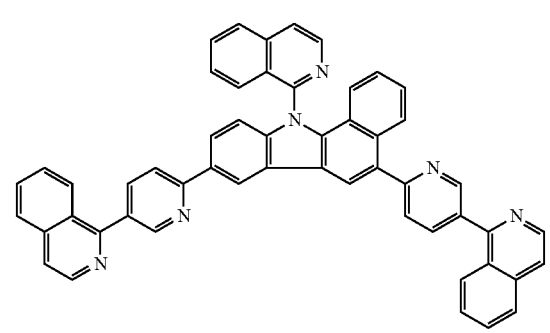
RI-26
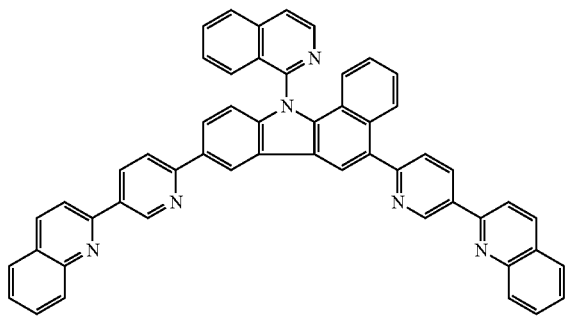
RI-27
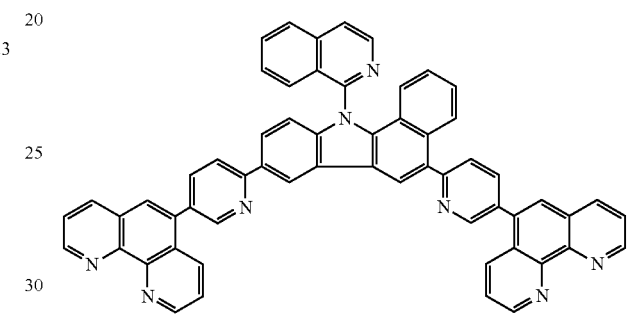
RI-28
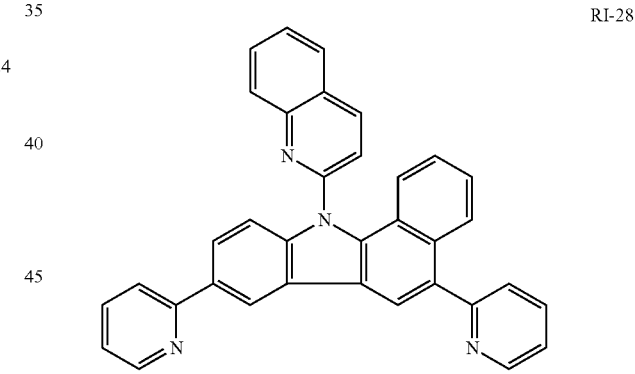
RI-29
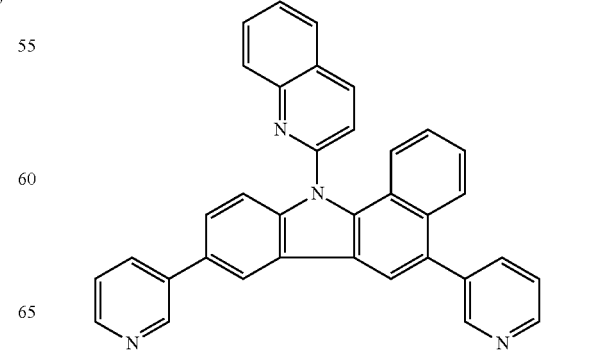

RI-30
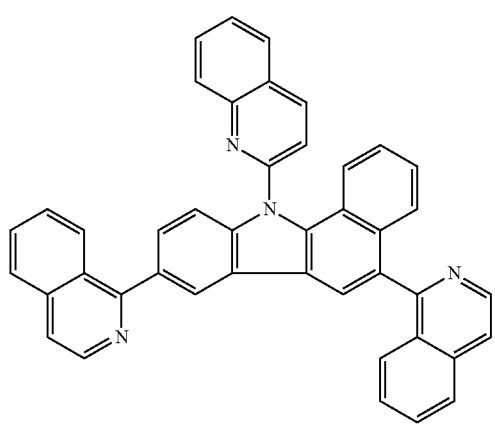
RI-31
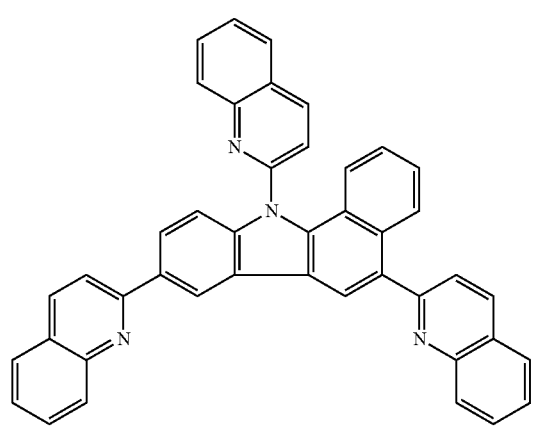
RI-32
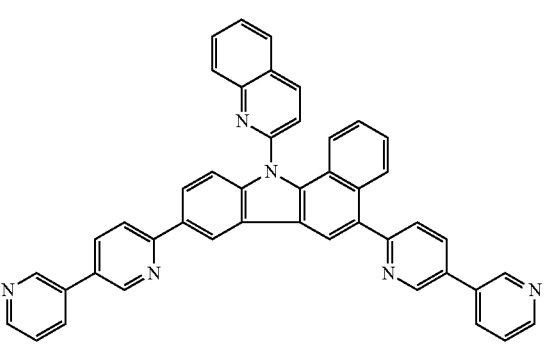
RI-33
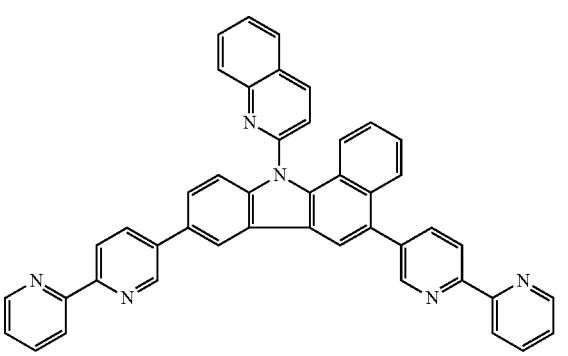
RI-34
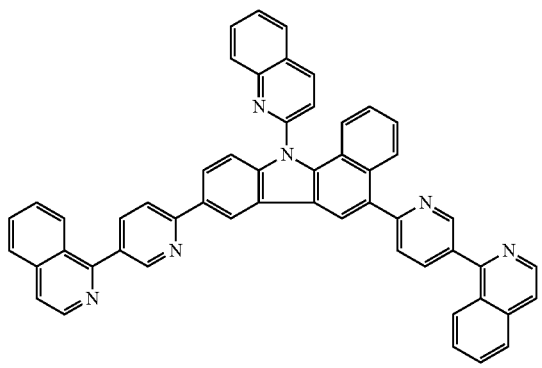
RI-35
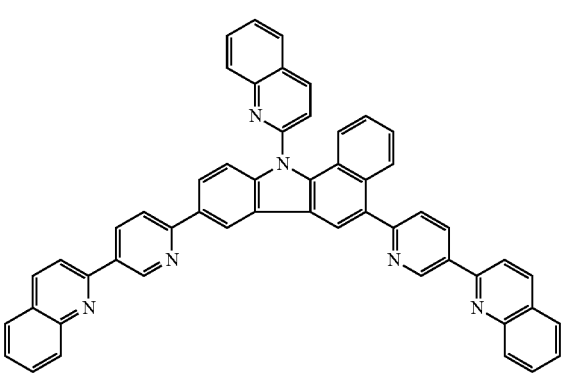
RI-36
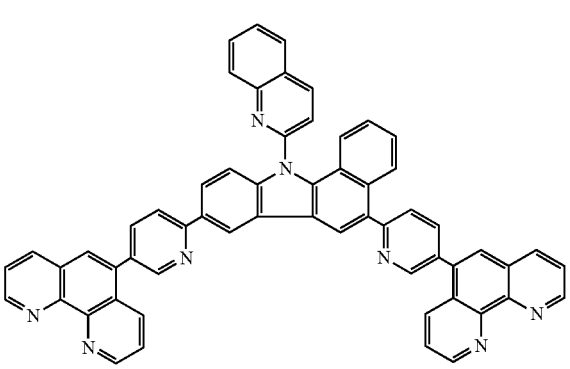
RI-37
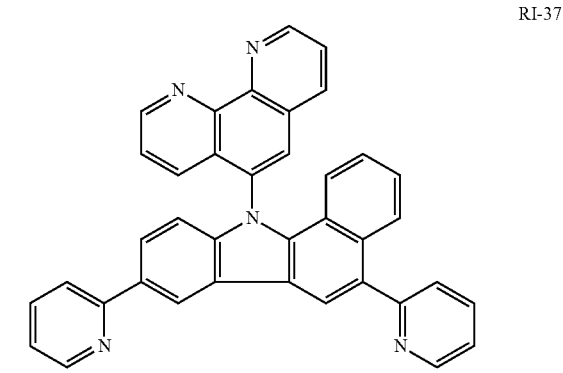

RI-38
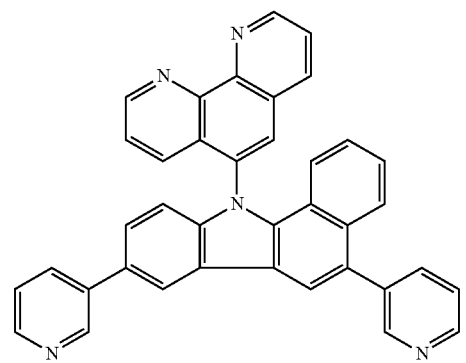
RI-39
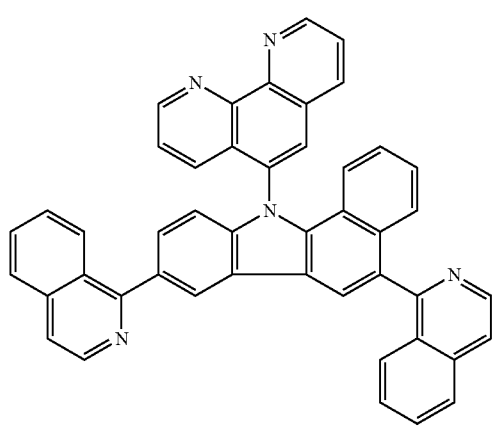
RI-40
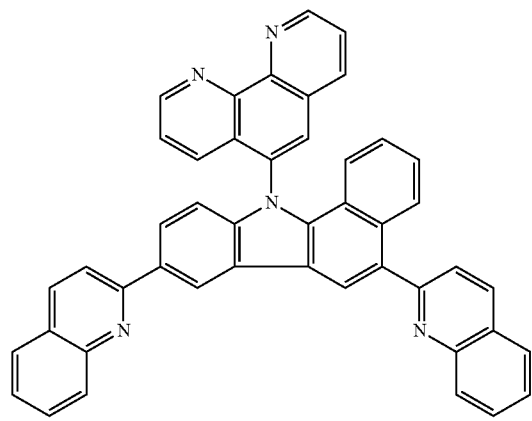
RI-41
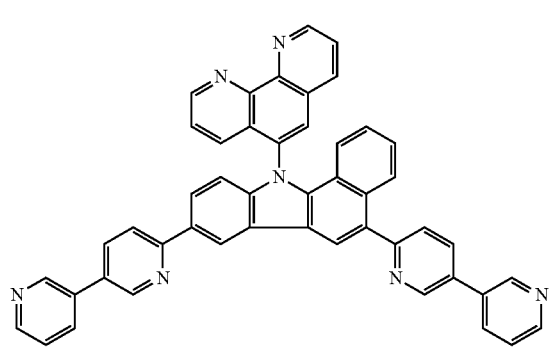
RI-42
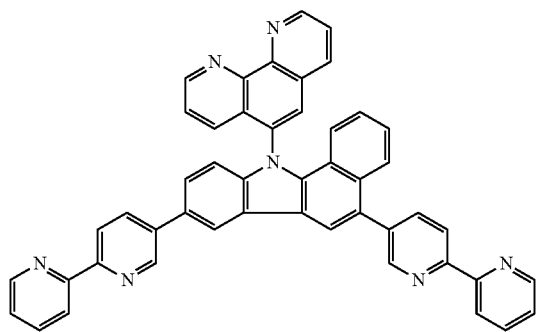
RI-43
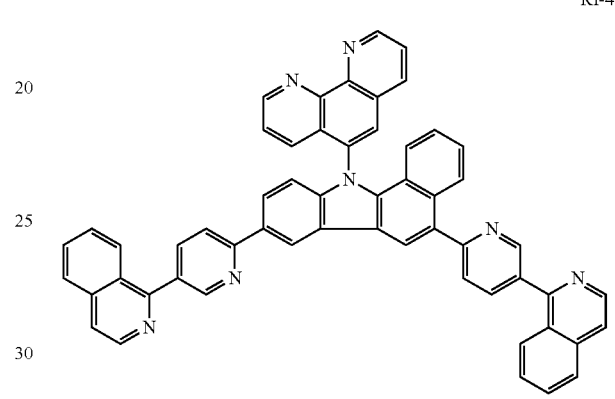
RI-44
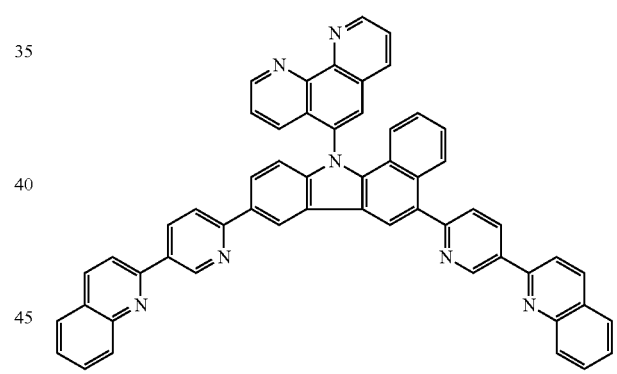
RI-45
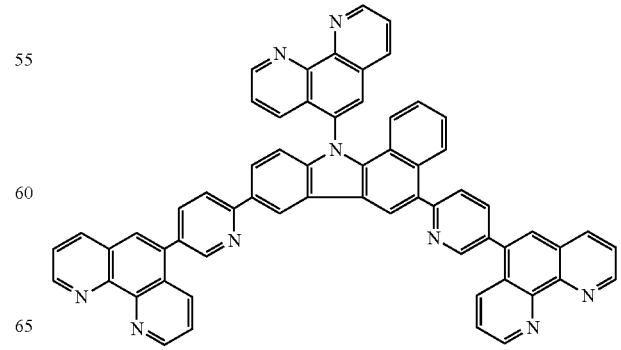

RI-46
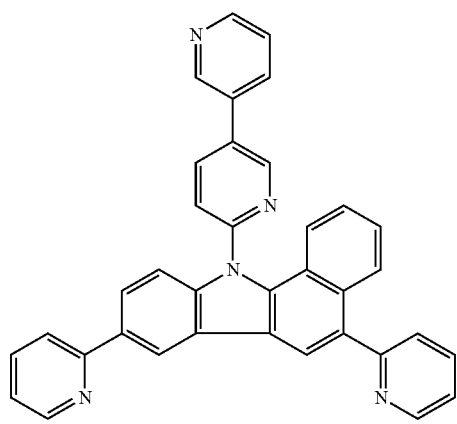
RI-47
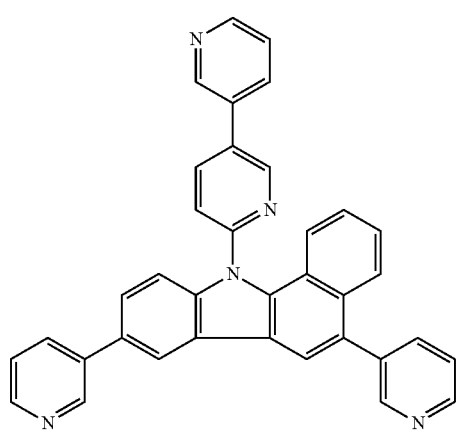
RI-48
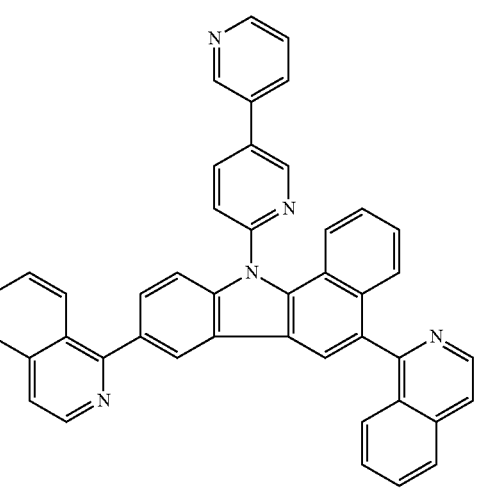
RI-49
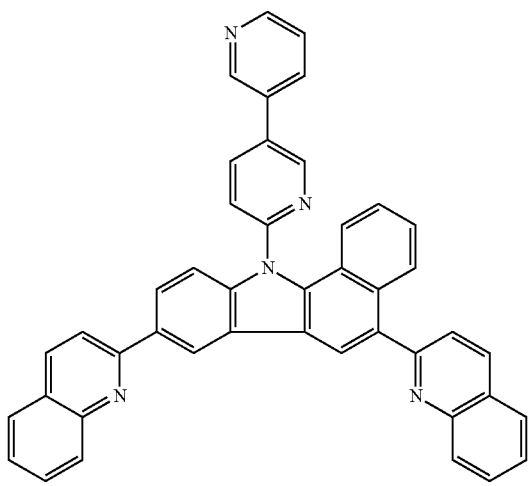
RI-50
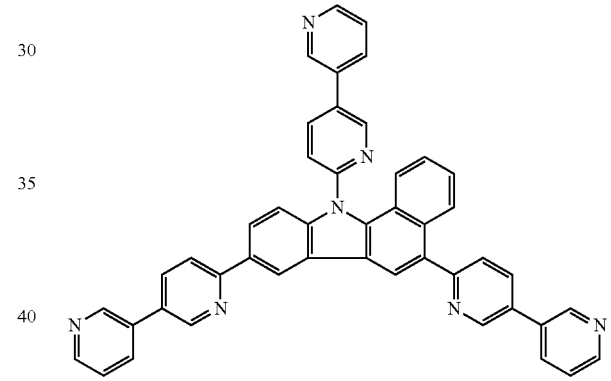
RI-51
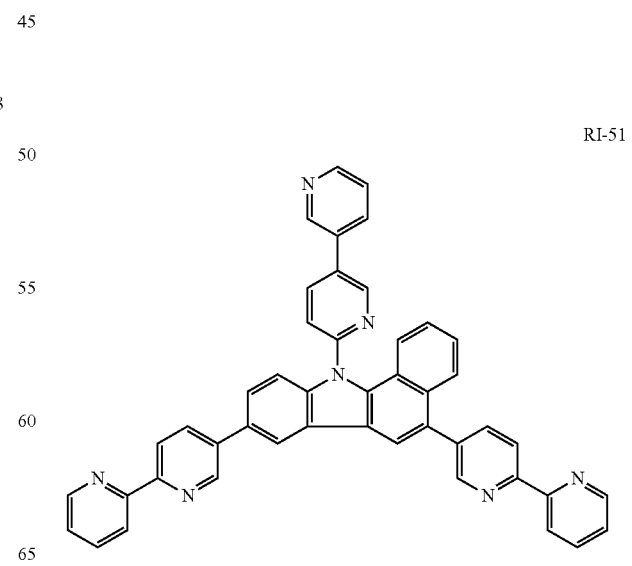

-continued
RI-52
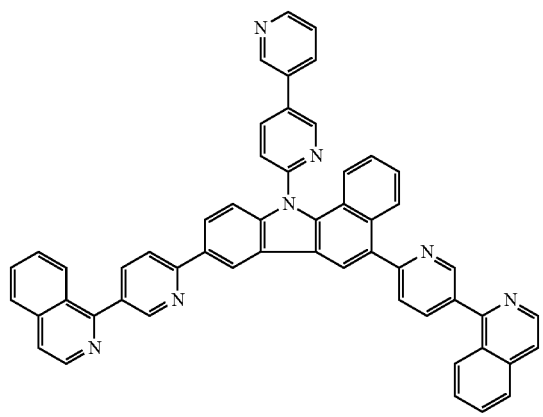
RI-53
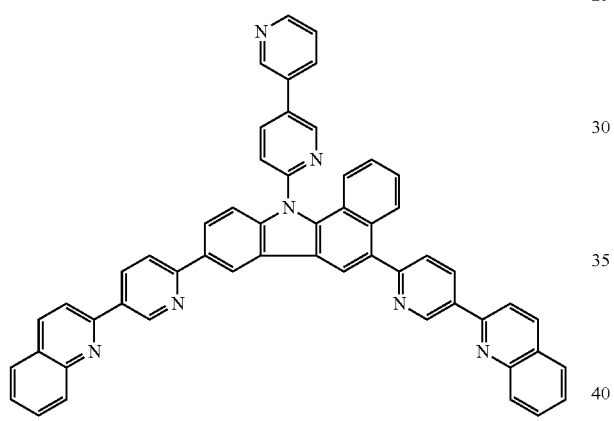
RI-54
-continued
RI-55
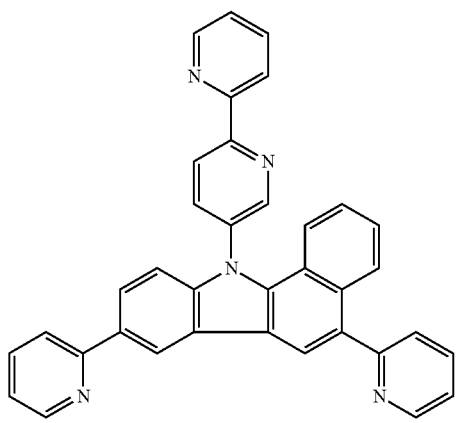
RI-56
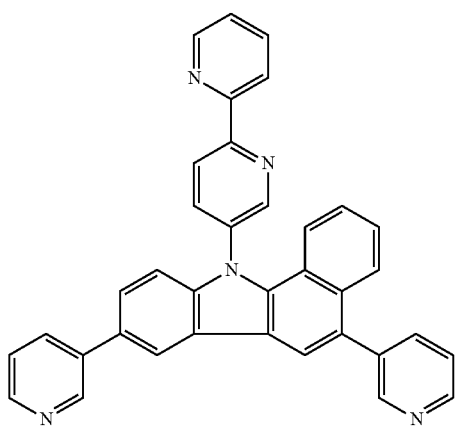
RI-57
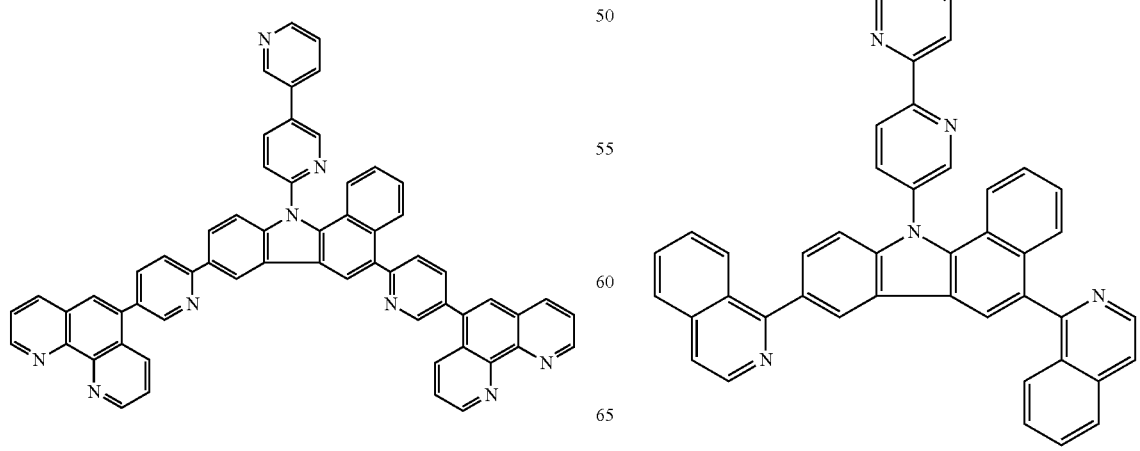

RI-58
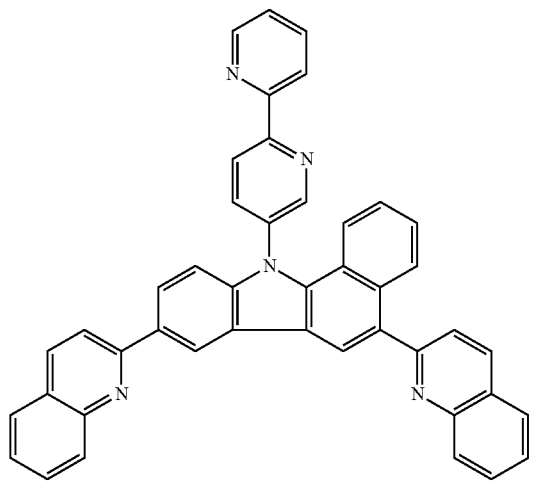
RI-59
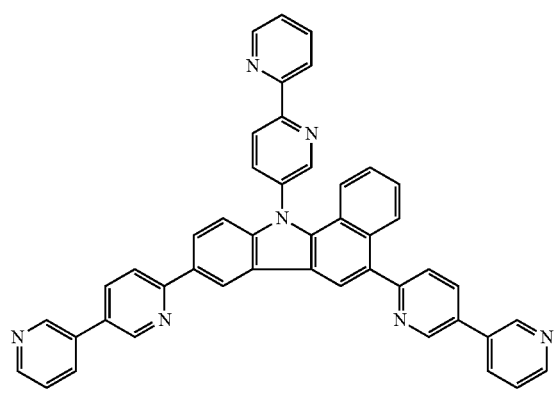
RI-60
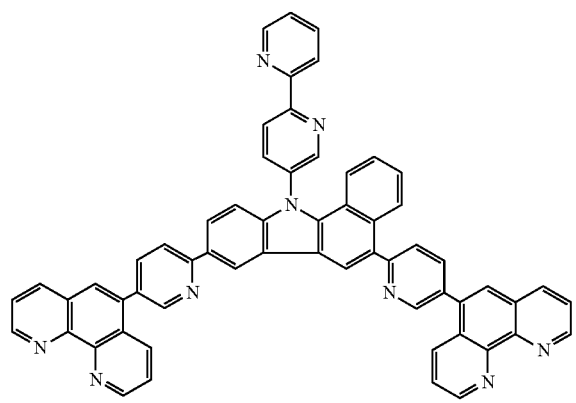
RI-61
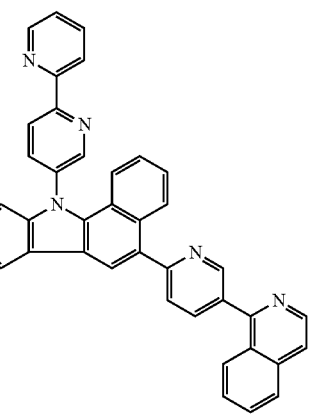
RI-62
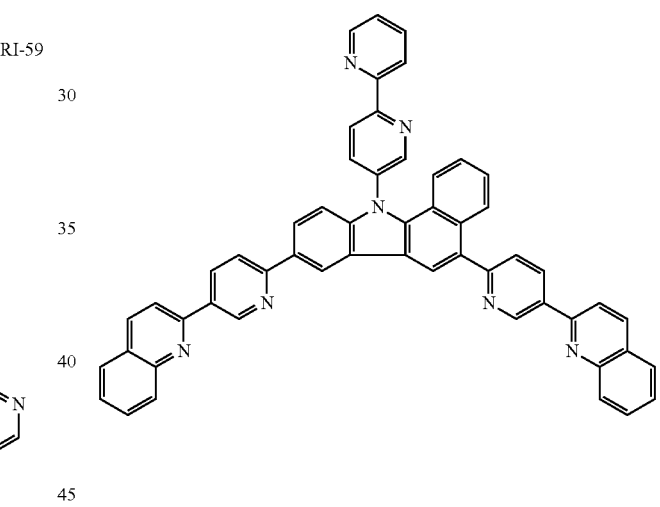
RI-63

RI-64
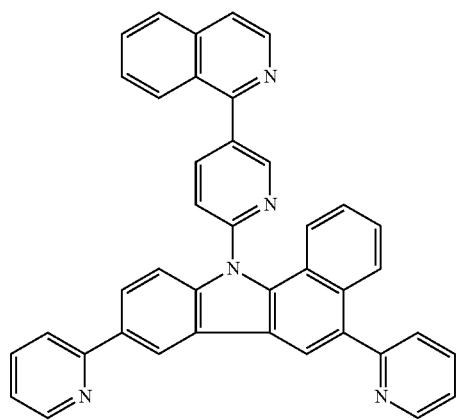
RI-67
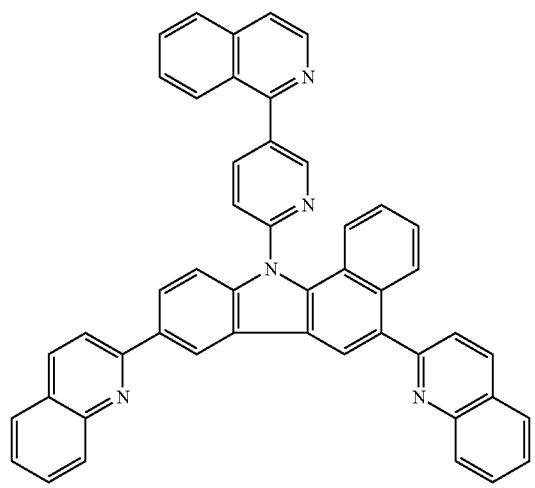
RI-65
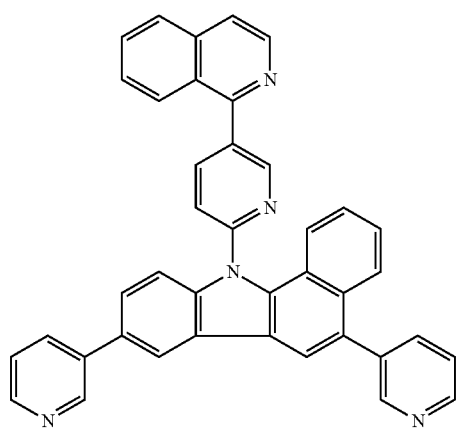
RI-68
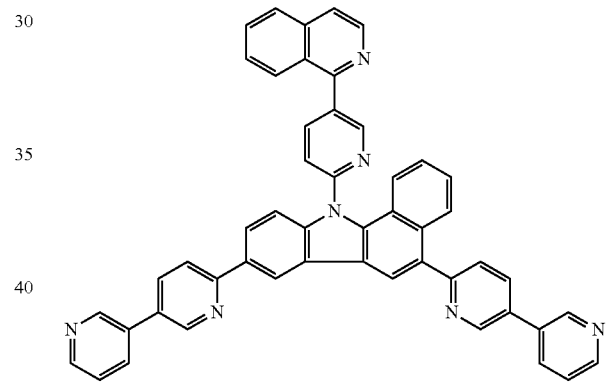
RI-66
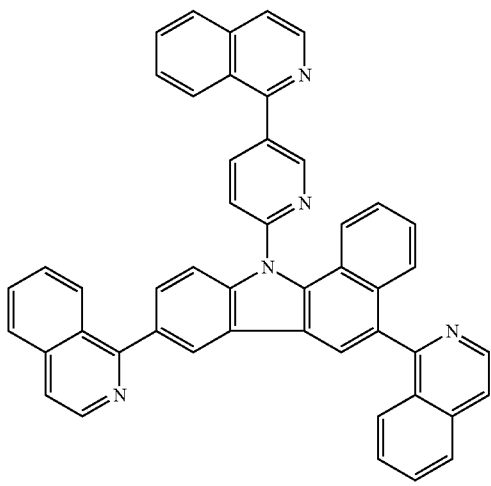
RI-69
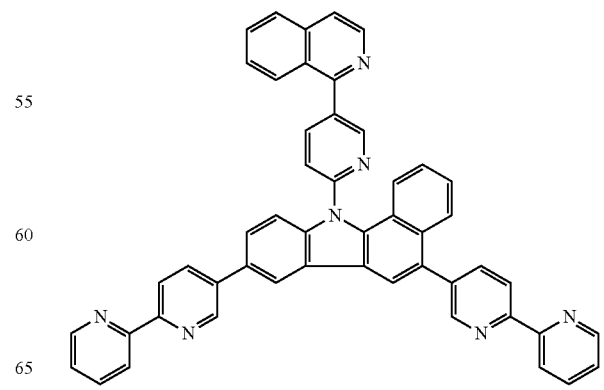

-continued
RI-70
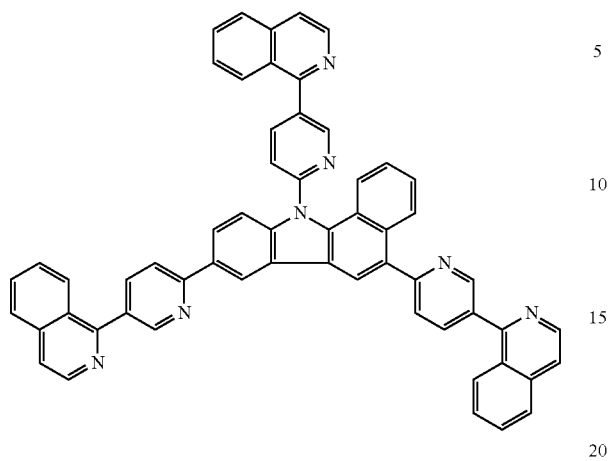
RI-71
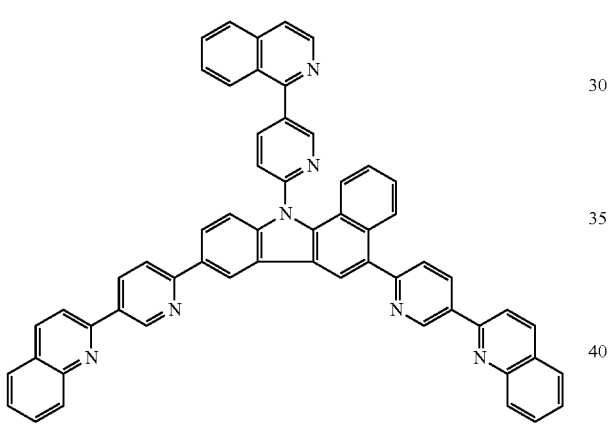
RI-72
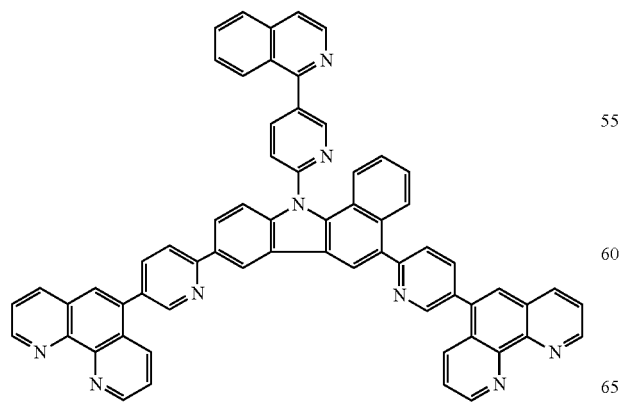
-continued
RI-73
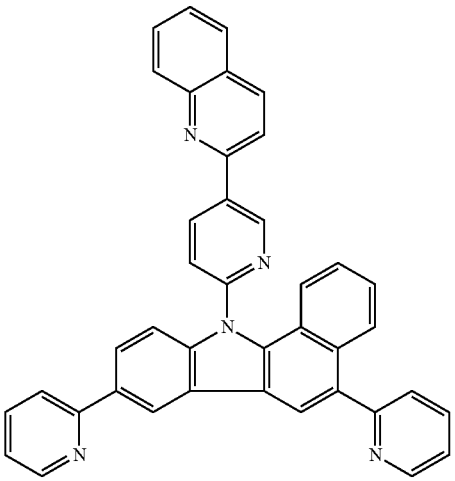
RI-74
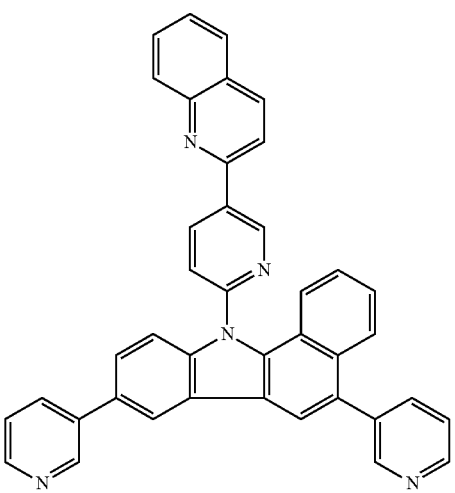
RI-75
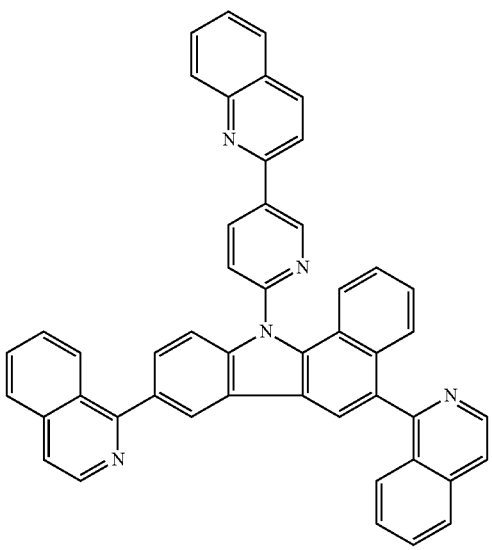

RI-76
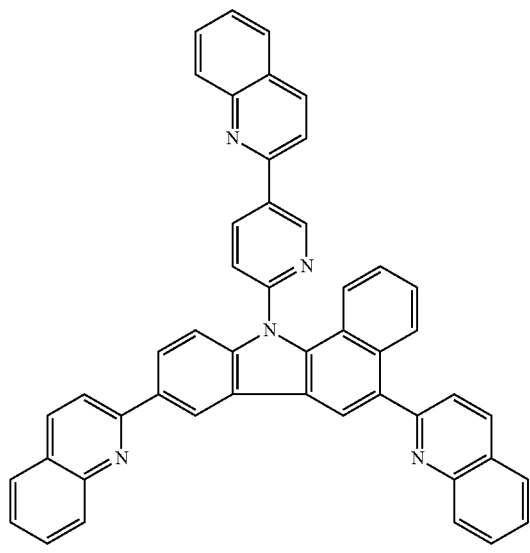
RI-77
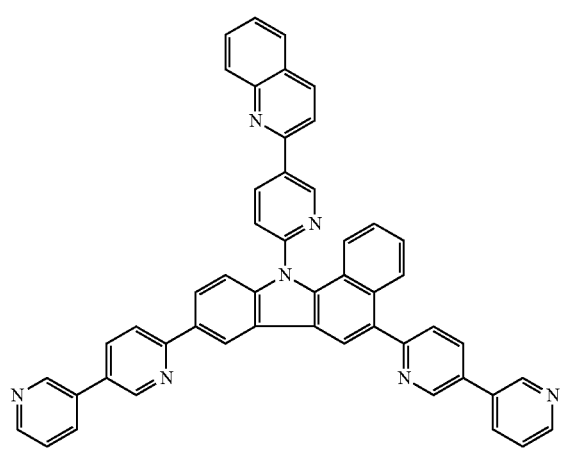
RI-78
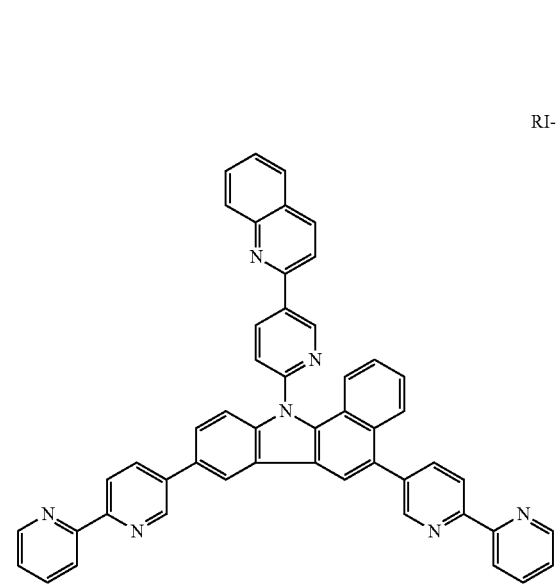
RI-79
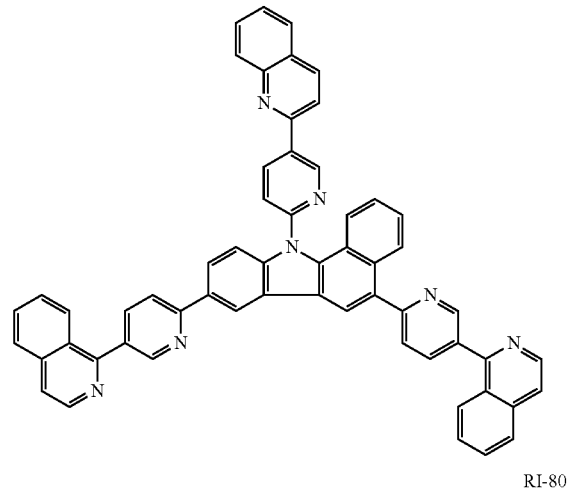
RI-80
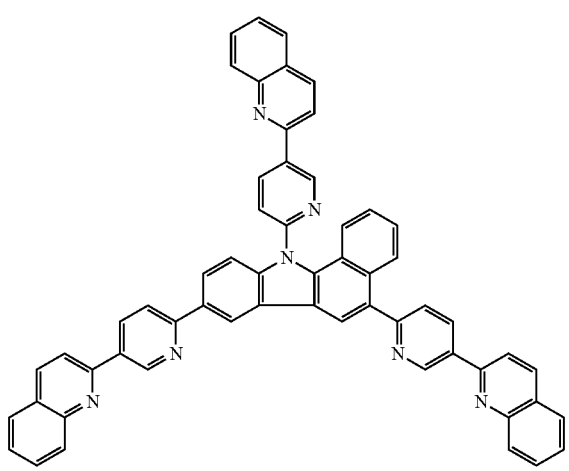
RI-81
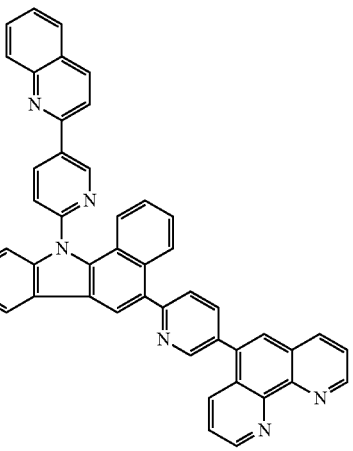

RI-82
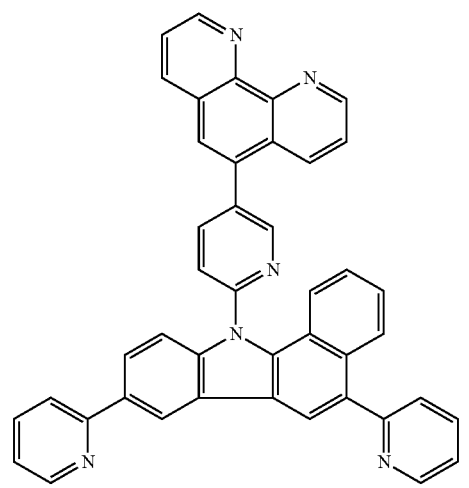
RI-83
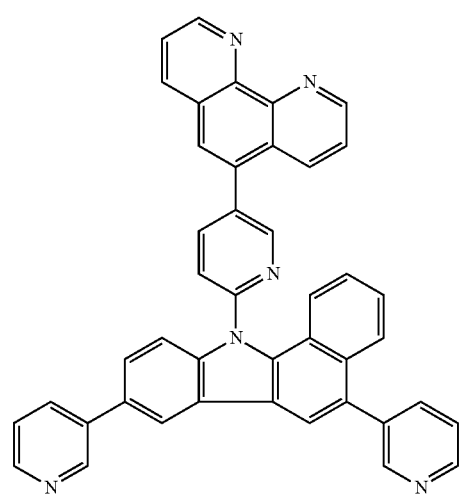
RI-84
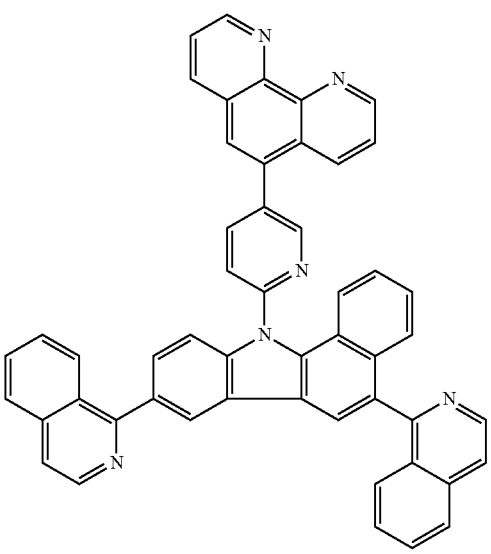
RI-85
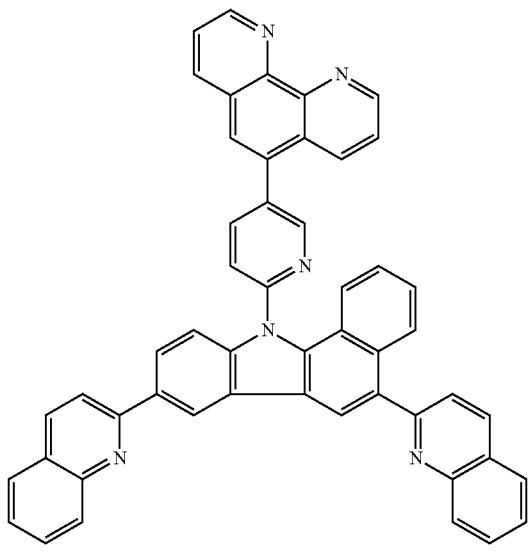
RI-86
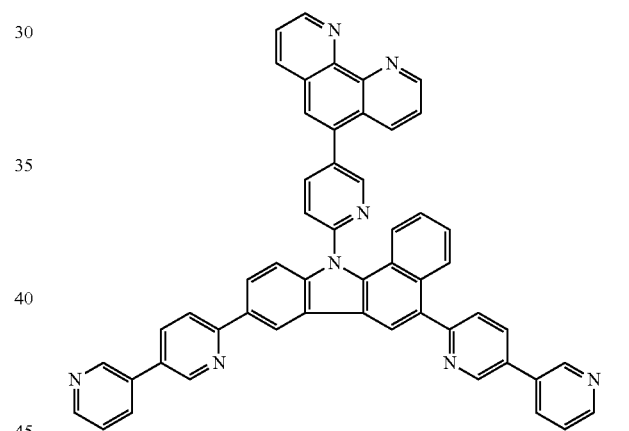
RI-87
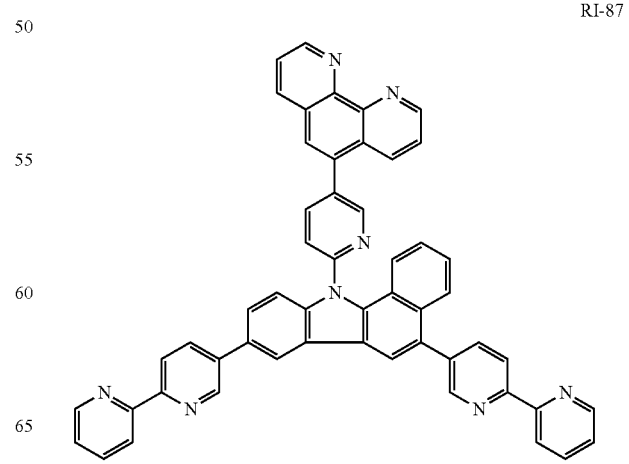

RI-88

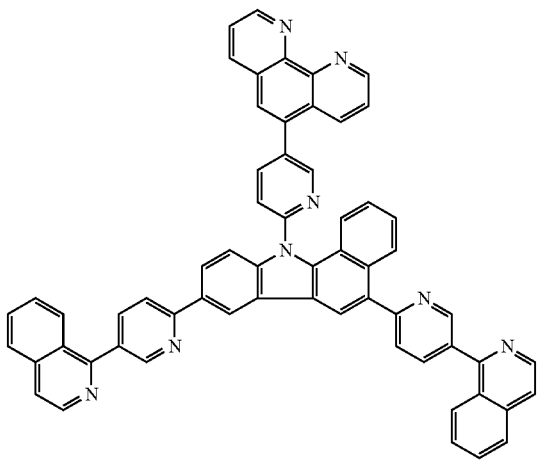

RI-89

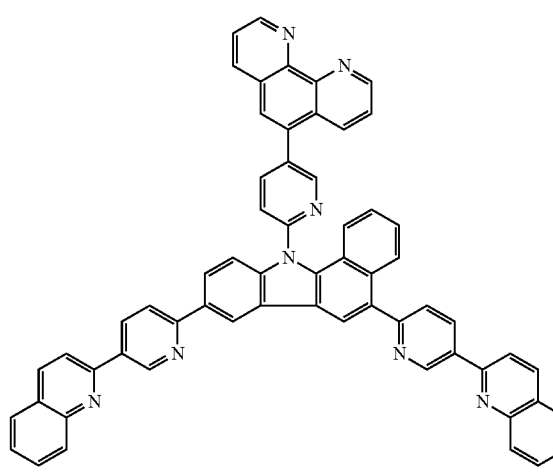

RI-90

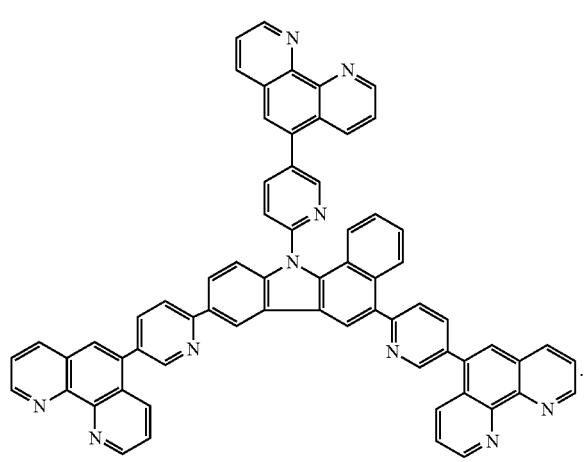

11. An organic light emitting diode device, comprising:
a first electrode;
a second electrode facing the first electrode; and
an emitting material layer between the first and second electrodes and including a red phosphorescent compound having the following formula:

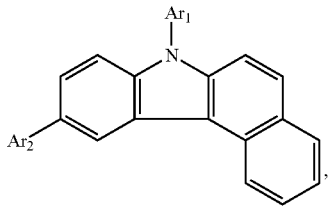

wherein Ar1 is selected from substituted or non-substituted pyridine, substituted or non-substituted quinoline and substituted or non-substituted phenanthroline, and Ar2 is selected from substituted or non-substituted pyridine and substituted or non-substituted quinoline.

12. The device according to claim 11, wherein the red phosphorescent compound is soluble in a non-polar solvent.

13. The device according to claim 11, wherein the red phosphorescent compound serves as a host in the emitting material layer.

14. An organic light emitting diode device, comprising:
a first electrode;
a second electrode facing the first electrode; and
an emitting material layer between the first and second electrodes and including a red phosphorescent compound having the following formula:

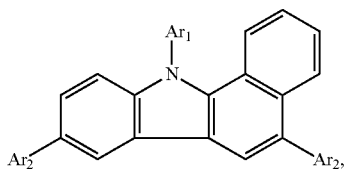

wherein Ar1 is selected from substituted or non-substituted pyridine, substituted or non-substituted quinoline and substituted or non-substituted phenanthroline, and Ar2 is selected from substituted or non-substituted pyridine and substituted or non-substituted quinoline.

15. The device according to claim 14, wherein the red phosphorescent compound is soluble in a non-polar solvent.

16. The device according to claim 14, wherein the red phosphorescent compound serves as a host in the emitting material layer.

* * * * *